(12) United States Patent
Scherz et al.

(10) Patent No.: US 8,815,213 B2
(45) Date of Patent: Aug. 26, 2014

(54) RGD-(BACTERIO)CHLOROPHYLL CONJUGATES FOR PHOTODYNAMIC THERAPY AND IMAGING OF NECROTIC TUMORS

(75) Inventors: Avigdor Scherz, Rehovot (IL); Liat Goldshaid, Rehovot (IL); Yoram Salomon, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 545 days.

(21) Appl. No.: 12/920,088

(22) PCT Filed: Mar. 1, 2009

(86) PCT No.: PCT/IL2009/000228
§ 371 (c)(1),
(2), (4) Date: Nov. 30, 2010

(87) PCT Pub. No.: WO2009/107139
PCT Pub. Date: Sep. 3, 2009

(65) Prior Publication Data
US 2011/0064658 A1    Mar. 17, 2011

Related U.S. Application Data

(60) Provisional application No. 61/064,298, filed on Feb. 27, 2008.

(51) Int. Cl.
*A61B 5/055* (2006.01)
*A61K 51/04* (2006.01)
*A61K 41/00* (2006.01)
*C07D 257/04* (2006.01)

(52) U.S. Cl.
CPC ......... *A61K 51/0485* (2013.01); *A61K 41/0057* (2013.01); *A61K 51/0451* (2013.01); *A61K 51/0446* (2013.01); *A61K 51/044* (2013.01); *C07D 257/04* (2013.01)
USPC ......... 424/9.363; 424/1.65; 424/9.1; 424/9.2; 424/9.36; 424/9.361; 424/9.362; 424/9.6

(58) Field of Classification Search
CPC ... A61K 49/00; A61K 49/0008; A61K 49/12; A61K 49/10; A61K 49/0002; A61K 49/0004; A61K 51/06; A61K 51/00; A61K 51/02; A61K 51/04; A61K 51/0497; A61K 51/041; A61K 51/044; A61K 51/0446; A61K 51/0451; A61K 51/0485; A61K 41/0057; A61K 41/00; A61K 41/0071; A61K 2123/00; A61K 2121/00; C07D 257/02; C07D 487/22; C07D 257/00; C07D 257/04; C07D 487/00
USPC ................. 424/1.11, 1.65, 1.69, 9.1, 9.2, 9.3, 424/9.323, 9.34, 9.341, 9.36, 9.361, 9.362, 424/9.363, 9.364, 9.365, 9.6, 9.61; 540/145, 201, 202, 203, 205; 530/300, 530/316, 317, 324, 325, 326, 327, 328, 329, 530/330
See application file for complete search history.

(56) References Cited

U.S. PATENT DOCUMENTS

| 5,650,292 | A | 7/1997 | Scherz et al. |
| 5,726,169 | A | 3/1998 | Scherz et al. |
| 5,789,433 | A | * 8/1998 | Chan et al. ............ 514/410 |
| 5,955,585 | A | 9/1999 | Scherz et al. |
| 6,147,195 | A | 11/2000 | Scherz et al. |
| 6,333,319 | B1 | 12/2001 | Scherz et al. |
| 6,569,846 | B1 | 5/2003 | Scherz et al. |
| 6,576,239 | B1 | 6/2003 | Ruoslahti et al. |
| 6,740,637 | B1 | 5/2004 | Scherz et al. |
| 7,045,117 | B2 | 5/2006 | Scherz et al. |
| 2003/0027235 | A1* | 2/2003 | Kraus et al. ............ 435/13 |
| 2007/0258908 | A1* | 11/2007 | Lanza et al. ............ 424/9.322 |
| 2011/0223102 | A1* | 9/2011 | Pandey et al. ............ 424/1.11 |

FOREIGN PATENT DOCUMENTS

| DE | 4121876 A1 | 1/1993 |
| WO | WO 9810795 A2 | 3/1998 |
| WO | WO 0140232 A1 | 6/2001 |
| WO | WO 2004045492 A2 | 6/2004 |
| WO | WO 2005120573 A2 | 12/2005 |
| WO | WO 2008023378 A1 | 2/2008 |
| WO | WO 2009/038660 | * 3/2009 |

OTHER PUBLICATIONS

Goldshaid et al., "Novel design principles enable specific targeting of imaging and therapeutic agents to necrotic domains in breast tumors" Breast Cancer Research, pp. 1-18,12:R29 (2010) Online [http://breast-cancer-research.com/content/12/3/R29].
Arap W., Pasqualini R. and Ruoslahti E.. (1998) "Cancer treatment by targeted drug delivery to tumor vasculature in a mouse model", Science, 279:377-380.
Arap W., Haedicke W., Bernasconi M., Kain R., Rajotte D., Krajewski S., Ellerby H.M., Bredesen D.E., Pasqualini R. and Ruoslahti E. (2002) "Targeting the prostate for destruction through a vascular address", Proc. Natl. Acad. Sci. U.S.A., 99(3):1527-1531.
Brandis A., Mazor O., Gross S., Koudinova N., Hami R., Kalin-Kammhuber N., Rosenbach-Belkin V., Greenwald M., Bondon A., Simonneaux G., Scheer H., Salomon Y. and Scherz A. (2003) "Novel palladium-bacteriochlorophyll derivatives for antivascular Photodynamic therapy: synthesis, phototoxicity, pharmacokinetics and efficacy", J. Med. Chem. submitted.
Chaleix V., Sol V., Huang Y.M., Guilloton M., Granet R., Blais J.C., and Krausz P. (2003) "RGD-porphyrin conjugates: synthesis and potential application in photodynamic therapy", Eur. J. Org. Chem., 1486-1493.
Ellerby H.M., Arap W., Ellerby L.M., Kain R., Andrusiak R., Del Rio G., Krajewski S., Rao R., Ruoslahti E., Bredesen D.E. and Pasqualini R. (1999) "Anti-cancer activity of targeted pro-apoptotic peptides", Nat. Med., 5(9):1032-1038.

(Continued)

*Primary Examiner* — D L Jones
(74) *Attorney, Agent, or Firm* — Browdy and Neimark, PLLC

(57) ABSTRACT

RGD-chlorophyll and RGD-bacteriochlorophyll conjugates that home and accumulate in necrotic tumor domains much longer than in tumor non-necrotic domains are provided for use in minimally invasive tumor-targeted imaging, tumor-targeted photodynamic therapy, and/or on-line prognosis of necrotic tumors.

22 Claims, 33 Drawing Sheets
(31 of 33 Drawing Sheet(s) Filed in Color)

(56) References Cited

OTHER PUBLICATIONS

Haubner R., Wester H.J., Weber W.A., Mang C., Ziegler S.L., Goodman S.L., Senekowitsch-Schmidtke R., Kessler H. and Schwaiger M. (2001) "Noninvasive imaging of avb3 integrin expression using 18F-labeled RGD-containing glycopeptide and positron emission tomography", Cancer res., 61:1781-1785.

Janssen M.L., Oyen W.J., Dijkgraaf I., Massuger L.F., Frielink C., Edwards D.S., Rajopadhye M., Boonstra H., Corstens F.H., Boerman O.C. (2002a) Tumor Targeting with Radiolabeled $\alpha v\beta 3$ Integrin Binding Peptides in a Nude Mouse Model. Cancer research 62: 6146-6151.

Janssen M, Oyen WJ, Massuger LF, Frielink C, Dijkgraaf I, Edwards DS, Radjopadhye M, Corstens FH, Boerman OC.(2002b) Comparison of a monomeric and dimeric radiolabeled RGD-peptide for tumor targeting.Cancer Biother Radiopharm. 17(6):641-646.

Koudinova N.V., Pinthus J.H., Brandis A., Brenner O., Bendel P., Ramon J., Eshhar Z., Scherz A. and Salomon Y. (2003) "Photodynamic therapy with Pd-Bacteriopheophorbide (TOOKAD): successful in vivo treatment of human prostatic small cell carcinoma xenografts", Int J Cancer., 104(6):782-789.

Temming K. et al. (2005) RGD-based strategies for selective delivery of therapeutics and imaging agents to the tumour vasculature. Drug resistance updates. 8(6):381-402.

Chaleix et al.,( 2004), "Efficient synthesis of RGD-containing cyclic peptide-porphyrin conjugates by ring-closing metathesis on solid support" Tetrahedron Lett. 45(27):5295-5299.

Sternberg et al., (1998), "Porphyrin-based photosensitizers for use in photodynamic therapy" Tetrahedron, 54 (17):4151-4202.

Frochot et al.,(2007), "Interest of RGD-containing linear or cyclic peptide targeted tetraphenylchlorin as novel photosensitizers for selective photodynamic activity" Bioorg. Chem. 35(3):205-220.

Sol et al., (2004), "Amino porphyrins as photoinhibitors of Gram-positive and -negative bacteria" Bioorg. Medicinal Chem. Letters 14(16):4207-4211.

Mazor, O., A. Brandis, et al. (2005). "WST11, a novel water-soluble bacteriochlorophyll derivative; cellular uptake, pharmacokinetics, biodistribution and vascular-targeted photodynamic activity using melanoma tumors as a model." Photochem Photobiol 81(2): 342-51.

Gross S, Gilead A, Scherz A, Neeman M, Salomon Y. (2003b) Monitoring photodynamic therapy of solid tumors online by BOLD-contrast MRI. Nat Med. 9(10):1327-31.

Conway C L et al,"In vivo and in vitro characterisation of a protoporphyrin IX—cyclic RGD peptide conjugate for use in photodynamic therapy" Photochem. Photobiol. Sci., (2008), 7, 290-298.

Boisbrun, M., Vanderesse, R., Engrand, P., Olie, A., Hupont, S., Regnouf-De-Vains, J.B., & Frochot, C. (2008). Design and photophysical properties of new RGD targeted tetraphenylchlorins and porphyrins. Tetrahedron, 64(16), 3494-3504.

\* cited by examiner

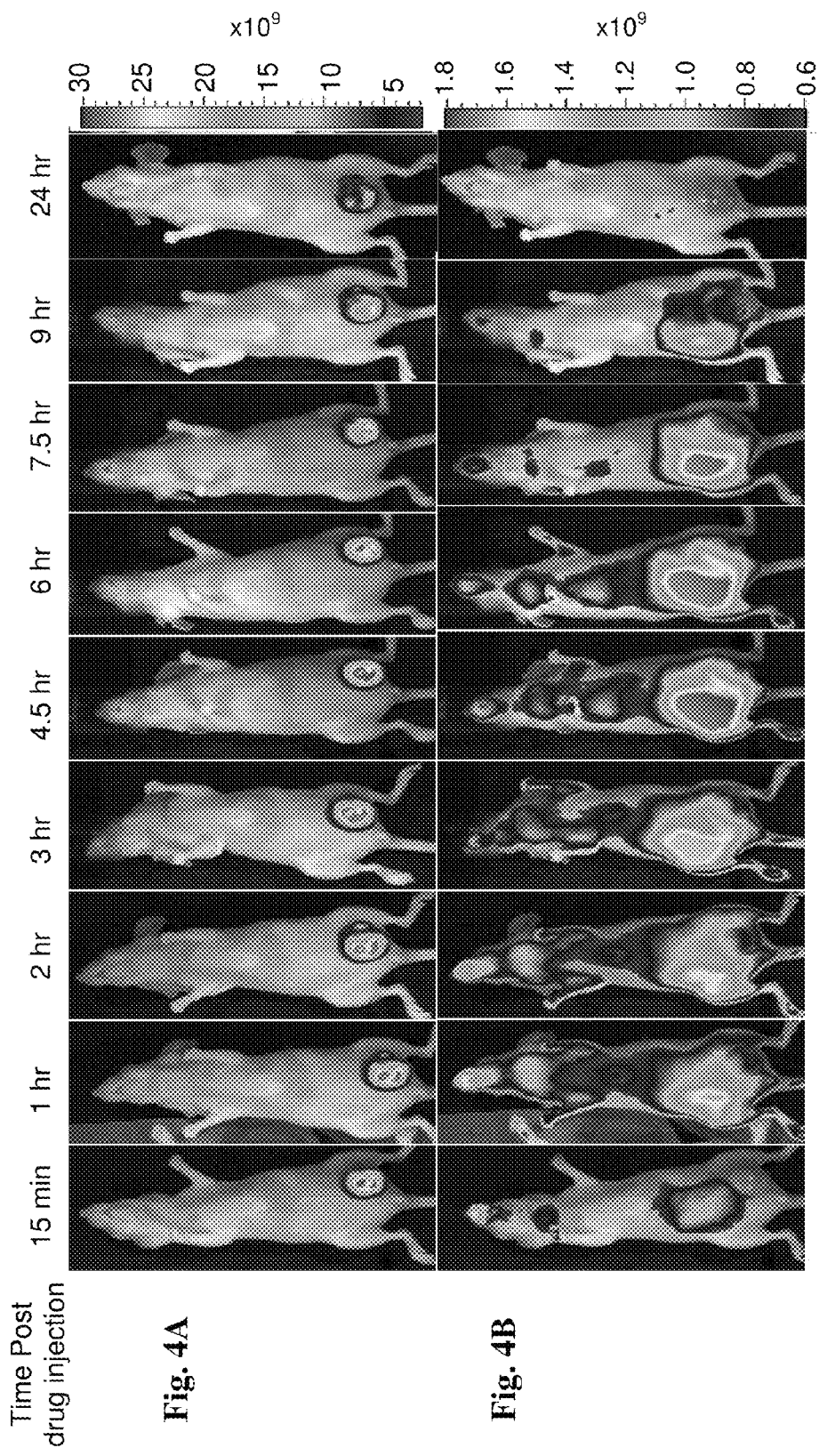

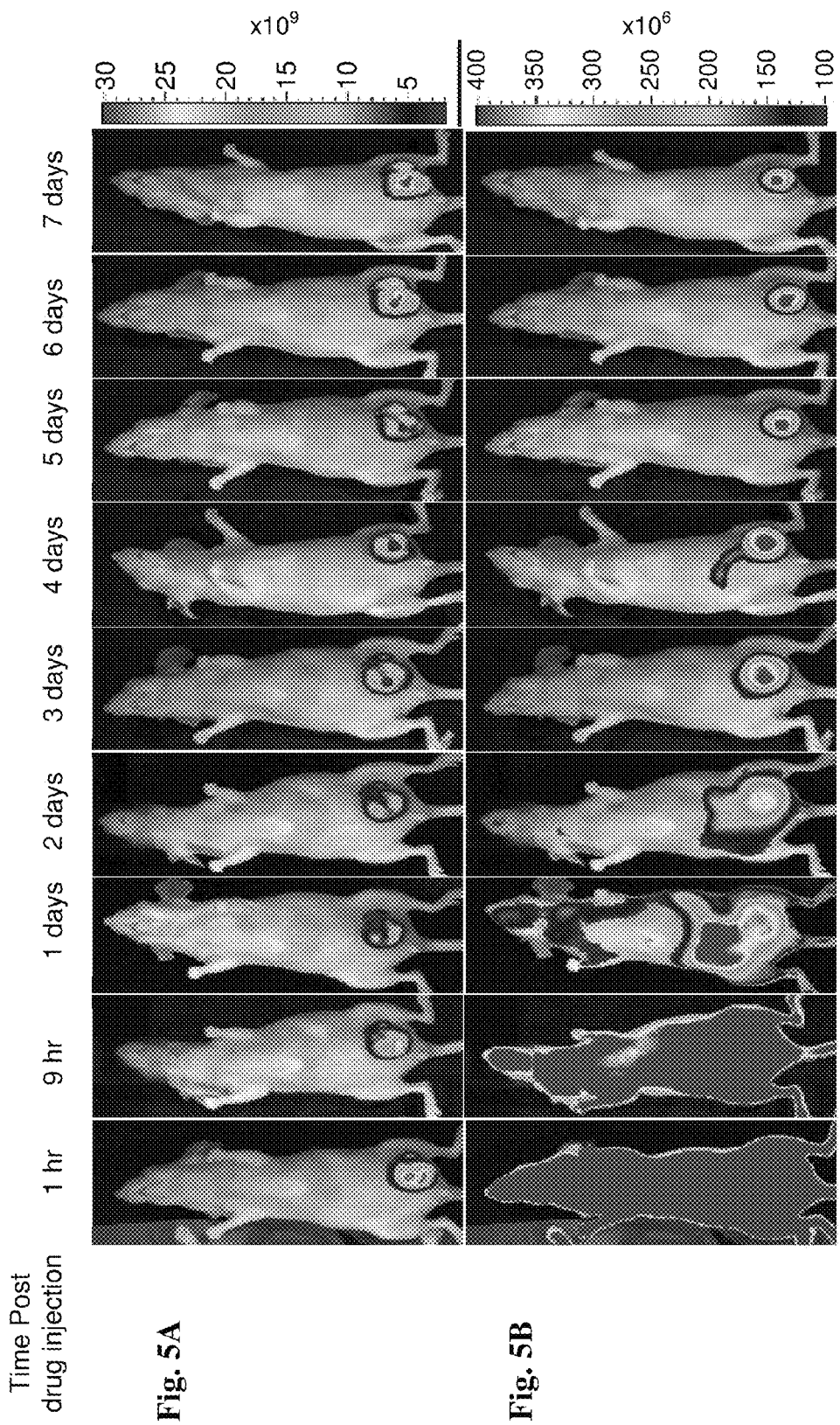

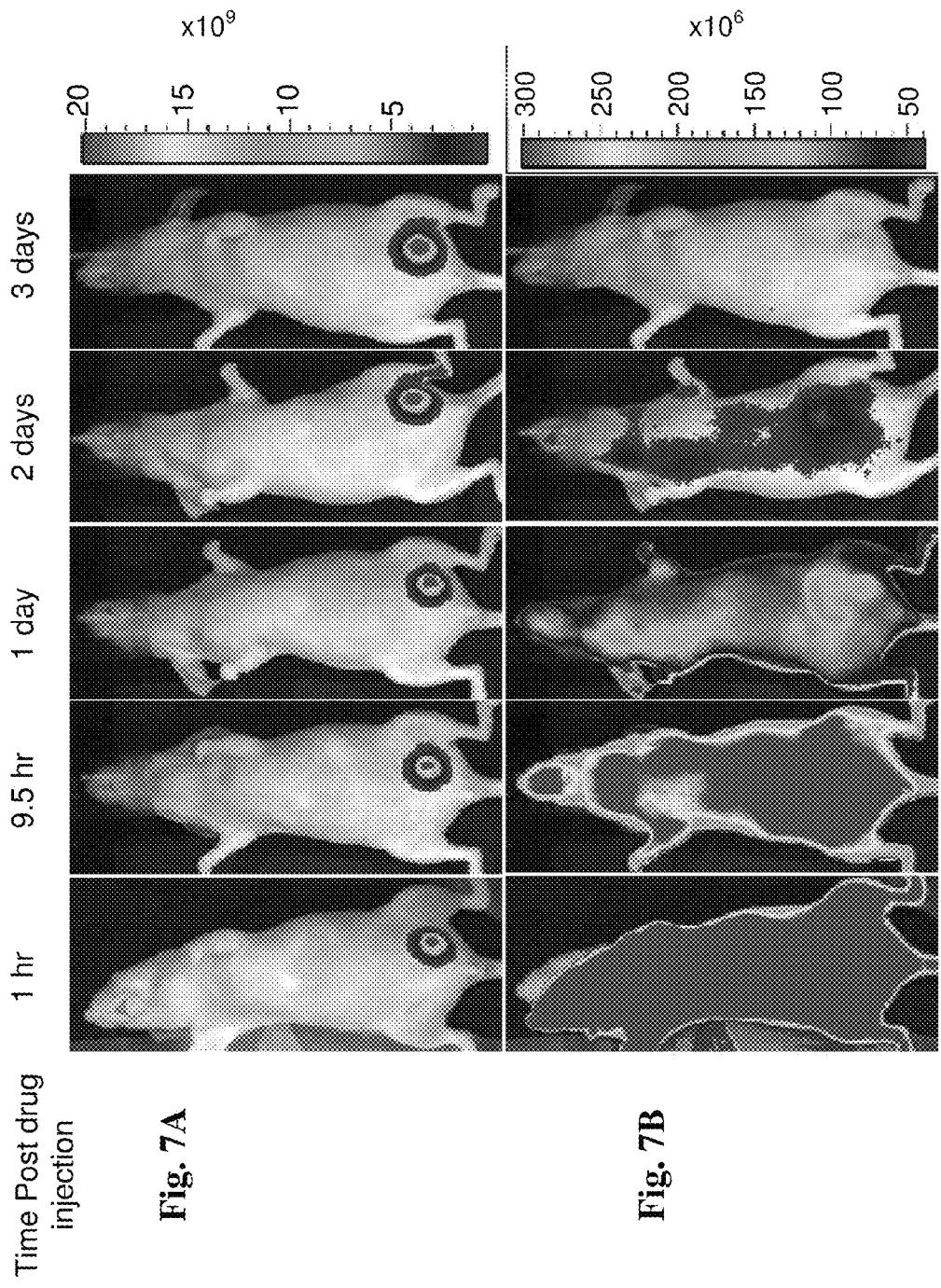

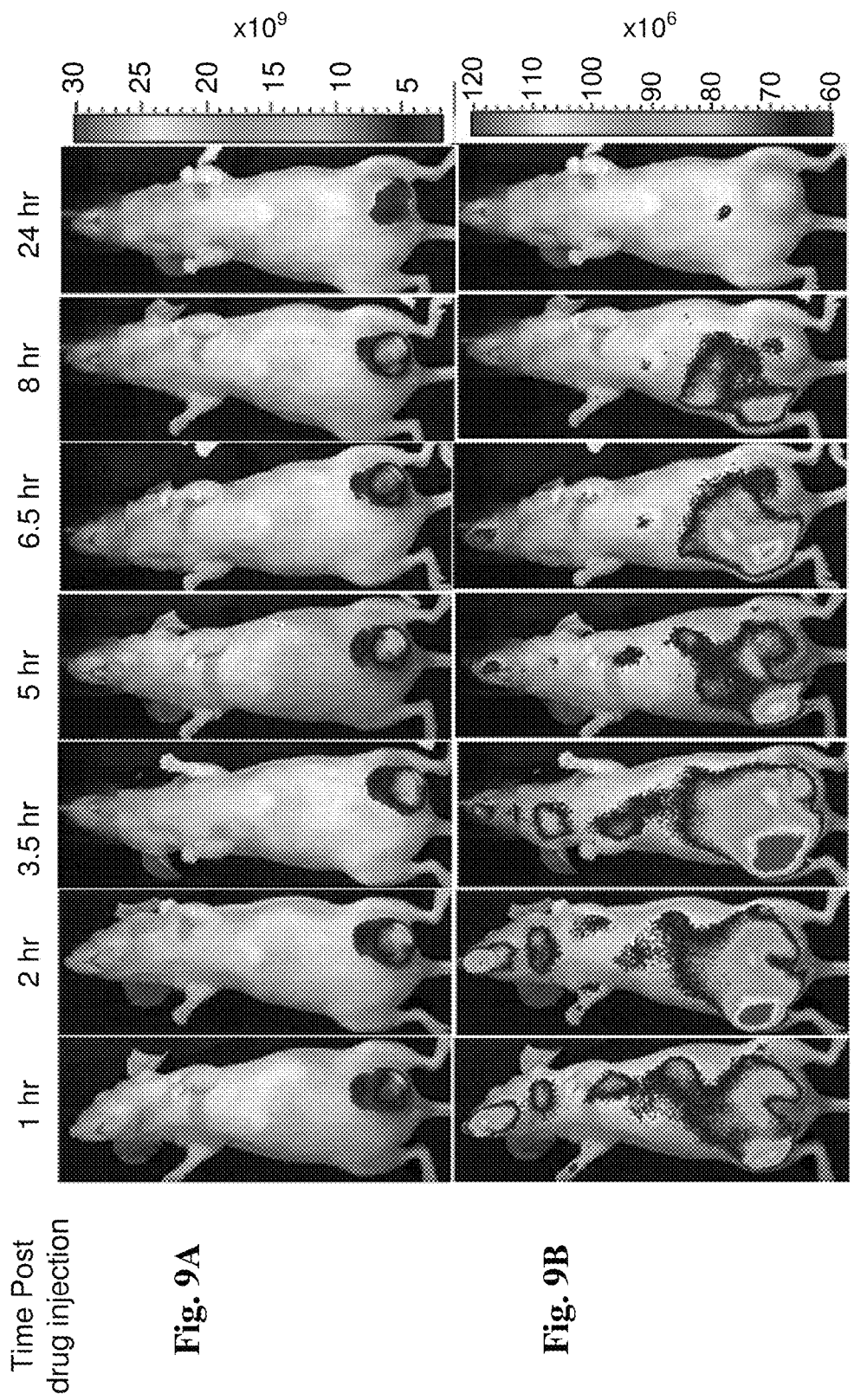

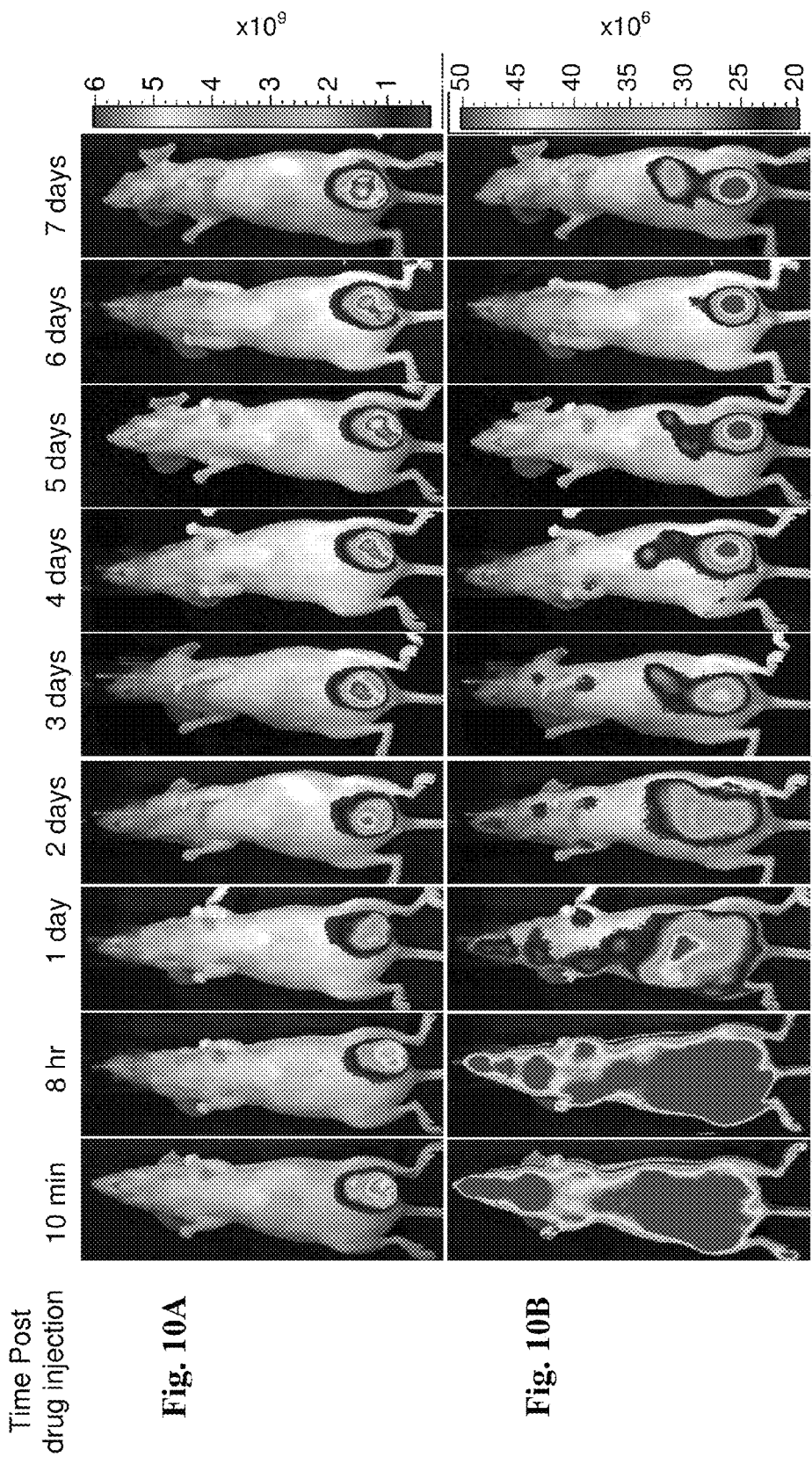

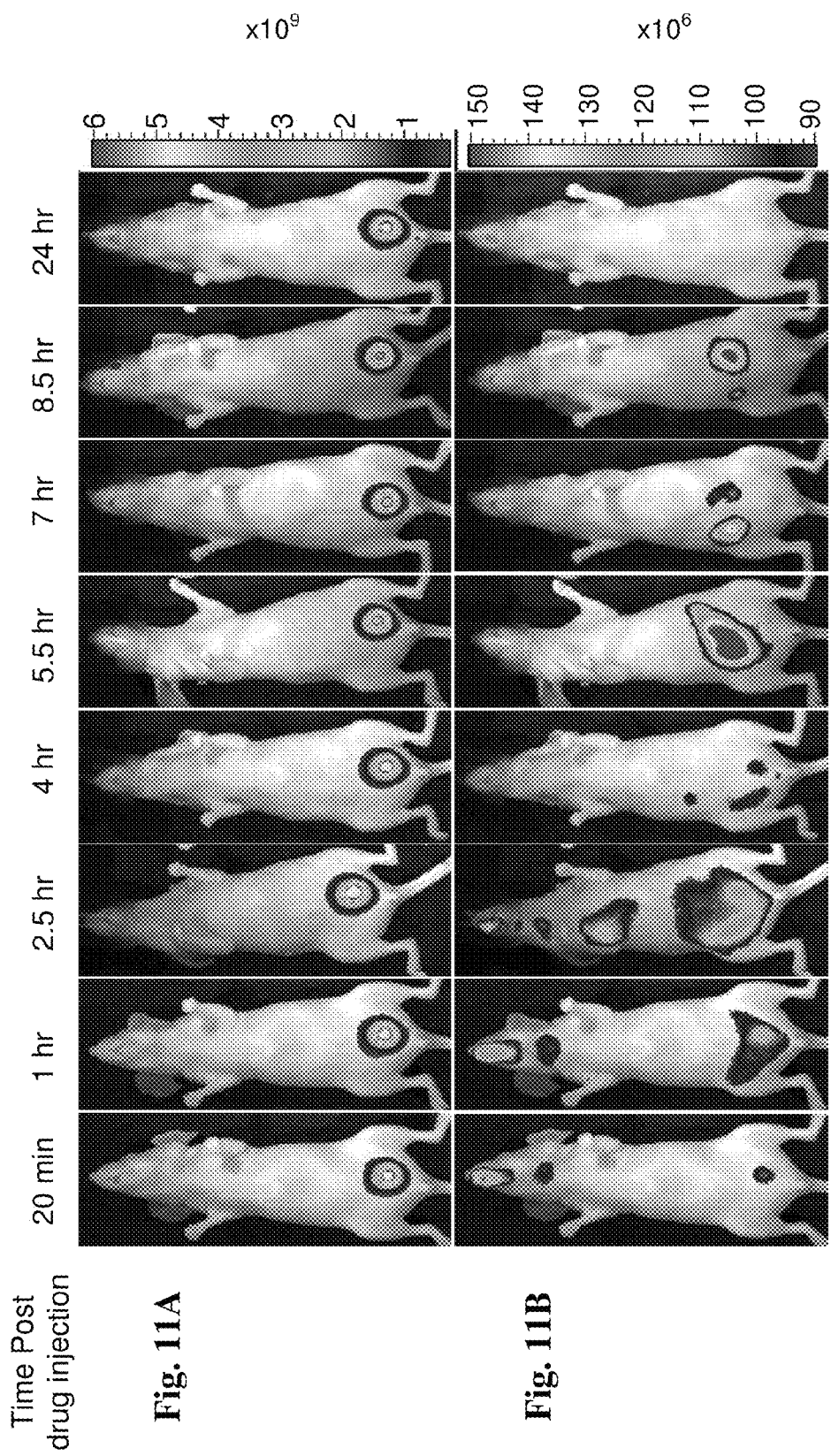

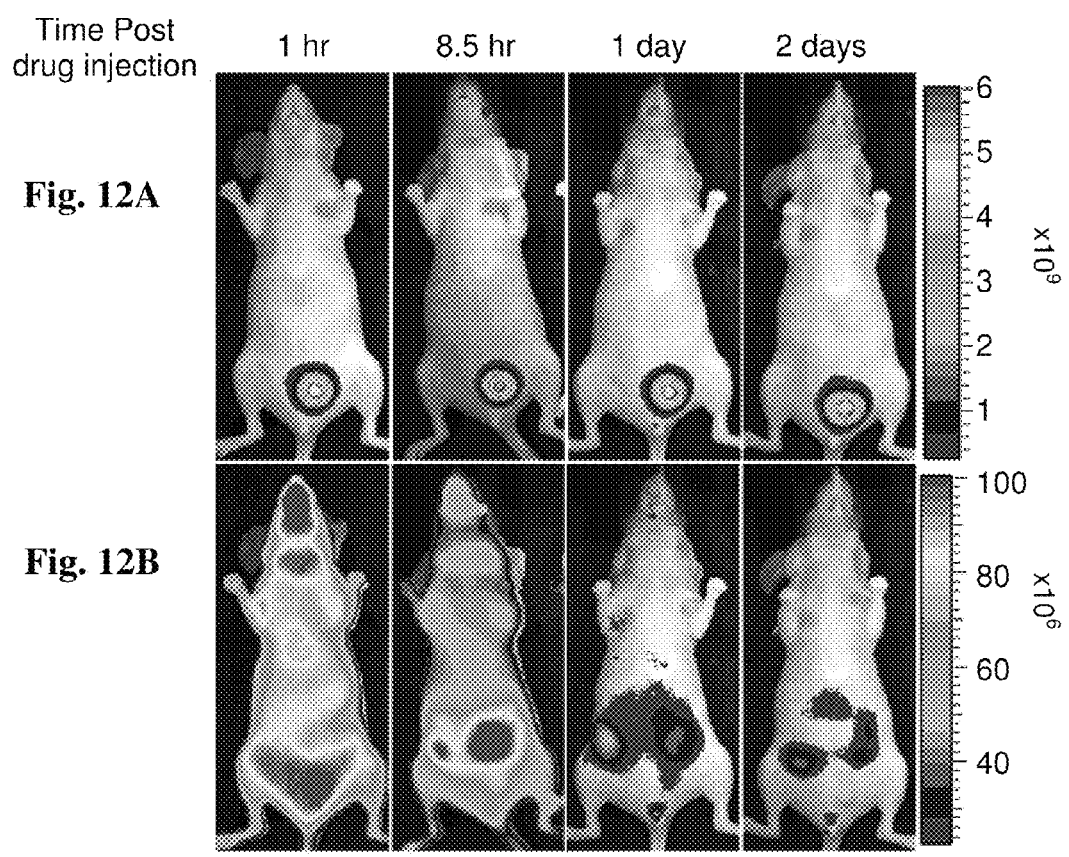

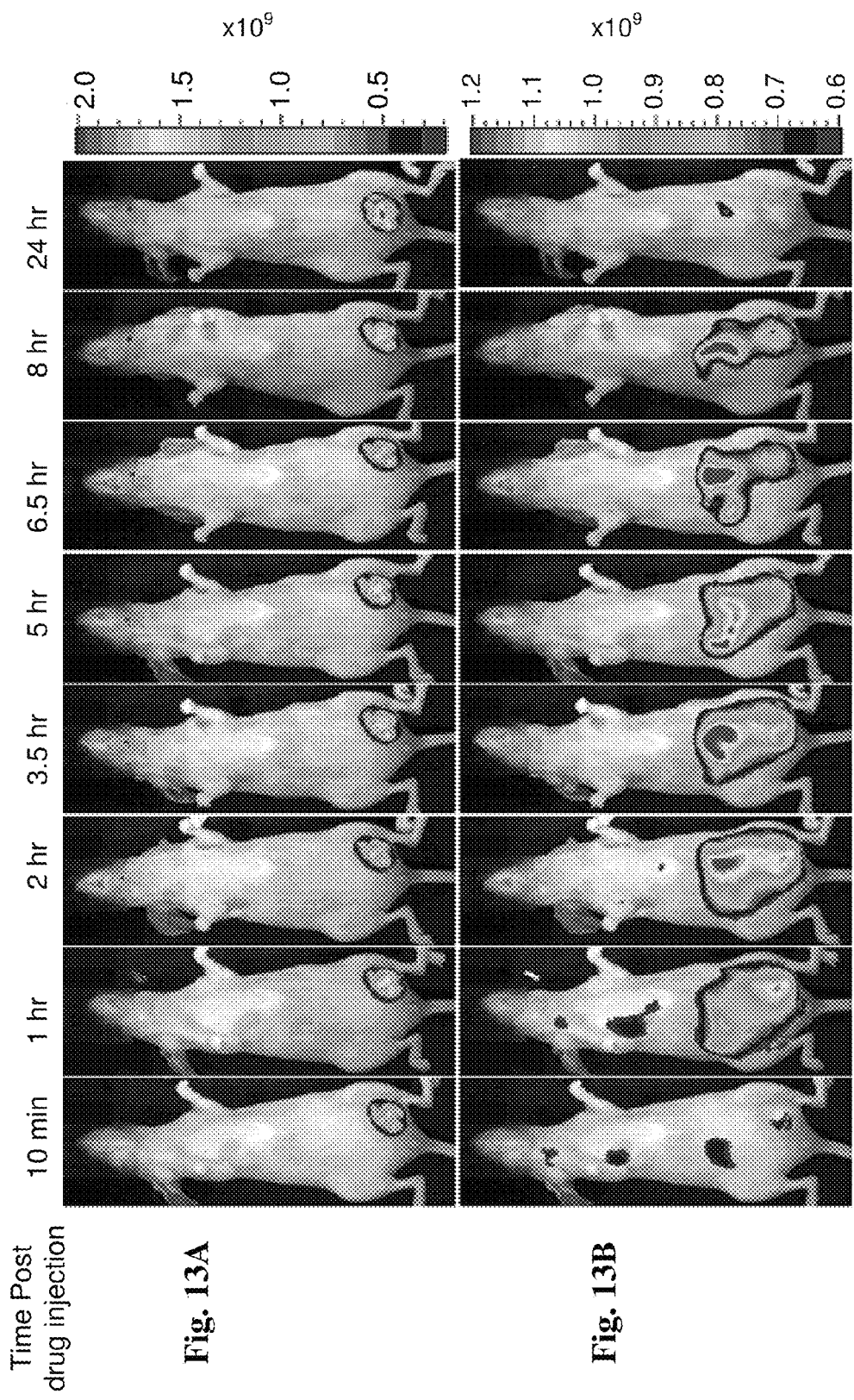

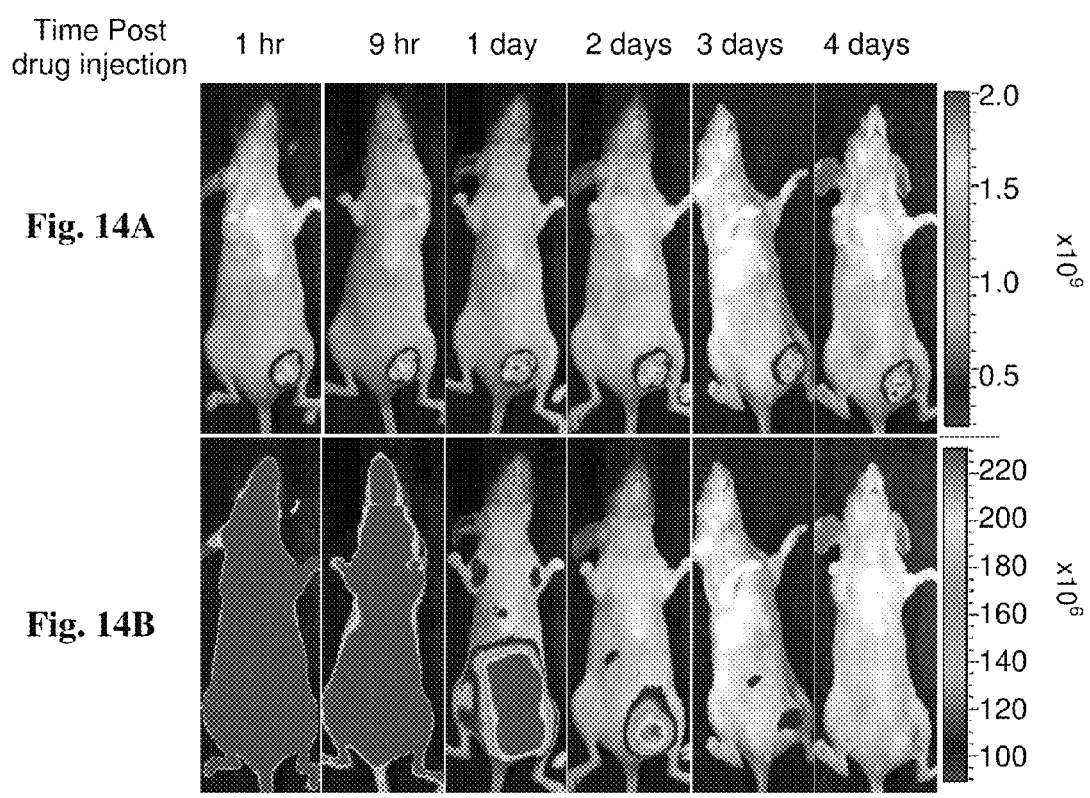

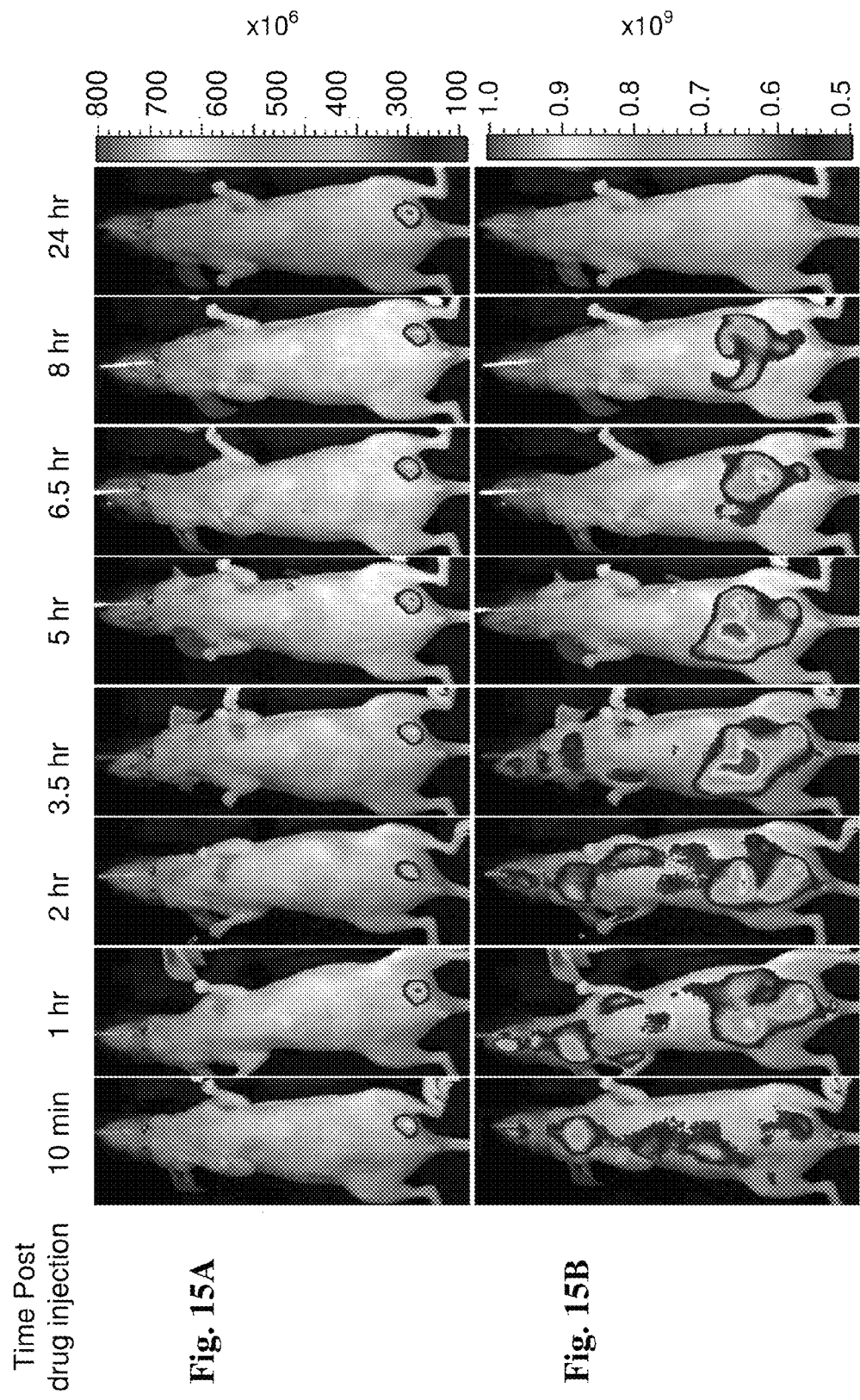

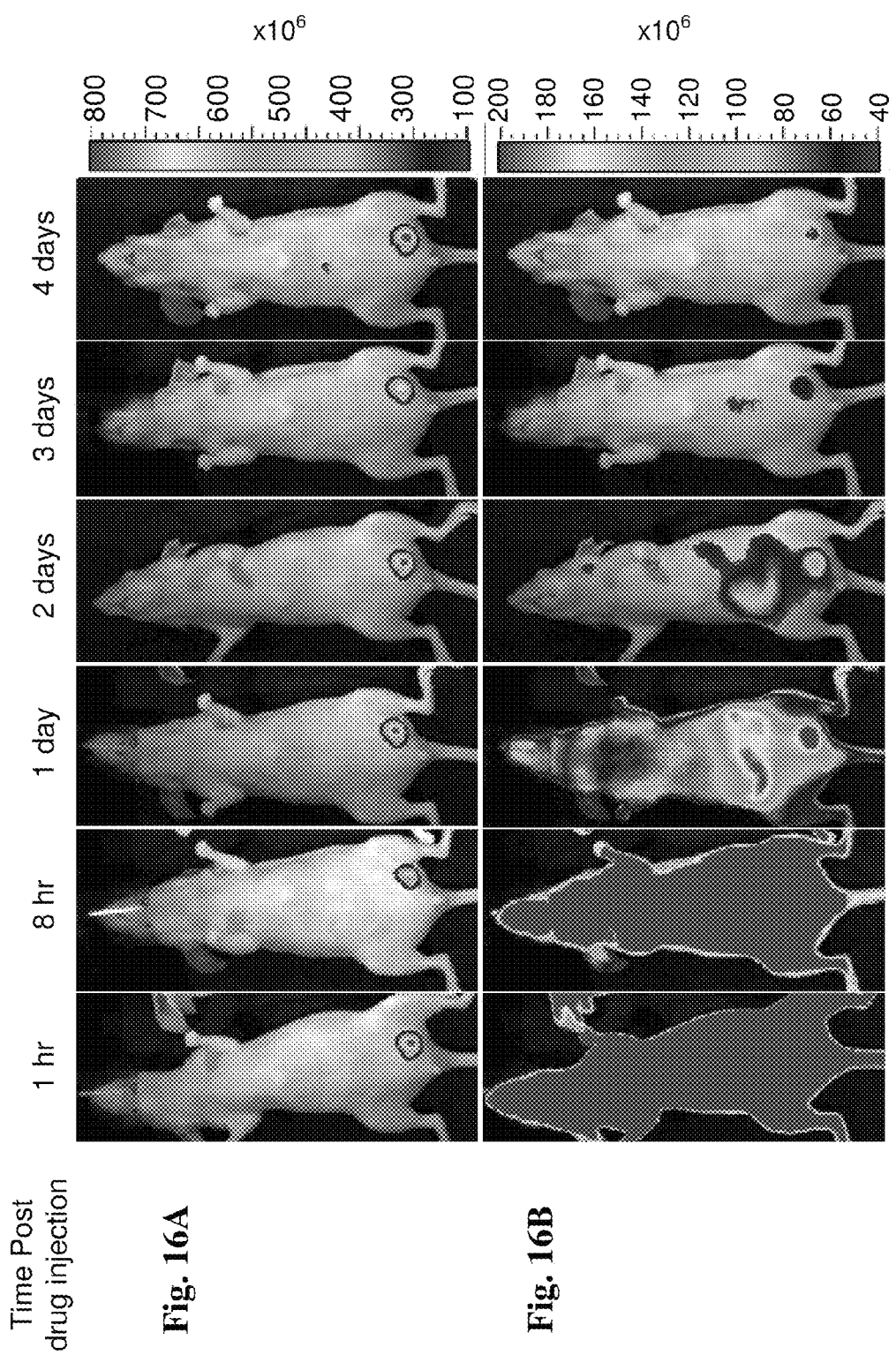

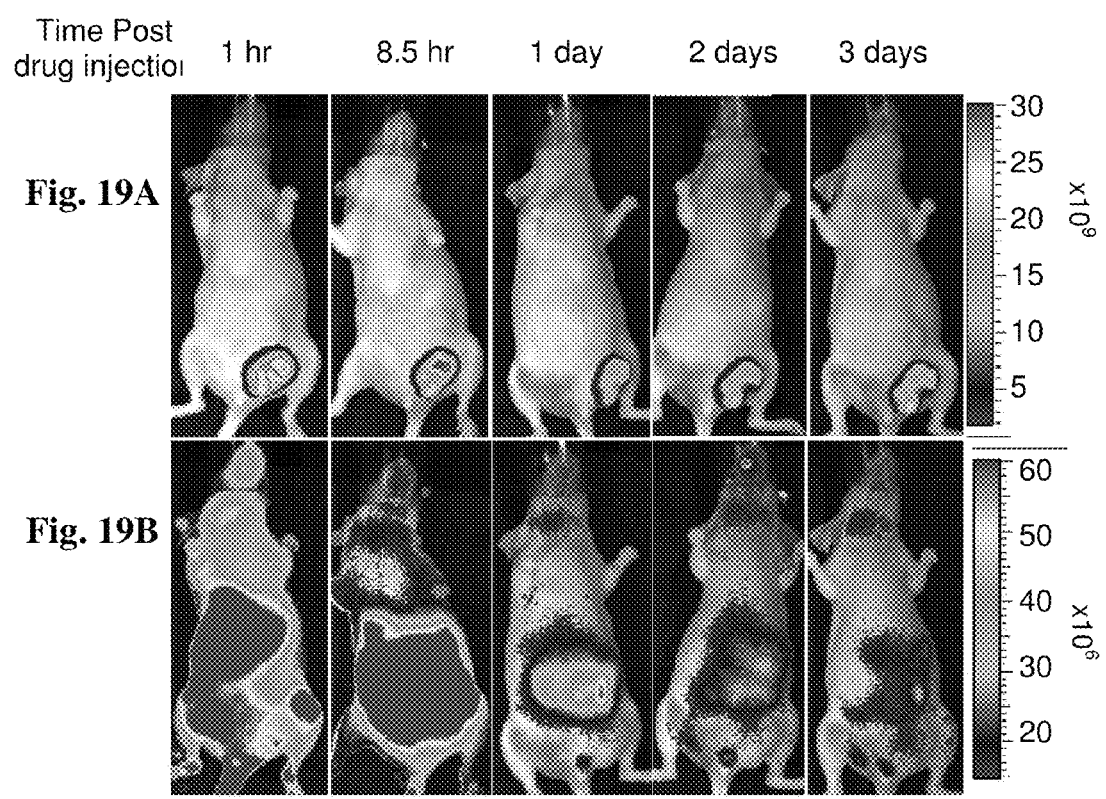

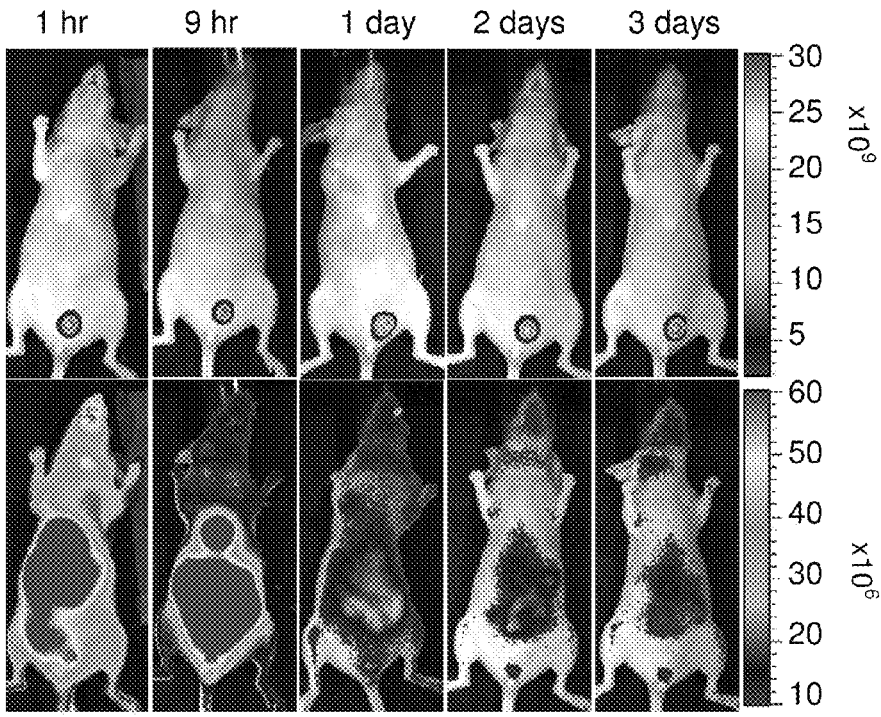

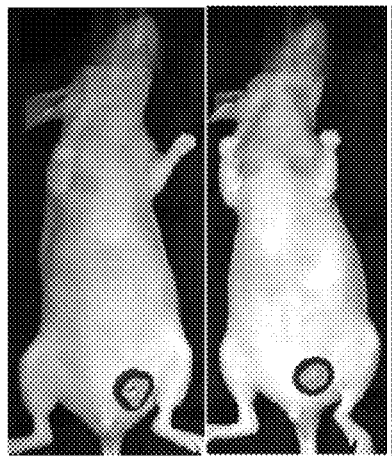 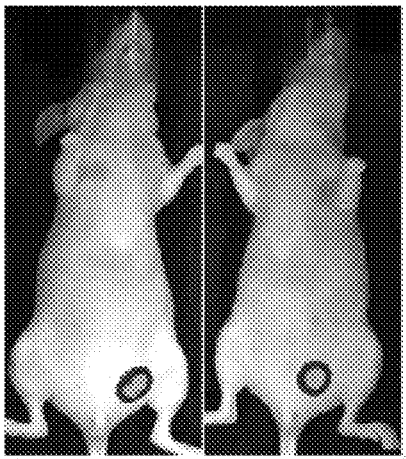 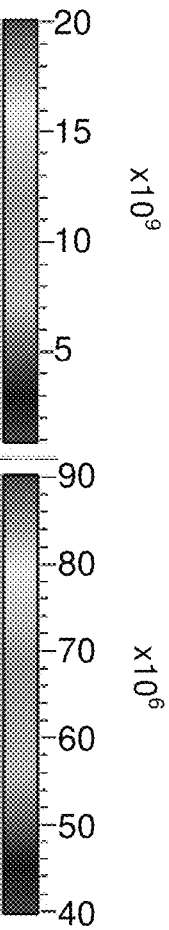  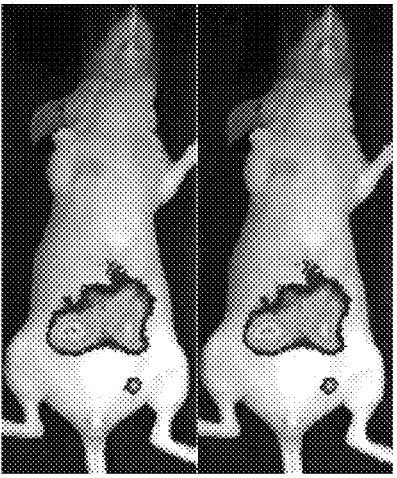
Fig. 22A  Fig. 22B
Fig. 22C  Fig. 22D Fig. 23A
Fig. 23B
Fig. 23C
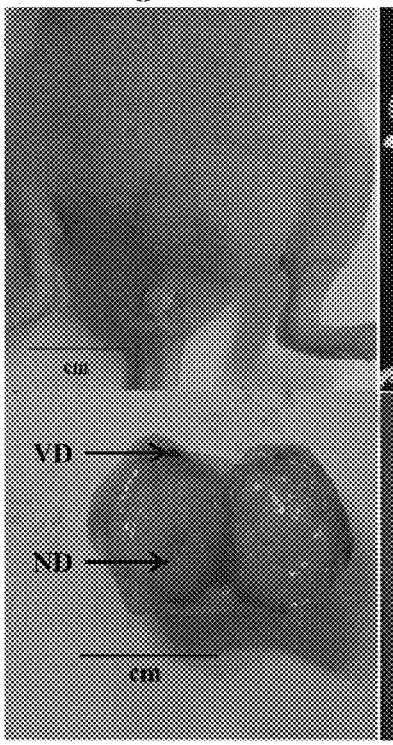
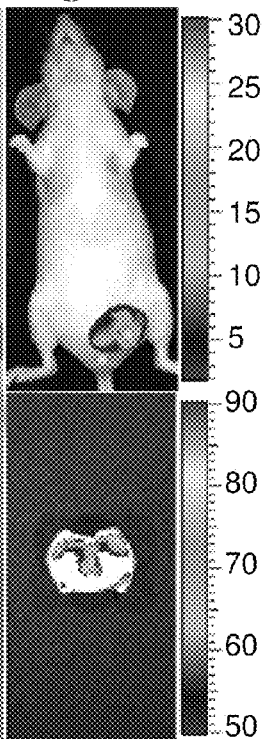
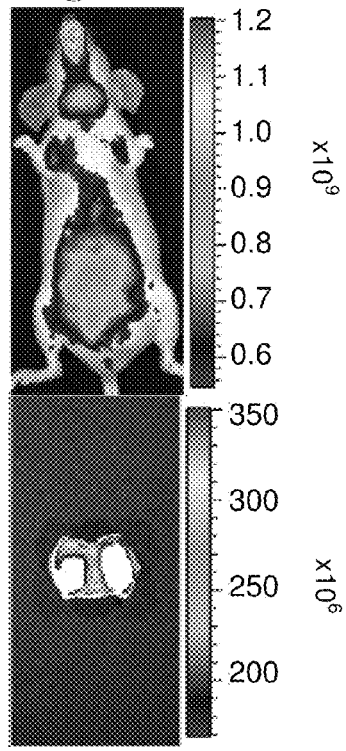
Fig. 23D
Fig. 23E
Fig. 23F Fig. 24A
Fig. 24B
Fig. 24C
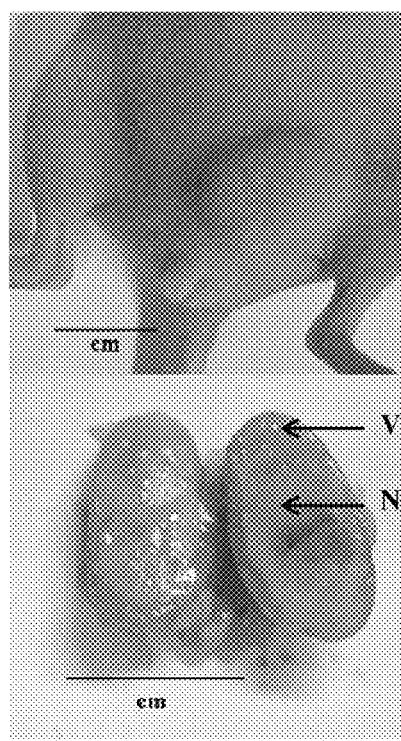
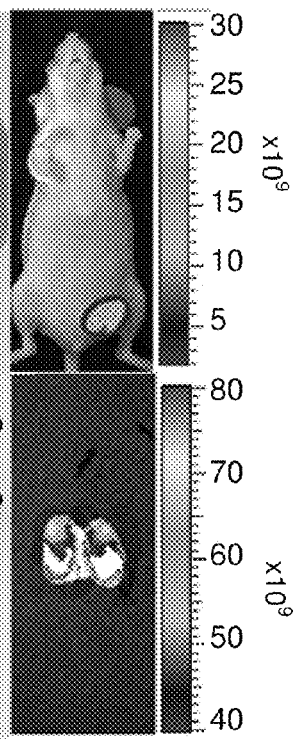
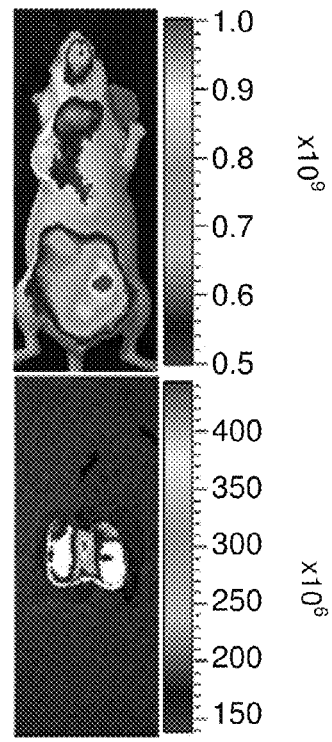
Fig. 24D
Fig. 24E
Fig. 24F Fig. 25A    Fig. 25B    Fig. 25C
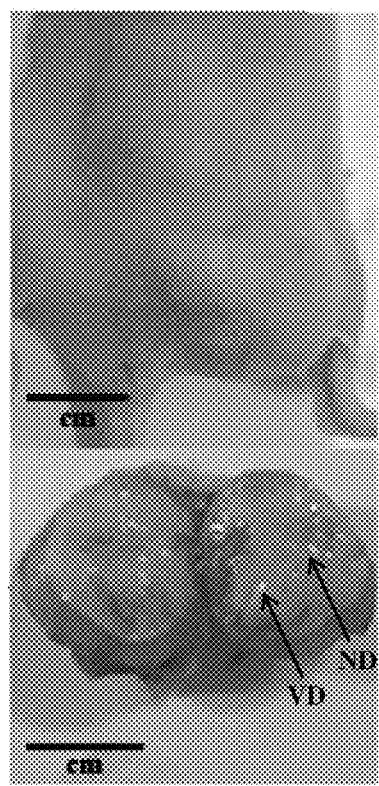
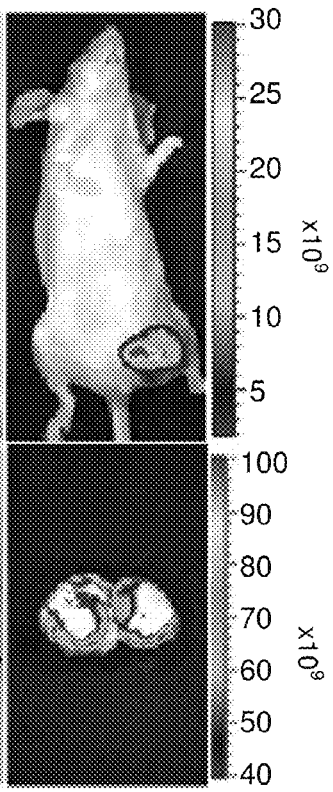
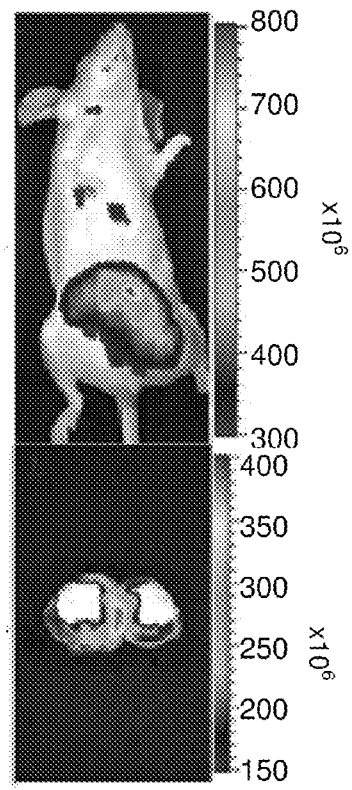
Fig. 25D    Fig. 25E    Fig. 25F Fig. 26A    Fig. 26B    Fig. 26C
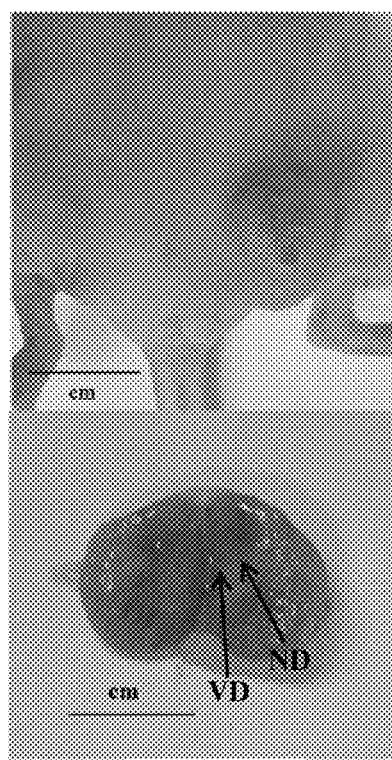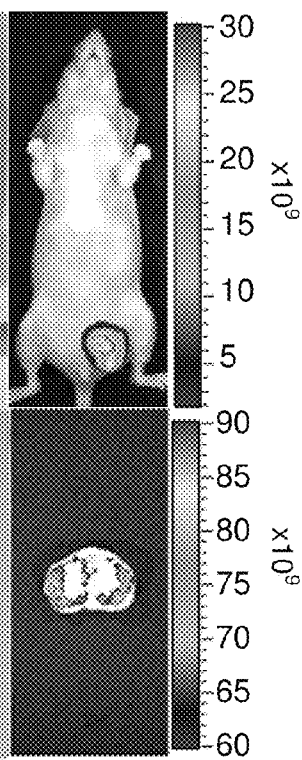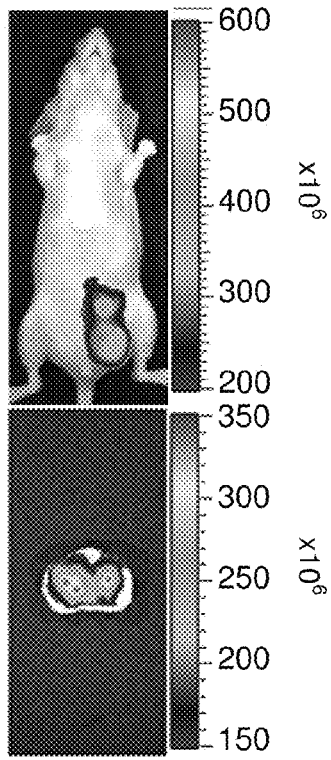
Fig. 26D    Fig. 26E    Fig. 26F Fig. 27A  Fig. 27B  Fig. 27C
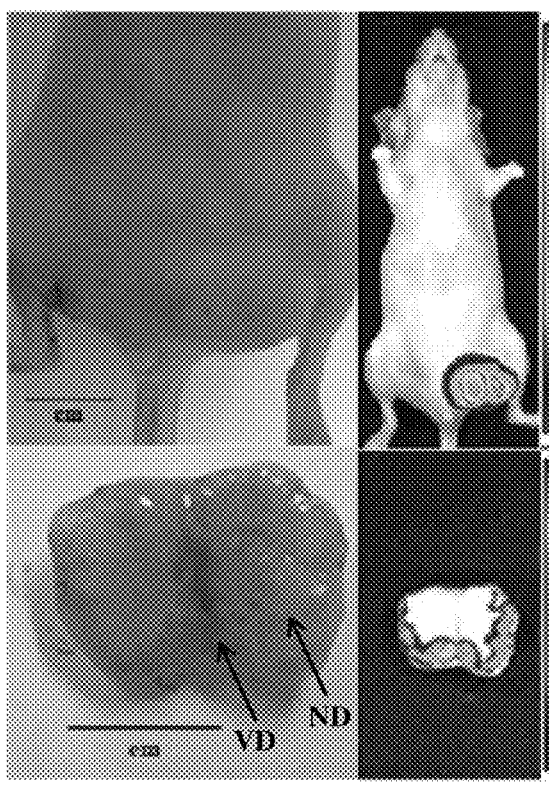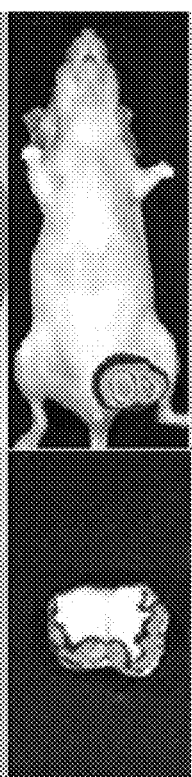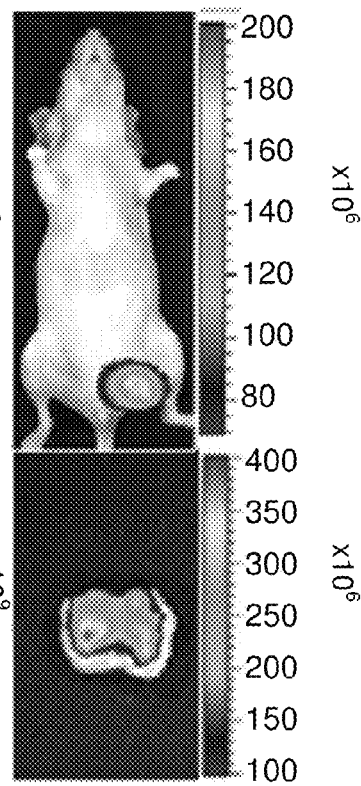
Fig. 27D  Fig. 27E  Fig. 27F Fig. 28A  Fig. 28B  Fig. 28C
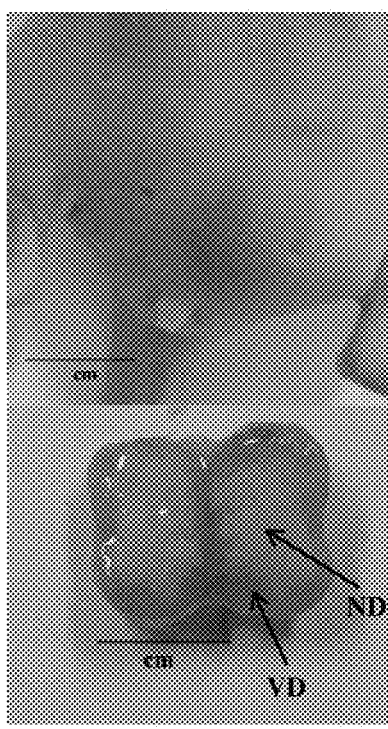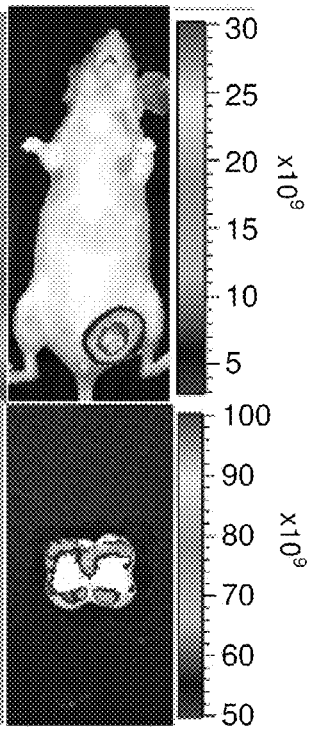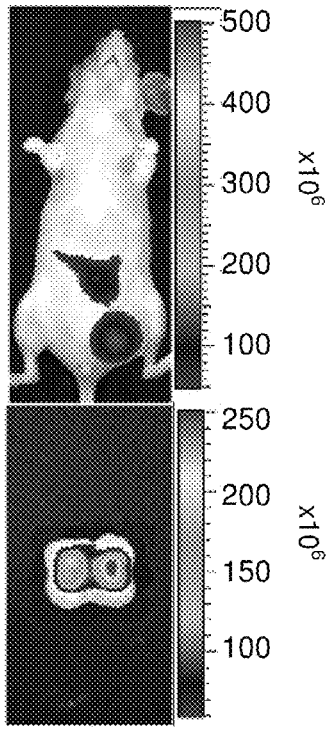
Fig. 28D  Fig. 28E  Fig. 28F Fig. 29A   Fig. 29B   Fig. 29C
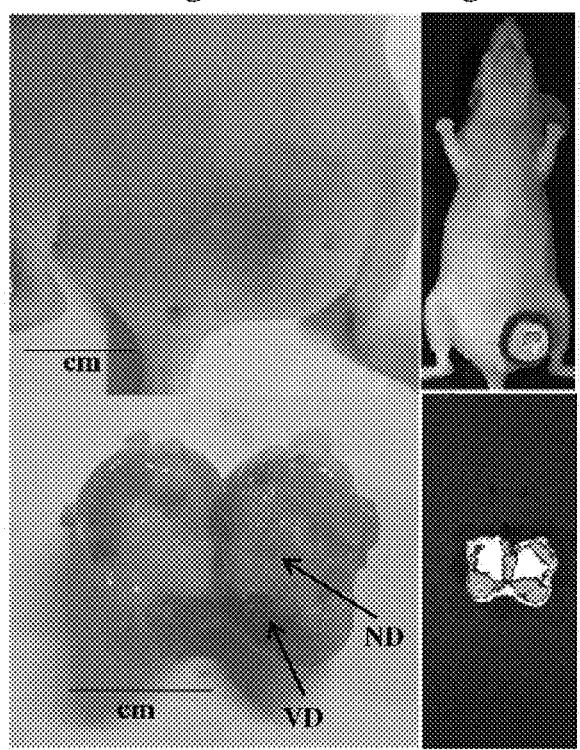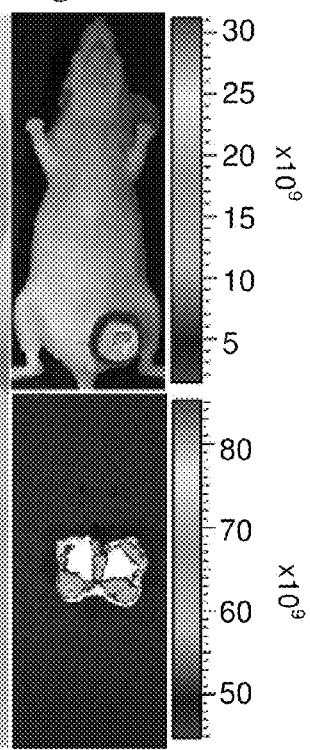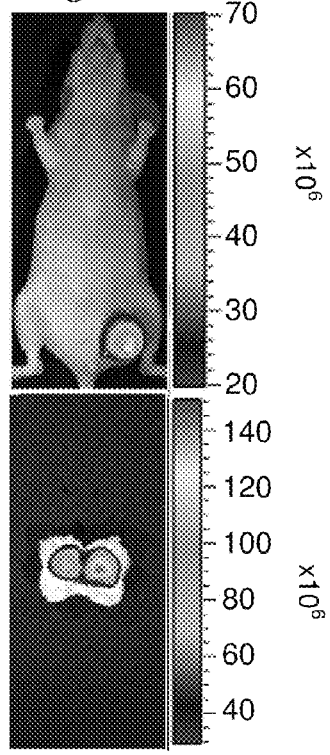
Fig. 29D   Fig. 29E   Fig. 29F

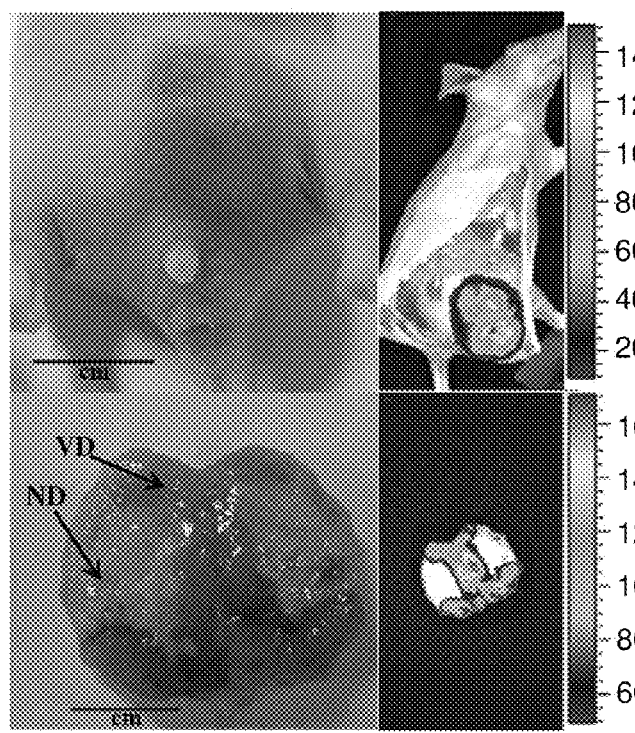 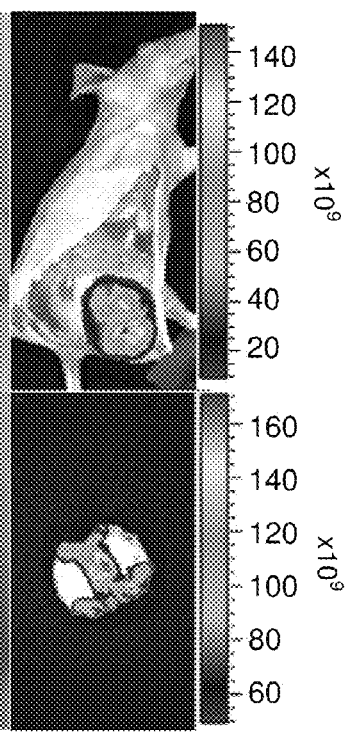 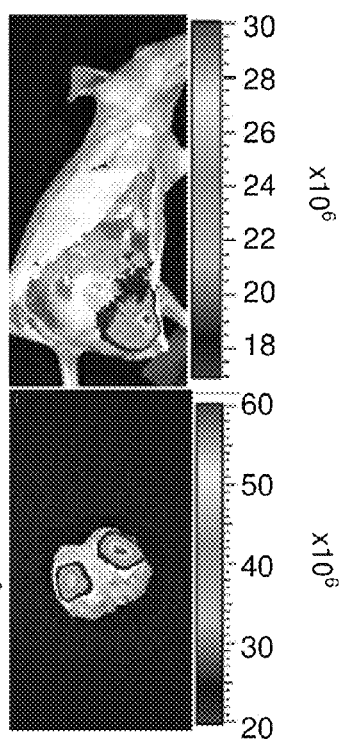
Fig. 30A  Fig. 30B  Fig. 30C
Fig. 30D  Fig. 30E  Fig. 30F Fig. 31A  Fig. 31B  Fig. 31C
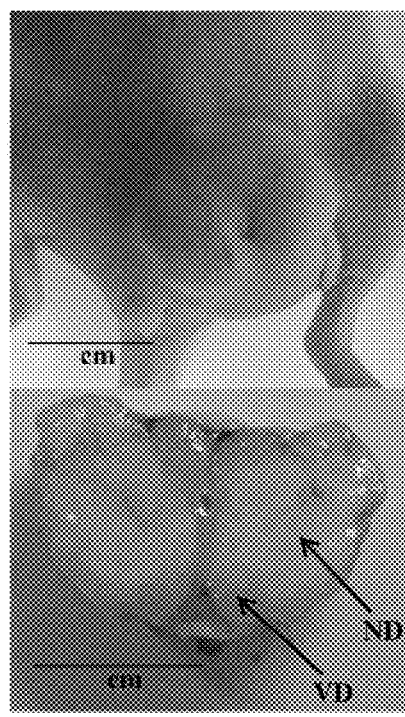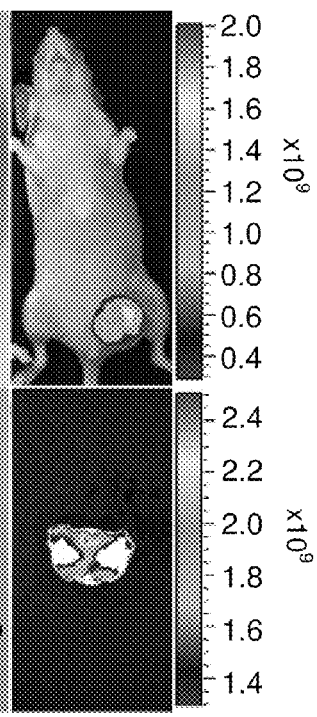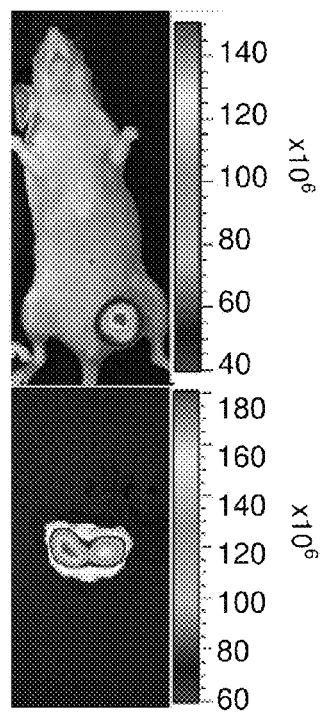
Fig. 31D  Fig. 31E  Fig. 31F

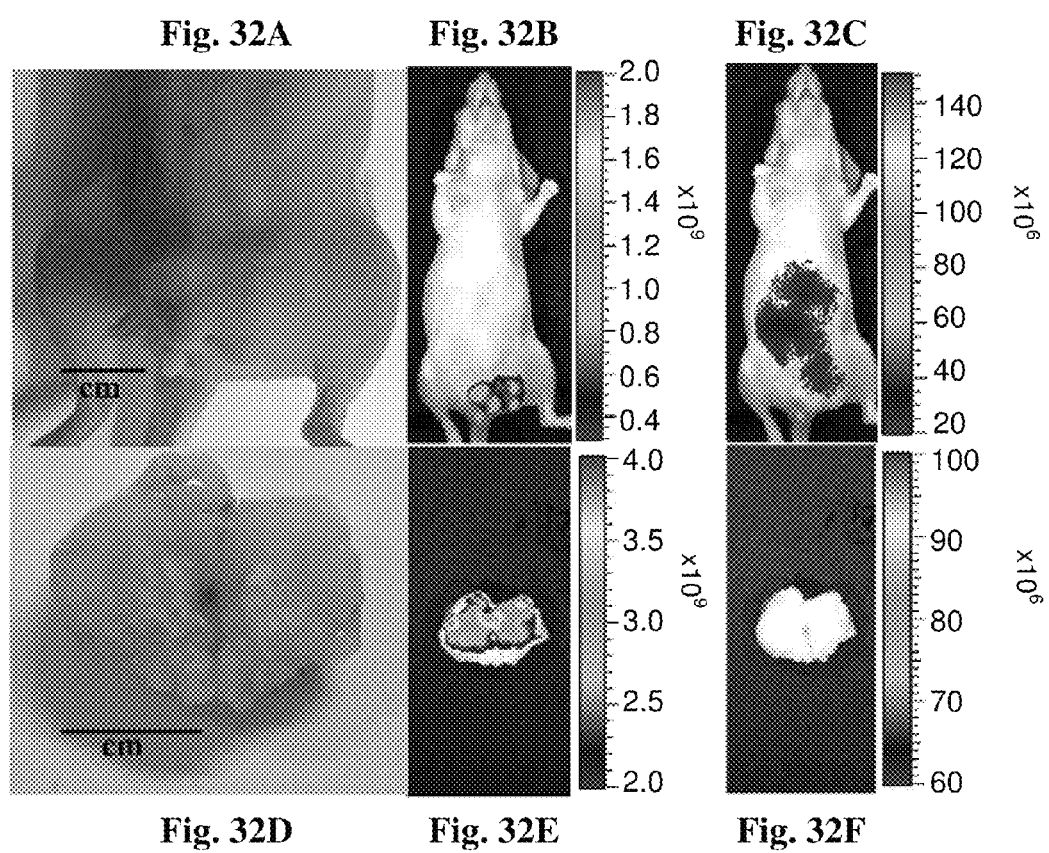

Fig. 33A  Fig. 33B  Fig. 33C  Fig. 33D
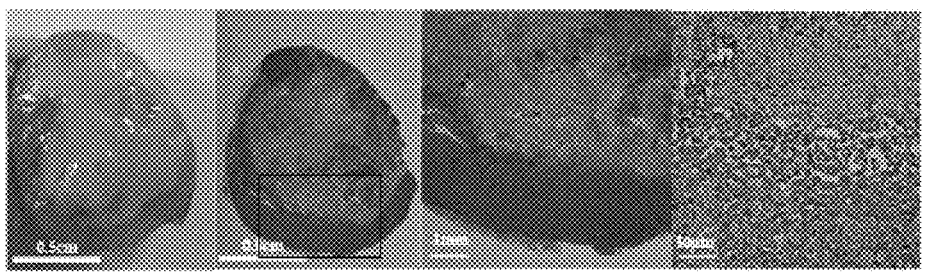
Fig. 34A  Fig. 34B
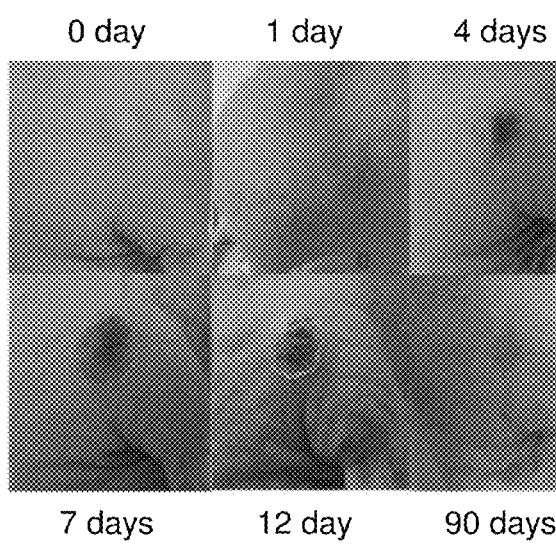 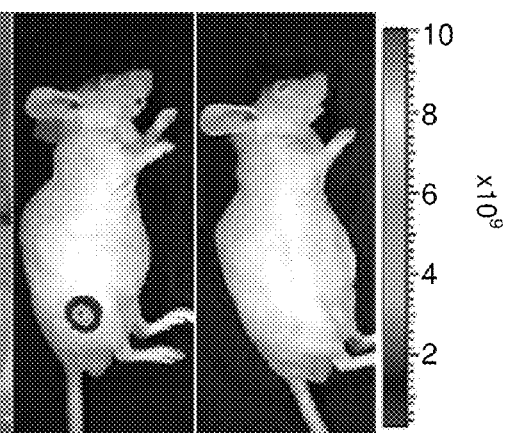

SEQUENCE LISTING

<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: Cyclic
<222> LOCATION: (1)..(5)
<220> FEATURE:
<221> NAME/KEY: D-AMINO ACID
<222> LOCATION: (4)..(4)

<400> SEQUENCE: 1

Arg Gly Asp Phe Lys
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: Cyclic
<222> LOCATION: (1)..(4)
<220> FEATURE:
<221> NAME/KEY: D-amino acid
<222> LOCATION: (3)..(3)

<400> SEQUENCE: 2

Arg Ala Phe Lys
1

<210> SEQ ID NO 3
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: Cyclic
<222> LOCATION: (1)..(4)

<400> SEQUENCE: 3

Arg Gly Asp Lys
1

<210> SEQ ID NO 4
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: CYCLIC
<222> LOCATION: (1)..(5)
<220> FEATURE:
<221> NAME/KEY: METHYLAMIDE
<222> LOCATION: (4)..(4)
<220> FEATURE:
<221> NAME/KEY: D-Amino acid
<222> LOCATION: (4)..(4)

<400> SEQUENCE: 4

Arg Gly Asp Phe Lys
1               5

```
<210> SEQ ID NO 5
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: CYCLIC
<222> LOCATION: (1)..(5)
<220> FEATURE:
<221> NAME/KEY: D-AMINO ACID
<222> LOCATION: (4)..(4)

<400> SEQUENCE: 5

Arg Gly Asp Tyr Lys
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: Linear
<222> LOCATION: (1)..(6)

<400> SEQUENCE: 6

Gly Arg Gly Asp Ser Pro
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: Linear
<222> LOCATION: (1)..(7)

<400> SEQUENCE: 7

Gly Arg Gly Asp Ser Pro Lys
1               5

<210> SEQ ID NO 8
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: Linear
<222> LOCATION: (1)..(25)

<400> SEQUENCE: 8

Gly Arg Gly Asp Ser Pro Gly Arg Gly Asp Ser Pro Gly Arg Gly Asp
1               5                   10                  15

Ser Pro Gly Arg Gly Asp Ser Pro Lys
            20                  25

<210> SEQ ID NO 9
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: CYCLIC
<222> LOCATION: (1)..(9)
```

```
<223> OTHER INFORMATION: disulfide bond Cys 1 - Cys9
<220> FEATURE:
<221> NAME/KEY: CYCLIC
<222> LOCATION: (3)..(7)
<223> OTHER INFORMATION: disulfide bond Cys 3 - Cys7

<400> SEQUENCE: 9

Cys Asp Cys Arg Gly Asp Cys Phe Cys
1               5
```

RGD-(BACTERIO)CHLOROPHYLL CONJUGATES FOR PHOTODYNAMIC THERAPY AND IMAGING OF NECROTIC TUMORS

TECHNICAL FIELD

The present invention is in the field of oncology and relates to detection of necrotic domains of tumors by tumor-targeting photodynamic imaging and treatment of said tumors by tumor-targeting photodynamic therapy using photosensitizers, particularly conjugates of chlorophyll and bacteriochlorophyll derivatives with peptides containing the RGD motif or RGD peptidomimetics.

DEFINITIONS AND ABBREVIATIONS

Bchl a: bacteriochlorophyll a: pentacyclic 7,8,17,18-tetrahydroporphyrin with a $5^{th}$ isocyclic ring, a central Mg atom, a phytyl or geranylgeranyl group at position $17^3$, a $COOCH_3$ group at position $13^2$, an H atom at position $13^2$, methyl groups at positions 2, 7, 12, 18, an acetyl group at position 3, and an ethyl group at position 8, herein compound 1; Bphe: bacteriopheophytin a (Bchl in which the central Mg is replaced by two H atoms); Bpheid: bacteriopheophorbide a (the $C-17^2$-free carboxylic acid derived from Bphe without the central metal atom); Chl: chlorophyll; Rhodobacteriochlorin: tetracyclic 7,8,17,18-tetrahydroporphyrin having a —$CH_2CH_2COOH$ group at position 17, a —COOH at position 13, methyl groups at positions 2, 7, 12, 8, and ethyl groups at positions 3 and 8; Pd-Bpheid: Pd-bacteriopheophorbide a; EC: endothelial cells; ECM: extracellular matrix; NIR: near-infrared; PDT: photodynamic therapy; RGD-4C: the cyclic nonapeptide $CDCRGDCFC-NH_2$; ROS: reactive oxygen species.

IUPAC numbering of the bacteriochlorophyll derivatives is used throughout the specification. Using this nomenclature, the natural bacteriochlorophylls carry two carboxylic acid esters at positions $13^2$ and $17^2$, however they are esterified at positions $13^3$ and $17^3$.

BACKGROUND ART

Necrosis and hypoxia of primary and metastatic tumors have been strongly correlated with tumor aggressiveness and poor prognosis in cancer patients. Solid tumors that reach a certain size, out grow their oxygen supply and become hypoxic and eventually necrotic. In tumor areas positioned more than 70 μm from nutritive blood vessel the interstitial oxygen pressure decreases and past a distance of 150-180 μm the cells become nearly anoxic (Vaupel et al. 2001). It is believed that necrosis is the result of chronic ischemia that is caused by vascular collapse and rapid tumor cell growth that is higher than the rate of angiogenesis (Leek et al. 1999).

Necrotic areas in solid tumors undergo morphological modifications. At the beginning the original structure is basically preserved, and necrotic cells keep their overall shape but become highly eosinophilic. After some time, this pattern is replaced by liquefaction necrosis, in which the cellular structures are broken down (Leek et al. 1999).

Both necrosis and hypoxia are well established as indicators for poor prognosis. In transitional cell carcinoma of the upper urinary tract, malignant mesothelioma and renal cell carcinoma (RCC), necrosis was suggested as an independent predictor of the cancer outcome and as a very powerful tool for prognostic purposes (Edwards et al. 2003; Sengupta et al. 2005; Lee et al. 2007).

In invasive carcinoma of the breast, necrosis was correlated with high vascular density and angiogenesis, high levels of focal macrophage infiltration and decreased patient survival (Kato et al. 1997; Lee et al. 1997; Leek et al. 1999; Tomes et al. 2003). Central necrosis, which is a common feature of invasive breast cancer, was associated with poor outcome and tumor aggression. Macrophages were shown to be attracted to the necrotic tumors by chemotactic factors, released by hypoxic or dying tumor cells (Leek et al. 1999). Large necrotic areas in the ductal lumen were observed in the comedo (invasive) ductal carcinoma in situ (DCIS) as opposed to the non-comedo (non-invasive) DCIS (Cutuli et al. 2002). Necrosis and hypoxia at the center of DCIS lesions with up to 360 μm diameter, showed a marked biological difference in the nature and behavior of the neoplastic cells. Thus the presence or absence of necrosis in ducts was found to be a feasible criterion for DCIS classification (Bussolati et al. 2000).

Necrosis in the majority of this type of tumors was shown to associate with hypoxia (Tomes et al. 2003). Hypoxia and anoxia subject the tumor cells to oxidative stress. Prolonged hypoxic conditions were shown to increase the rate of mutations, to accelerate the progression of the tumor, to increase angiogenesis and metastatic potential and to activate growth promoting signaling pathways. Adaptation to oxidative stress often makes the tumor cells resistant to certain therapeutic modalities (Brown et al., 2001).

The correlation between necrosis and hypoxia is very well established, however there might be hypoxic conditions that have not reached necrosis, or necrosis that does not necessarily reflects acute or severe hypoxia (Dewhirst 1998). There are several marker genes for hypoxia, among them: hypoxia induced factor 1 (HIF1), glucose transporter 1 and carbonic anhydrase IX. Only detection of all three markers assures the classification of necrosis (Tomes et al. 2003), making the identification of an area as necrotic by gene expression quite complicated.

Necrotic and hypoxic conditions are known to create a major problem in cancer therapy. Hypoxic tumor domains are relatively resistant to radiation treatment since there is a poor promotion of the radiation assault and since stem cells that may eventually be present in the tumor volume do not respond well to the treatment, resulting in tumor re-growth (Brown et al., 1998; Dean et al., 2005). Since most chemotherapeutic reagents impose cell death due to interactions with cycling cells, cell arrest because of hypoxia results in resistance to conventional chemotherapy, leaving non-proliferating or slow proliferating cells unharmed (Tannock, 1978). Furthermore, hypoxic conditions usually create an acidic environment that might change the nature of the drug, making it less active (Tannock et al., 1989).

One of the more problematic aspects of solid tumors chemotherapy involves the trafficking of therapeutic agents into the tumors and especially to hypoxic and necrotic domains. Tumors usually contain irregular and leaky microvessels with heterogeneous blood flow and large intervessel distances. These features, in addition to the absence of proper lymphatic drainage and high interstitial pressures, make diffusion the most important mechanism of extravascular transport of nutrients and drugs in tumors. However, because of the non-regular vascularisation, many of the tumor cells are at higher distances from capillaries than cells in the normal tissues, reflected in having insufficient concentrations of antitumor agents at the cell sites. Moreover, the enhanced interstitial fluid pressure due to the lack of lymphatic drainage reduces the convection uptake and further inhibits the distribution of drugs into the tumor cells, particularly that of macromolecules (Minchinton et al., 2006).

Thus, the ability to detect hypoxic and necrotic areas within tumors in-vivo is of utmost importance. Knowledge of hypoxic tumor domains might help choosing the right treatment—either by improving tumor oxygenation before or during treatment or by using strategies that exploit the hypoxia (Weinmann et al., 2004). Using this approach, application of hypoxia-activated cytotoxins such as 2-cyclopropyl-indoloquinones, AQ4N, Tirapazamine (TPZ) and PR-104 may help improve the treatment outcome (Brown et al., 2004; Lee et al., 2007; Patterson et al. 2007).

Histopathology and immunohistochemistry are commonly used for identification of necrosis and hypoxia; however, they are invasive and do not enable detecting in situ. In situ methods include magnetic resonance imaging (MRI) (Kamel et al. 2003; Metz et al. 2003), blood oxygenation level dependent-MRI (Kennan et al. 1997), positron emission tomography (PET) (Lehtio et al. 2004) and diffusion-weighted MRI (Lang et al. 1998).

Necrosis-avid contrast agents (NACAs) for MRI can be classified into porphyrin-based and non-porphyrin-based agents. One of the most known porphyrin-based NACAs is gadophrin-2 that shows specific necrosis accumulation mostly at the margins of the necrotic area. The mechanism of accumulation was suggested to be based on serum albumin (SA) trafficking, but recent studies doubted this approach (Hofmann et al. 1999; Ni et al. 2005)

Most malignant cells cannot grow to a clinically detectable tumor mass in the absence of blood vessels. That is why tumors reaching a certain size (approximately 2-3 mm$^3$) have to switch to an angiogenic phenotype to support their growth. The switch to an angiogenic phenotype may represent an imbalanced expression of angiogenic factors and angiogenesis inhibitors. Overexpression of angiogenic factors and down-regulation of angiogenesis inhibitors are both necessary and sufficient to induce new blood vessels growth, and these two processes usually occur simultaneously to switch on tumor angiogenesis (Cao 2005).

The biochemical features that signify blood vessels in tumors may include angiogenesis-related molecules such as certain integrins. The integrin family of cell-adhesion receptors comprises distinct 24 αβ heterodimers that recognize glycoprotein ligands in the extracellular matrix or on cell surfaces. Many members of the integrin family, including α5β1, α8β1, αIIbβ3, αVβ3, αVβ5, αVβ6 and αVβ8, recognize an Arg-Gly-Asp (RGD) motif within their ligands. These ligands include fibronectin, fibrinogen, vitronectin, von Willebrand factor and many other large glycoproteins (Takagi 2004). Hence, molecules containing RGD motif have been suggested to provide new opportunities for selective up-take and subsequently imaging and detection of primary tumor lesions, necrotic areas and targeted therapies. This field of research is getting increased attention. There are many reports of using RGD-labeled components for imaging (Temming et al. 2005). The major drawback reported in the literature is the insufficient concentration of the reporting element at the site of tumors under 4-5 mm. That is why the use of RGD-targeted imaging was mainly restricted to PET-scan, which is a more sensitive method.

Understanding tumor growth, metastases formation, tumor-host interaction and angiogenesis requires tumor models that allow easy tracking of tumor cells even at their individual level. Previous methods used for the direct measurement of most meaningful biological parameters of tumors have only been achievable via invasive end-point procedures (Lyons 2005). The majority of such methods involves histopathological examination or immunohistochemistry which are slow, invasive and not always sensitive approaches (Yang et al. 2000). Therefore, it was necessary to introduce new methods that enable direct visualization of tumor tissues, are non-invasive and enable measurement of tumor relevant parameters at both the cellular and molecular level.

In recent years several non-invasive methods have been developed: MRI and spectroscopy, PET, single photon emission computed tomography and computed tomography (Lyons 2005).

There are several imaging methods that are transgene-based. These methods enable the non-invasive measurement of a wide range of biological parameters with excellent tumor specificity, whole body imaging in live model animals and detection of metastases. Two of these methods are: bioluminescence imaging and fluorescence imaging.

Optical bioluminescence is based on three components: the enzyme luciferase, the substrate luciferin and adenosinetriphosphate (ATP). In this method, no light excitation is required to generate light emission. However, if one of these components is absent no detection is possible. The method enables monitoring cell viability or cell function at a high throughput because of the good signal/noise value (Lyons 2005). The main disadvantages of the luciferase/luciferin method are the low anatomic and image resolutions thus requiring a substantial amount of time to collect sufficient photons to form an image from an anesthetized animal. Moreover, increased tissue depth and the need for exogenous delivery of the substrate attenuate the in-vivo light emission (Yang et al., 2000; Lyons, 2005). Additionally, ex-vivo experiments are difficult to perform since ATP is required for the enzyme activity. Importantly, the method involves subjective parameterization that reduces its quantitative value.

Another way for monitoring tumor progression by optical fluorescence imaging is based on transfecting tumor cells with a stable fluorescent protein such as green fluorescent protein (GFP) and red fluorescent protein (RFP). In this method there is need for external excitation before emission can be detected. The main disadvantages of this method are that (1) the excitation and emission lights are prone to attenuation with increased tissue depth and (2) the autofluorescence of non labeled cells increases noise (Lyons, 2005). The main advantages include: multiple reporter wavelengths enabling multiplex imaging; high compatibility with a range of ex-vivo approaches for analytic methods such as fresh tissue analysis; there is no need for preparative procedures for imaging which makes it uniquely suited for visualizing in live tissue; the method is external and noninvasive; the method provides a real-time fluorescence optical imaging of internally growing tumors and metastases in transplanted animals that can give a whole-body image but also the image of single cells extracted from the primary lesion and metastases (Yang et al., 2000; Lyons, 2005). Whole body imaging is one of the most required tools for understanding tumor development. Thus, by genetically labeling of tumor cells with GFP or RFP, external whole body imaging of primary and metastatic tumors can be achieved (Yang et al. 2000).

Fluorescence tagging is suitable for in-vivo, fresh tissue and in-vitro detection. Using tumor cells expressing fluorescent proteins enables the imaging of live animals and the follow up of tumor progression in different time points. The RFP has a longer wavelength emission than GFP thus enabling higher sensitivity and resolution of microscopic tumor growth (GFP excitation wavelength—489 nm, emission wave-length—508 nm, RFP excitation wavelength—558 nm, emission wave-length—583 nm).

Ductal carcinoma in situ (DCIS) comprises a clonal proliferation of cells that appear malignant and accumulate within the lumen of the mammary ducts with no evidence of invasion into the adjacent breast stroma and beyond the epithelial basement membrane. There is a significant chance of transforming non-invasive DCIS lesions into an invasive, life-threatening disease if it is not treated at an early stage. Following the wide-spreading use of mammography, there has been a dramatic increase in the number of patients diagnosed with DCIS at the early stage and the recommended treatment modality has accordingly shifted from mastectomy (with close to 100% cure rate) toward breast conserving (BC) surgery (BCS), e.g. lumpectomy or minimally invasive breast surgery (Kepple et al., 2004), optionally accompanied by RT and adjuvant endocrine therapies. However, recurrence rates following BCS, both ipsilaterally (same breast) or contralaterally (other breast), even when accompanied by RT, were recently found to be significantly higher than after mastectomy, particularly for patients at the age of ≤40 (regression rate of 25-35%; Bijker N et al., 2006; Cutuli et al., 2002) Furthermore, multifocal lesions pose a difficulty for partial dissection and the same is true for persistently involved margins that were found critical to complete tumor regression (Cellini et al., 2005). Additionally, the physical and psychological burden and the possible cosmetic outcomes of lumpectomy followed by RT are significant. These drawbacks make the treatment and management of DCIS today controversial issues in breast cancer therapy and have stimulated the search for new and/or complementary modalities of treatment and prognosis.

DCIS is a biologically heterogeneous form of malignancy with a diverse clinical presentation, histology, cellular features, and biological potential. It has been classified into comedo (invasive) and non-comedo (non-invasive) carcinomas, where comedo has the higher grade, with a potentially more invasive subtype, characteristically containing a large necrotic area in the ductal lumen and cells with marked cytologic atypia. About two-thirds of the patients with low to intermediate grade DCIS are expected to have a multifocal, ipsilateral disease with gaps that may reach 1 cm between different foci (Cutuli et al., 2002). High-grade lesions tend to be continuous with gaps smaller than 5 mm (Cellini et al., 2005).

The natural development of non-invasive DCIS into an invasive breast tumor may take 15-20 years and involve 14 to 60 percent of the diagnosed women (Burstein et al., 2004). In fact, DCIS appears to represent a stage of breast cancer development in which many of the molecular events that define invasive breast cancer are already present (Cutuli et al., 2002; Holland et al., 1990). Specifically, ~30% of low-grade lesions will develop into invasive carcinoma if left untreated (Sanders et al., 2005). Lesions with a diameter greater than 2.5 cm are frequently accompanied by occult microinvasive tumors that may not exceed 0.1 mm. The involvement of tumor margins provides an important prognostic marker. Close to excision (less than 1 mm) or positive margins, high-grade and/or comedo necrotic areas are associated with greater risk for recurrence.

Like in many other cancers, new blood vessel formation (angiogenesis) in breast cancer plays a central role in both local tumor progression and the development of distant metastasis (Boehm-Viswanathan, 2000; Kieran et al., 2003). Significantly higher microvessel density (MVD) was found in the DCIS tissue compared with the surrounding normal tissue (Guidi et al., 1994; Guidi et al., 1997; Guinebretière et al., 1994). Fibrocystic lesions with the highest vascular density are associated with a greater risk of breast cancer (Guidi et al., 1994; Guidi et al., 1997; Guinebretière et al., 1994). Histopathological examinations of aggressive DCIS lesions were associated with increased MVD and vascular endothelial growth factor (VEGF) expression (Guidi et al., 1997; Schneider et al., 2005). Clinicopathologic correlations also confirm the cardinal role of angiogenesis in the progression of breast cancer, making it attractive target for DCIS therapy and prognosis (Folkman, 1997; Krippl et al., 2003; Relf et al., 1997). Vessel cooption, growth by intussusception (Patan et al., 1996), vascular mimicry and vasculogenesis are naturally occurring processes that may decrease the tumor's dependence on classical angiogenesis. Of particular importance is the finding that inflammatory breast cancer depends almost entirely on vasculogenesis, apparently because of the inability of the cancer cells to bind endothelial cells.

The critical dependence of DCIS on a highly dense vascular bed has made antiangiogenic (inhibiting the formation of new blood vessels) and antivascular (occlusion/destruction of existing blood vessels) therapies (Shimizu et al., 2005; Thorpe, 2004) attractive options for localized BC therapy (Schneider et al., 2005; Folkman, 1996). Indeed, antiangiogenic drugs such as bevacizumab (an anti-VEGF-A receptor antibody) and SU011248 (an inhibitor of VEGF receptor tyrosine) are in phase II clinical trials. Interestingly, tamoxifen was also found to possess antiangiogenic activity. Yet, a growing body of evidence indicates deficiencies in the antiangiogenic approach. These include the need for a chronic treatment, the partial failure of the "resistance to resistance theory" (Schneider et al., 2005; Streubel et al., 2004) and pharmacokinetic resistance. Following these hurdles, the antivascular approach presently appears more promising, expected to result in eradication of the entire tumor with no need for chronic treatment (Folkman, 2004) A recently emerging, promising avenue for vascular-targeted treatment is by photodynamic therapy (VTP).

Likewise, targeting paramagnetic metals with appropriate relaxivity, positron emitting chemical entities (e.g. $^{64}Cu$), or fluorescence probes to the dense vascular bed of DCIS, should open new avenues for the detection of the related lesions, margins definition and prognosis as explained below. Fluorescence detection of breast cancer lesions was shown useful for up to 10 mm depth (Britton, 2006). Dynamic MRI with Gd as a contrast agent is based on enhanced leakiness of the tumor vasculature and currently used for tumor localization in the breast (Rankin, 2000). However, the current use of MRI is limited by the available short integration time of contrast agents that shortly reside but do not selectively taken up by the tumor tissue.

Photodynamic therapy (PDT) generates a burst of cytotoxic reactive oxygen species (ROS) at a selected treatment site. Because of their short lifetime, the ROS toxicity is confined to the illuminated site. PDT typically consists of five steps: 1. Intravenously (IV) administration of a photosensitizer; 2. A time period that enables a desirable concentration of photosensitizers to reach the target tissue; 3. Illumination of the target tissue transcutaneously or interstitially with high intensity laser light (up to 1 W for continuous illumination) via thin (0.4 mm diameter or less) optical fibers for deep tissue illumination with the consequent local generation of cytotoxic ROS; 4. Development of tumor necrosis and tumor eradication; 5. Tissue remodeling and healing.

Vascular-targeted PDT (VTP) aims at ROS generation within the blood vessels of the treated tissue that can be accomplished either by tissue illumination immediately after sensitizer's administration or by using sensitizers that do not extravasate from the circulation. Several generations of bacteriochlorophyll sensitizers termed herein "Bchl derivatives"

or "BchlD" have been developed in our laboratory. The synthesized compounds (Rosenbach-Belkin et al., 1996; U.S. Pat. No. 5,650,292) possess a very strong absorption in the NIR (750-765 nm) enabling deep light penetration into the subject tissues, assuring a treatment diameter of up to 4 cm around a cylindrical fiber at high fluence rates (20 mW-1 W). Upon illumination, a local high concentration of ROS (OH. and $O_2^-$ radicals) is generated in the tumor and the vicinity by the circulating BchlD, resulting in blood clotting and tumor vessels perforation followed by a complete arrest of the tumor vasculature within minutes of illumination. With some Bchl derivatives, direct intoxication of the endothelial cells was observed (Gross et al., 2003; Mazor et al., 2005). For reasons that are presently under investigation, the tumor vascular response is markedly faster and harsher compared with that of the vessels in the surrounding normal tissue. Treatment efficacy results in high cure rates (60-90% animal survival) (Mazor et al., 2005). Importantly, the IV injected sensitizers clears rapidly from the circulation of the treated animals (T1/2 is in the order of minutes to hours, (Mazor et al., 2005) avoiding prolonged skin toxicity and allowing for treatment repetition if needed. In Phase II clinical trials on localized prostate cancer in patients, where radiation therapy failed (Weersink et al., 2005), BchlD-based VTP has generally resulted in a successful eradication of the tumor lesions at 50-60% of the treated patients and remodeling of the tissue. A second treatment in both animal models and humans (phase II/III clinical trials) appear to result in similar or higher cure rates per session (depending on the drug and light dose), increasing the expected overall rate of success to ~90% after 2-3 sessions. Importantly, markedly higher cure rates per session were found in animal studies with higher doses of the applied sensitizer.

Photodynamic therapy (PDT) in tumors involves the combination of administered photosensitizer and local light delivery, both innocuous agents by themselves, but in the presence of molecular oxygen they are capable of producing cytotoxic reactive oxygen species (ROS) that can eliminate cells. Being a binary treatment modality, PDT allows for greater specificity, and has the potential of being more selective yet not less destructive when compared with commonly used chemotherapy or radiotherapy (Dougherty et al. 1998).

Application of novel bacteriochlorophyll (Bchl) derivatives as sensitizers in PDT has been reported by the present inventors in recent years (Zilberstein et al., 2001; Schreiber et al., 2002; Gross et al., 1997; Zilberstein et al., 1997; Rosenbach-Belkin et al., 1996; Gross et al., 2003a; Koudinova et al., 2003; Preise et al., 2003; Gross et al., 2003b) and in the patent publications U.S. Pat. Nos. 5,726,169 5,650,292, 5,955,585, 6,147,195, 6,740,637, 6,333,319, 6,569,846, 7,045,117, DE 41 21 876, EP 1 246 826, WO 2004/045492, WO 2005/120573. The spectra, photophysics, and photochemistry of Bchl derivatives have made them optimal light-harvesting molecules with clear advantages over other sensitizers presently used in PDT. These Bchl derivatives are mostly polar and remain in the circulation for a very short time with practically no extravasation into other tissues (Brandis, 2003; Mazor et al. 2005). Therefore, these compounds are good candidates for vascular targeted PDT (VTP) that relies on short (5-10 min) temporal intravascular encounter with light and higher susceptibility of the tumor vessels to the PDT-generated cytotoxic ROS.

Recent studies performed by our group showed that primary photosensitization is intravascular with rapid development of ischemic occlusions and stasis within the illumination period. This process also promotes photochemically induced lipid peroxidation (LPO) and early endothelial cell death that is primarily confined to the tumor vasculature (Koudinova et al. 2003). Due to light independent progression of free radical chain reactions along with developing hypoxia, LPO and cell death spread beyond the vascular compartment to cover the entire tumor interstitium until complete necrosis of the tumor is attained around 24 hours post PDT. Hence, the primary action of PDT blocks blood supply and induces hypoxia that initiates, in a secondary manner, a series of molecular and patho-physiological events that culminate with tumor eradication. Importantly, this approach relies on the differences between the response of normal and tumor blood vessels to the generated ROS.

International Application No. WO 2008/023378 of the same applicants, hereby incorporated by reference in its entirety as if fully disclosed herein, discloses novel conjugates of porphyrin, chlorophyll and bacteriochlorophyll (Bchl) derivatives with peptides containing the RGD motif or with RGD peptidomimetics, and their use in methods of in-vivo photodynamic therapy and diagnosis of tumors and different vascular diseases such as age-related macular degeneration. In particular, the Bchl derivative c(RGDfK)-Pd-MLT (Compound 24) showed accumulation of up to 4-8 µM in xenografts of primary tumors and stays at the tumor site for prolonged time enabling accumulation of the signal and a good signal to noise ratio.

Fluorescence tagging is suitable for in vivo, fresh tissue and in vitro detection. c(RGDfK)-Pd-MLT has intrinsic fluorescence in the near infra red (NIR) that can be detected. c(RGDfK)-2H-MLT has three orders of magnitude higher glowing ability and therefore might be an even better candidate for targeted imaging. In this study we showed that these molecules open the possibility to accurately detect tumor margins and necrosis in human breast adenocarcinoma model. Detecting tumor margins and necrosis present up to-date, two of the most challenging issues in tumor treatment. Moreover, both are faithful predictors of tumor re-growth after treatment. Thus, in the future, when clinically applied, the aforementioned RGD derivatives are expected to be suitable for tumor and necrosis detection on the operating table.

SUMMARY OF THE INVENTION

It has now been found in accordance with the present invention that the RGD-(bacterio)chlorophyll conjugates described in the above-mentioned WO 2008/023378 home and accumulate in necrotic tumor domains much longer than in tumor non-necrotic domains.

The present invention thus relates to the use of said RGD-bacteriochlorophyll and RGD-chlorophyll conjugates for minimally invasive tumor-targeted imaging, tumor-targeted photodynamic therapy, and/or on-line prognosis of necrotic tumors, and to methods therefore.

BRIEF DESCRIPTION OF DRAWINGS

The patent or application file contains at least one drawing executed in color. Copies of this patent or patent application publication with color drawings will be provided by the Office upon request and payment of the necessary fee.

FIGS. 4A-4B show accumulation of hereinafter compound 13 in MDA-MB-231-RFP orthotopic tumor (tumor size ~1 cm$^3$). Mice were injected with compound 13. Images were taken from 15 min to 24 h post drug injection. 4A (top panel): red fluorescence imaging. 4B (bottom panel): NIR fluorescence imaging.

FIGS. 5A-5B show accumulation of compound 13 in MDA-MB-231-RFP orthotopic tumor (tumor size ~1 cm$^3$). Mice were injected with compound 13. Images were taken from day 1 to 7 post drug injection. 5A (top panel): red fluorescence imaging. 5B (bottom panel): NIR fluorescence imaging.

FIGS. 7A-7B show accumulation of compound 13 in MDA-MB-231-RFP orthotopic tumor (tumor size ~0.5 cm$^3$). Mice were injected with compound 13. Images were taken from day 1 to 3 post drug injection. 7A (top panel): red fluorescence imaging. 7B (bottom panel): NIR fluorescence imaging.

FIGS. 9A-9B show accumulation of compound 24 in MDA-MB-231-RFP orthotopic tumor (tumor size ~1 cm$^3$). Mice were injected with compound 24. Images were taken from 1 h to 24 h post drug injection. 9A (top panel): red fluorescence imaging. 9B (bottom panel): NIR fluorescence imaging.

FIGS. 10A-10B show accumulation of compound 24 in MDA-MB-231-RFP orthotopic tumor (tumor size ~1 cm$^3$). Mice were injected with compound 24, and images were taken from day 1 to 7 post drug injection. 10A (top panel): red fluorescence imaging. 10B (bottom panel): NIR fluorescence imaging.

FIGS. 11A-11B show accumulation of compound 24 in MDA-MB-231-RFP orthotopic tumor (tumor size ~0.5 cm$^3$). Mice were injected with compound 24, and images were taken from 20 min to 24 h post drug injection. 11A (top panel): red fluorescence imaging. 11B (bottom panel): NIR fluorescence imaging.

FIGS. 12A-12B show accumulation of compound 24 in MDA-MB-231-RFP orthotopic tumor (tumor size ~0.5 cm$^3$). Mice were injected with compound 24, and images were taken from day 1 to 2 post drug injection. 12A (top panel): red fluorescence imaging. 12B (bottom panel): NIR fluorescence imaging.

FIGS. 13A-13B show accumulation of compound 13 in MLS-mBanana orthotopic tumor (tumor size ~1 cm$^3$). Mice were injected with compound 13. Images were taken from 1 h to 24 h post drug injection. 13A (top panel): red fluorescence imaging. 13B (bottom panel): NIR fluorescence imaging.

FIGS. 14A-14B show accumulation of compound 13 in MLS-mBanana orthotopic tumor (tumor size ~1 cm$^3$). Mice were injected with compound 13. Images were taken from day 1 to 4 post drug injection. 14A (top panel): red fluorescence imaging. 14B (bottom panel): NIR fluorescence imaging.

FIGS. 15A-15B show accumulation of compound 13 in MLS-mBanana orthotopic tumor (tumor size ~0.5 cm$^3$). Mice were injected with compound 13. Images were taken from 10 min to 24 hours post drug injection. 15A (top panel): red fluorescence imaging. 15B (bottom panel): NIR fluorescence imaging.

FIGS. 16A-16B show accumulation of compound 13 in MLS-mBanana orthotopic tumor (tumor size ~0.5 cm$^3$). Mice were injected with compound 13. Images were taken from day 1 to 4 post drug injection. 16A (top panel): red fluorescence imaging. 16B (bottom panel): NIR fluorescence imaging.

FIGS. 19A-19B show accumulation of compound 25 in MDA-MB-231-RFP orthotopic tumor (tumor size ~1 cm$^3$). Mice were injected with compound 25, and images were taken from day 1 to 3 post drug injection. 19A (top panel): red fluorescence imaging. 19B (bottom panel): NIR fluorescence imaging.

FIGS. 21A-21B show accumulation of compound 25 in MDA-MB-231-RFP orthotopic non-necrotic tumor (tumor size ~0.5 cm$^3$). Mice were injected with compound 25, and images were taken from day 1 to 3 post drug injection. 21A (top panel): red fluorescence imaging. 21B (bottom panel): NIR fluorescence imaging.

FIGS. 22A-22D show competition assay of compound 13 accumulation in orthotopic human breast MDA-MB-231-RFP primary tumor (tumor size -0.5 cm$^3$) when administrated 1 h after free c(RGDfK) administration. Images were taken 24 hours post compound 13 administration. 22A, 22B—red fluorescence imaging; 22C, 22D—NIR fluorescence imaging. 22A, 22C: compound 13 was administrated 1 h after free c(RGDfK) administration (competition). 22B, 22D: control, only compound 13 was administrated.

FIGS. 23A-23F show accumulation of compound 13 in the viable versus necrotic areas of the MDA-MB-231-RFP orthotopic tumor measured 10 min post drug injection. 23A, 23B and 23C (top panel), are an in vivo whole body photograph, red fluorescence image and NIR fluorescence image, respectively, of the intact animal; 23D, 23E and 23F (bottom panel), are a photograph, red fluorescence image and NIR fluorescence image, respectively, of the excised tumor (tumor was cut in half) (ND—necrotic domain, VD—viable domain).

FIGS. 24A-24F show accumulation of compound 13 in the viable versus necrotic areas of the MDA-MB-231-RFP orthotopic tumor measured 1 hour post drug injection. FIGS. 24A, 24B, 24C (top panel) and 24D, 24E, 24F (bottom panel) are as described above for FIGS. 23A, 23B, 23C and 23D, 23E, 23F, respectively.

FIGS. 25A-25F show accumulation of compound 13 in the viable versus necrotic areas of the MDA-MB-231-RFP orthotopic tumor measured 4 hours post drug injection. FIGS. 25A, 25B, 25C (top panel) and 25D, 25E, 25F (bottom panel) are as described above for FIGS. 23A, 23B, 23C and 23D, 23E, 23F, respectively.

FIGS. 26A-26F show accumulation of compound 13 in the viable versus necrotic areas of the MDA-MB-231-RFP orthotopic tumor measured 24 hours post drug injection. FIGS. 26A, 26B, 26C (top panel) and 26D, 26E, 26F (bottom panel) are as described above for FIGS. 23A, 23B, 23C and 23D, 23E, 23F, respectively.

FIGS. 27A-27F show accumulation of compound 13 in the viable versus necrotic areas of the MDA-MB-231-RFP orthotopic tumor measured 3 days after drug injection. FIGS. 27A, 27B, 27C (top panel) and 27D, 27E, 27F (bottom panel) are as described above for FIGS. 23A, 23B, 23C and 23D, 23E, 23F, respectively.

FIGS. 28A-28F show accumulation of compound 13 in the viable versus necrotic areas of the MDA-MB-231-RFP orthotopic tumor measured 5 days after drug injection. FIGS. 28A, 28B, 28C (top panel) and 28D, 28E, 28F (bottom panel) are as described above for FIGS. 23A, 23B, 23C and 23D, 23E, 23F, respectively.

FIGS. 29A-29F show accumulation of compound 13 in the viable versus necrotic areas of the MDA-MB-231-RFP orthotopic tumor measured 7 days after drug injection. FIGS. 29A, 29B, 29C (top panel) and 29D, 29E, 29F (bottom panel) are as described above for FIGS. 23A, 23B, 23C and 23D, 23E, 23F, respectively.

FIGS. 30A-30F show accumulation of compound 24 in the viable versus necrotic areas of the MDA-MB-231-RFP orthotopic tumor measured 9 days after drug injection. FIGS. 30A, 30B, 30C (top panel) and 30D, 30E, 30F (bottom panel) are as described above for FIGS. 23A, 23B, 23C and 23D, 23E, 23F, respectively.

FIGS. 31A-31F show accumulation of compound 13 in central necrosis of MLS-mBanana tumor, measured 7 days after injection. FIGS. 31A, 31B, 31C (top panel) and 31D, 31E, 31F (bottom panel) are as described above for FIGS. 23A, 23B, 23C and 23D, 23E, 23F, respectively.

FIGS. 32A-32F show accumulation of compound 13 in non-central necrosis of MLS-mBanana tumo, measured 7 days post drug injection. FIGS. 32A, 32B, 32C (top panel) and 32D, 32E, 32F (bottom panel) are as described above for FIGS. 23A, 23B, 23C and 23D, 23E, 23F, respectively.

FIGS. 33A-33D show excised tumor image and histological analysis (H&E-staining) of MDA-MB-231-RFP tumor cross section. 33A: a photograph of the tumor cross-section surface (macroscopic appearance). 33B: histological presentation of the cross-section surface (microscopic appearance). 33C: medium power view of the boxed area in 33B. 33D: high power view of a region at the interface between necrotic and viable tissue.

FIGS. 34A-34B show a representative example of local response of human MDA-MB-231-RFP to PDT. Mouse with MDA-MB-231-RFP xenograft (~0.5 cm$^3$) on the back was injected i.v. with 7.5 mg/kg compound 13 and illuminated 8 h later through the skin. 34A: photographs taken from day 0 (before treatment) and after treatment at 1, 4, 7, 12 and 90 days. 34B: in vivo whole-body red fluorescence imaging.

MODES FOR CARRYING OUT THE INVENTION

Figure 1A:
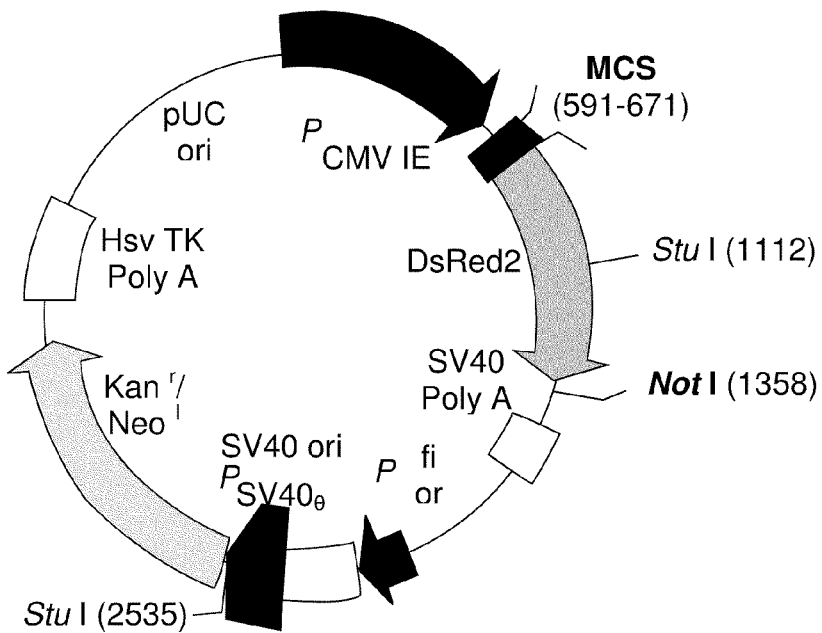
FIG. 1 shows the plasmids used for transfection of tumor cell lines with red fluorescent protein (RFP). 1A: pDsRed2-N1 plasmid (Clontech, Palo Alto, Calif.), 1B: pDsRed-Monomer-Hyg-C1 (Clontech, Palo Alto, Calif.), 1C: Modified pDsRed-Monomer-Hyg-C1.

It is a main abject of the present invention to provide conjugates of photosensitizers that especially target the sensitizer to necrotic domains of necrotic tumors. There are some advantages for tumor-targeted photodynamic therapy (PDT) over tumor targeting with conventional chemotherapy. First, during accumulation of a targeted conventional drug, it is often active, unless it is a prodrug, while the targeted photosensitizer is not active until locally illuminated. Second, a targeted conventional drug will bind and act also at undesirable targets presenting the homing address whereas the targeted photosensitizer will be activated only at the relevant illuminated site.

Thus, in a broad aspect, the present invention relates to the use of a conjugate of an RGD-containing peptide or an RGD peptidomimetic and a chlorophyll or bacteriochlorophyll photosensitizer for minimally invasive tumor-targeted imaging, tumor-targeted PDT, and/or on-line prognosis of necrotic tumors.

The terms "RGD-containing peptide" or "RGD peptide" are used herein interchangeably and mean a peptide containing the Arg-Gly-Asp (RGD) sequence, also referred to as RGD motif. The term "RGD peptidomimetic" as used herein refers to compounds, particularly, non-peptidic compounds, that mimic peptides and have the RGD motif.

RGD peptides are known to interact with integrin receptors of cells and have the potential to initiate cell-signaling processes and influence many diseases. for these reasons, the integrin RGD bonding site has been considered an attractive pharmaceutical target.

The RGD-containing peptide may be a linear or cyclic peptide composed of 4-100, preferably 5-50, 5-30, 5-20 or, more preferably, 5-10, amino acid residues. In preferred embodiments, the RGD peptide is composed of 4, 5, 6, 7, 9 or 25, most preferably 5 amino acid residues.

As used herein, the term "amino acid" includes the 20 naturally occurring amino acids as well as non-natural amino acids.

Examples of natural amino acids suitable for the invention include, but are not limited to, Ala, Arg, Asp, Asn, Cys, His, Gln, Glu, Gly, Ile, Leu, Lys, Met, Phe, Pro, Ser, Thr, Trp, Tyr, and Val.

Examples of non-natural amino acids include, but are not limited to, 4-aminobutyric acid (Abu), 2-aminoadipic acid, diaminopropionic (Dap) acid, hydroxylysine, homoserine, homovaline, homoleucine, norleucine (Nle), norvaline (Nva), ornithine (Orn), TIC, naphthylalanine (Nal), ring-methylated derivatives of Phe, halogenated derivatives of Phe or o-methyl-Tyr.

The term "amino acid" herein includes also modified amino acids such as modifications that occur post-translationally in vivo, for example, hydroxyproline, phosphoserine and phosphothreonine; D-modification; acylation or alkylation, preferably methylation, of the amino terminal group or of the free amino group of Lys; esterification or amidation of the carboxy terminal group or of a free carboxy group of Asp or Glu; and esterification or etherification of the hydroxyl group of Ser or Tyr.

The term "amino acid" includes both D- and L-amino acids. Thus, the peptides used in the conjugates of the invention can be all-D (except for glycine), all-L or L,D-amino acids. D-modifications of amino acids and N-alkylation of the peptide bond are most beneficial to prevent peptide cleavage by enzymes in the organism. In the present invention, a D-amino acid is indicated by a small letter as for the D-phenylalanine 'f' residue in the peptide cycloRGDfK of SEQ ID NO: 1 used herein.

The present invention includes also cyclic peptides. Peptides can be cyclized by a variety of methods such as formation of disulfides, sulfides and, especially, lactam formation between carboxyl and amino functions of the N- and C-termini or amino acid side chains. Cyclization can be obtained by any method known in the art, for example, through amide bond formation, e.g., by incorporating Glu, Asp, Lys, Orn, diamino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N(($CH_2$)$_n$—COOH)—C(R)H—COOH or H—N(($CH_2$)$_n$—$NH_2$)—C(R)H—COOH, wherein n=1-4, and further wherein R is any natural or non-natural side chain of an amino acid.

Cyclization can also be obtained via formation of S—S bonds through incorporation of two Cys residues. Additional side-chain to side chain cyclization can be obtained via formation of an interaction bond of the formula —($CH_2$)$_n$—S—$CH_2$—CO—, wherein n=1 or 2, which is possible, for example, through incorporation of Cys or homoCys and reaction of its free SH group with, e.g., bromoacetylated Lys, Orn, Dab or Dap.

In some embodiments, the RGD peptides may be those described in U.S. Pat. No. 6,576,239, EP 0927045 and WO 2008/023378, herein incorporated by reference in their entirety as if fully disclosed herein.

In one preferred embodiment, the peptide used according to the invention is the cyclic pentapeptide RGDfK of SEQ ID NO: 1, wherein 'f' indicates a D-Phe residue.

In another preferred embodiment, the peptide is the cyclic pentapeptide R<u>A</u>DfK of SEQ ID NO: 2 is used herein to facilitate the significance of the RGD motif in binding to integrin receptors. A further cyclopeptide useful according to the invention is the nonapeptide CDCRGDCGC of SEQ ID NO: 9, herein designated 'RGD-4C', which contains four cysteine residues forming two disulfide bonds in the molecule.

The aspartic acid residue of the RGD motif is highly susceptible to chemical degradation, leading to the loss of biological activity, and this degradation could be prevented by cyclization via disulfide linkage. Along with improving stability, cyclic peptides show higher potency compared to linear peptides in inhibiting the attachment of vitronectin to cells. The number and nature of residues flanking the RGD sequence in synthetic peptides have a significant influence on how that sequence is recognized by individual integrin receptors. An aromatic residue may be particularly significant in making favorable contacts in the binding site of integrin. Cyclic RGD peptides targeted for $\alpha_v\beta_3$ internalize by an integrin independent fluid-phase endocytosis pathway that does not alter the number of functional integrin receptors on the cell surface. Additionally, cyclic RGD peptides remain or degrade in the lysosome, in a process that reaches saturation after 15 minutes, and only a small portion can leave the lysosome and reach the cell cytoplasm.

In other preferred embodiments, the RGD peptide is selected from the cyclic peptides: (i) tetrapeptide cyclo-RGDK (SEQ ID NO: 3), pentapeptide cycloRGDf-n(Me)K (SEQ ID NO: 4), wherein f indicates D-Phe and the peptide bond between f and K is methylated; and pentapeptide cyclo-RGDyK (SEQ ID NO: 5), wherein y indicates D-Tyr.

In another embodiment, the RGD-containing peptide is linear and may be selected from the hexapeptide GRGDSP (SEQ ID NO: 6), the heptapeptide GRGDSPK (SEQ ID NO: 7), and the 25-mer (GRGDSP)$_4$K (SEQ ID NO: 8). In one more preferred embodiment, the linear peptide is GRGDSP.

In one embodiment of the invention, the RGD peptide is linked directly to the photosensitizer chlorophyll or bacteriochlorophyll macrocycle via a functional group in its periphery, for example, COOH, forming an amide CO—$NH_2$ group with the amino terminal group or a free amino group of the RGD peptide.

In another embodiment, the RGD peptide is linked to the photosensitizer macrocycle via a spacer arm/bridging group such as, but not limited to, a $C_1$-$C_{25}$ hydrocarbylene, preferably a $C_1$-$C_{10}$ alkylene or phenylene, substituted by an end functional group such as OH, COOH, $SO_3H$, COSH or $NH_2$, thus forming an ether, ester, amide, thioamide or sulfonamide group.

In some embodiments, the photosensitizer is conjugated to a RGd peptidomimetic.

In one preferred embodiment the RGD peptidomimetic is a non-peptidic compound comprising a guanidine and a carboxyl terminal groups spaced by a chain of 11 atoms, at least 5 of said atoms being carbon atoms, and said chain comprises one or more O, S or N atoms and may optionally be substituted by oxo, thioxo, halogen, amino, C1-C6 alkyl, hydroxyl, or carboxy or one or more atoms of said chain may form a 3-6 membered carbocyclic or heterocyclic ring. Compounds of this type are described in WO 93/09795 and WO 2008/023378 of the same applicant, herein incorporated by reference in its entirety as if fully disclosed herein.

In preferred embodiments, the RGD peptidomimetic above comprises in the chain N atoms and is substituted by an oxo group. In a more preferred embodiment, the RGD peptidomimetic has the formula:

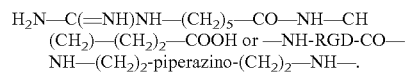

$H_2N$—C(=NH)NH—($CH_2$)$_5$—CO—NH—CH ($CH_2$)—($CH_2$)$_2$—COOH or —NH-RGD-CO—NH—($CH_2$)$_2$-piperazino-($CH_2$)$_2$—NH—.

The photosensitizer for use in the invention is a chlorophyll or bacteriochlorophyll derivative that may be a natural or a synthetic non-natural derivative of chlorophyll or bacteriochlorophyll, including compounds in which modifications have been made in the macrocycle, and/or in the periphery and/or the central Mg atom may be absent or it is replaced by other metal atom suitable for the purpose of diagnosis and/or for the purpose of PDT.

In preferred embodiments, the invention relates to a conjugate wherein the photosensitizer is a chlorophyll or bacteriochlorophyll of the formula I, II or III:

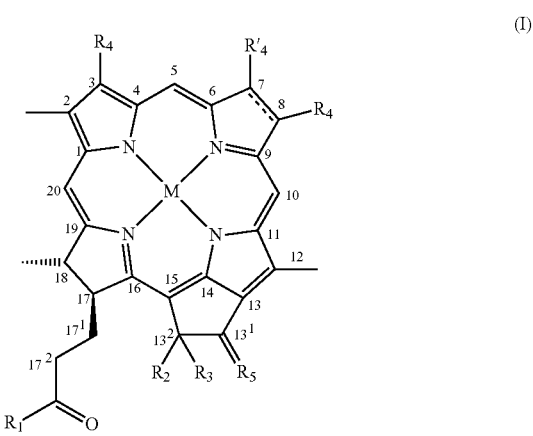

(I)

-continued

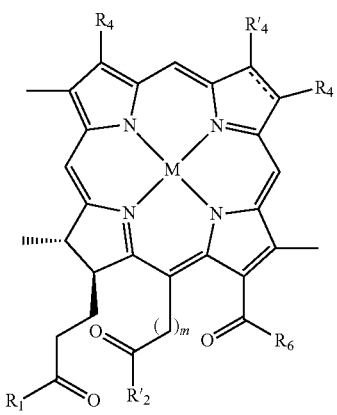

(II)

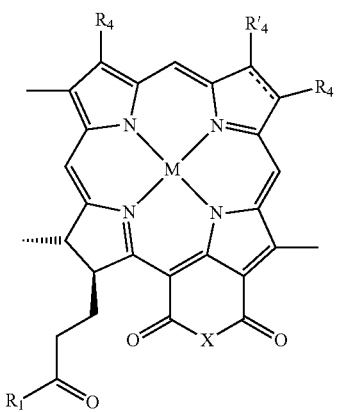

(III)

wherein

M represents 2H or an atom selected from the group consisting of Mg, Pd, Pt, Co, Ni, Sn, Cu, Zn, Mn, In, Eu, Fe, Au, Al, Gd, Dy, Er, Yb, Lu, Ga, Y, Rh, Ru, Si, Ge, Cr, Mo, P, Re, Tl and Tc and isotopes and radio-isotopes thereof;

X is O or N—$R_7$;

$R_1$, $R'_2$, and $R_6$ each independently is Y—$R_8$, —$NR_9R'_9$ or —$N^+R_9R'_9R''_9A^-$ or $R_1$ and $R_6$ in formula II together with the carbon atoms to which they are attached form a ring comprising an RGD peptide or RGD peptidomimetic;

Y is O or S;

$R_2$ is H, OH or $COOR_9$;

$R_3$ is H, OH, $C_1$-$C_{12}$ alkyl or $C_1$-$C_{12}$ alkoxy;

$R_4$ is —CH=$CR_9R'_9$, —CH=$CR_9$Hal, —CH=CH—$CH_2$—$NR_9R'_9$, —CH=CH—$CH_2$—$N^+R_9R'_9R''_9A^-$, —CHO, —CH=$NR_9$, —CH=$N^+R_9R'_9A^-$, —$CH_2$—$OR_9$, —$CH_2$—$SR_9$, —$CH_2$-Hal, —$CH_2$—$R_9$, —$CH_2$—$NR_9R'_9$, —$CH_2$—$N^+R_9R'_9R''_9A^-$, —$CH_2$—$CH_2R_9$, —$CH_2$—$CH_2$Hal, —$CH_2$—$CH_2OR_9$, —$CH_2$—$CH_2SR_9$, —$CH_2$—$CH_2$—$NR_9R'_9$, —$CH_2$—$CH_2$—$N^+R_9R'_9R''_9A^-$, —$COCH_3$, $C(CH_3)$=$CR_9R'_9$, —$C(CH_3)$=$CR_9$Hal, —$C(CH_3)$=$NR_9$, —$CH(CH_3)$=$N^+R_9R'_9A^-$, —$CH(CH_3)$-Hal, —$CH(CH_3)$—$OR_9$, —$CH(CH_3)$—$SR_9$, —$CH(CH_3)$—$NR_9R'_9$, —CH($CH_3$)—$N^+R_9R'_9R''_9A^-$, or —C≡$CR_9$;

$R'_4$ is methyl or formyl;

$R_5$ is =O, =S, =N—$R_9$, =$N^+R_9R'_9A^-$, =$CR_9R'_9$, or =$CR_9$-Hal;

$R_7$, $R_8$, $R_9$, $R'_9$ and $R''_9$ each independently is:

(a) H;

(b) $C_1$-$C_{25}$ hydrocarbyl;

(c) $C_1$-$C_{25}$ hydrocarbyl, preferably $C_1$-$C_{25}$ alkyl, alkenyl or alkynyl, more preferably $C_1$-$C_{10}$ or $C_1$-$C_6$ alkyl, substituted by one or more functional groups selected from the group consisting of halogen, nitro, oxo, OR, SR, epoxy, epithio, —CONRR', —COR, COOR, —$OSO_3R$, —$SO_3R$, —$SO_2R$, —$NHSO_2R$, —$SO_2NRR'$—NRR', =N—OR, =N—NRR', —C(=NR)—NRR', —NR—NRR', —(R)N—C(=NR)—NRR', O←NR—, >C=NR, —$(CH_2)_n$—NR—COR', —$(CH_2)_n$—CO—NRR', —O—$(CH_2)_n$—OR, —O—$(CH_2)_n$—O—$(CH_2)_n$—R, —PRR', —$OPO_3RR'$, —$PO_2HR$ and —$PO_3RR'$, wherein R and R' each independently is H, hydrocarbyl or heterocyclyl and R" is hydrocarbyl or heterocyclyl;

(d) $C_1$-$C_{25}$ hydrocarbyl, preferably $C_1$-$C_{25}$ alkyl, more preferably $C_1$-$C_{10}$ or $C_1$-$C_6$ alkyl, substituted by one or more functional groups selected from the group consisting of positively charged groups, negatively charged groups, basic groups that are converted to positively charged groups under physiological conditions, and acidic groups that are converted to negatively charged groups under physiological conditions;

(e) $C_1$-$C_{25}$ hydrocarbyl, preferably $C_1$-$C_{25}$ alkyl, more preferably $C_1$-$C_{10}$ or $C_1$-$C_6$ alkyl, containing one or more heteroatoms and/or one or more carbocyclic or heterocyclic moieties;

(f) $C_1$-$C_{25}$ hydrocarbyl, preferably $C_1$-$C_{25}$ alkyl, more preferably $C_1$-$C_{10}$ or $C_1$-$C_6$ alkyl, containing one or more heteroatoms and/or one or more carbocyclic or heterocyclic moieties and substituted by one or more functional groups as defined in (c) and (d) above;

(g) $C_1$-$C_{25}$ hydrocarbyl, preferably $C_1$-$C_{25}$ alkyl, more preferably $C_1$-$C_{10}$, or $C_1$-$C_6$ alkyl substituted by a residue of an amino acid, a peptide, preferably an RGD peptide, a protein, a monosaccharide, an oligosaccharide, a polysaccharide, or a polydentate ligand and its chelating complex with metals; or (h) a residue of an amino acid, a peptide, preferably an RGD peptide or an RGD peptidomimetic, a protein, a monosaccharide, an oligosaccharide, a polysaccharide, or a polydentate ligand and its chelating complex with metals;

$R_7$ may further be —NRR', wherein R and R' each is H or $C_1$-$C_{25}$ hydrocarbyl, preferably $C_1$-$C_{25}$ alkyl, more preferably $C_1$-$C_{10}$ or $C_1$-$C_6$ alkyl, optionally substituted by a negatively charged group, preferably $SO_3^-$;

$R_8$ may further be $H^+$ or a cation $R^+_{10}$ when $R_1$, $R'_2$ and $R_6$ each independently is Y—$R_8$;

$R^+_{10}$ is a metal, an ammonium group or an organic cation;

$A^-$ is a physiologically acceptable anion;

m is 0 or 1;

the dotted line at positions 7-8 represents an optional double bond; and pharmaceutically acceptable salts and optical isomers thereof;

and said chlorophyll or bacteriochlorophyll derivative of formula I, II or III contains at least one RGD-containing peptide residue.

In one embodiment, the dotted line at positions 7-8 represents a double bond and the photosensitizer is a chlorophyll of the formula I, II or III. The compounds of formula I wherein M is Mg, $R_1$ at position $17^3$ is phytyloxy, $R_2$ at position $13^2$ is $COOCH_3$, $R_3$ at position $13^2$ is an H atom, $R_5$ is O, $R_4$ at position 3 is vinyl, the dotted line at positions 7-8 represents a double bond, and either $R'_4$ is methyl at position 7 and $R_4$ is ethyl at position 8 or $R'_4$ is formyl at position 7 and $R_4$ is ethyl at position 8, are chlorophyll a and b, respectively, and their derivatives will have different metal atom and/or different substituents $R_1$, $R_2$, $R_3$, $R_4$, $R'_4$ and/or $R_5$.

In another embodiment, the positions 7-8 are hydrogenated and the photosensitizer is a bacteriochlorophyll of the formula I, II or III. The compounds of formula I wherein M is Mg, $R_1$ at position $17^3$ is phytyloxy or geranylgeranyloxy, $R_2$ at position $13^2$ is COOCH$_3$, $R_3$ at position $13^2$ is an H atom, $R_5$ is O, $R_4$ at position 3 is acetyl and at position 8 is ethyl, and the dotted line at positions 7-8 is absent are bacteriochlorophyll a, and their derivatives will have different metal atom and/or different substituents $R_1$, $R_2$, $R_3$, $R_4$, and/or $R_5$.

As used herein, the term "hydrocarbyl" means any straight or branched, saturated or unsaturated, acyclic or cyclic, including aromatic, hydrocarbyl radicals, of 1-25 carbon atoms, preferably of 1 to 20, more preferably 1 to 6, most preferably 2-3 carbon atoms. The hydrocarbyl may be an alkyl radical, preferably of 1-4 carbon atoms, e.g. methyl, ethyl, propyl, butyl, or alkenyl, alkynyl, cycloalkyl, aryl such as phenyl or an aralkyl group such as benzyl, or at the position 17 of the compounds of formula I, II or III, it is a radical derived from natural Chl and Bchl compounds, e.g. geranylgeranyl (2,6-dimethyl-2,6-octadienyl) or phytyl (2,6,10,14-tetramethyl-hexadec-14-en-16-yl).

As used herein, the term "carbocyclic moiety" refers to a monocyclic or polycyclic compound containing only carbon atoms in the ring(s). The carbocyclic moiety may be saturated, i.e. cycloalkyl, or unsaturated, i.e. cycloalkenyl, or aromatic, i.e. aryl.

The term "alkoxy" as used herein refers to a group ($C_1$-$C_{25}$)alkyl-O—, wherein $C_1$-$C_{25}$ alkyl is as defined above. Examples of alkoxy are methoxy, ethoxy, n-propoxy, isopropoxy, butoxy, isobutoxy, tert-butoxy, pentoxy, hexoxy, —OC$_{15}$H$_{31}$, —OC$_{16}$H$_{33}$, —OC$_{17}$H$_{35}$, —OC$_{18}$H$_{37}$, and the like. The term "aryloxy" as used herein refers to a group ($C_6$-$C_{18}$)aryl-O—, wherein $C_6$-$C_{18}$ aryl is as defined above, for example, phenoxy and naphthoxy.

The terms "heteroaryl" or "heterocyclic moiety" or "heteroaromatic" or "heterocyclyl", as used herein, mean a radical derived from a mono- or poly-cyclic heteroaromatic ring containing one to three heteroatoms selected from the group consisting of O, S and N. Particular examples are pyrrolyl, furyl, thienyl, pyrazolyl, imidazolyl, oxazolyl, thiazolyl, pyridyl, quinolinyl, pyrimidinyl, 1,3,4-triazinyl, 1,2,3-triazinyl, 1,3,5-triazinyl, benzofuryl, isobenzofuryl, indolyl, imidazo[1,2-a]pyridyl, benzimidazolyl, benzthiazolyl and benzoxazolyl.

Any "carbocyclic", "aryl" or "heteroaryl" may be substituted by one or more radicals such as halogen, $C_6$-$C_{14}$ aryl, $C_1$-$C_{25}$ alkyl, nitro, OR, SR, —COR, —COOR, —SO$_3$R, —SO$_2$R, —NHSO$_2$R, —NRR', —(CH$_2$)$_n$—NR—COR', and —(CH$_2$)$_n$—CO—NRR'. It is to be understood that when a polycyclic heteroaromatic ring is substituted, the substitutions may be in any of the carbocyclic and/or heterocyclic rings.

The term "halogen", as used herein, refers to fluoro, chloro, bromo or iodo.

In one embodiment of the invention, the photosensitizer of the conjugate is a chlorophyll or bacteriochlorophyll of the formula I, II or III containing at least one negatively charged group and/or at least one acidic group that is converted to a negatively charged group at the physiological pH.

As defined herein, "a negatively charged group" is an anion derived from an acid and includes carboxylate (COO$^-$), thiocarboxylate (COS$^-$), sulfonate (SO$_3^-$), and phosphonate (PO$_3^{2-}$), and the "acidic group that is converted to a negatively charged group under physiological conditions" include the carboxylic (—COOH), thio-carboxylic (—COSH), sulfonic (—SO$_3$H) and phosphonic (—PO$_3$H$_2$) acid groups. BChl derivatives with negatively charged groups or groups converted thereto under physiological conditions have been described in WO 2004/045492 of the same applicant, herewith incorporated by reference in its entirety as if fully disclosed herein.

In a more preferred embodiment, the photosensitizer in the conjugate of the invention is chlorophyll or bacteriochlorophyll of formula II, wherein $R_6$ is —NR$_9$R'$_9$, $R_9$ is H and R'$_9$ is $C_1$-$C_{10}$ alkyl substituted by SO$_3$H or an alkaline salt thereof. Most preferably, the conjugate comprises a bacteriochlorophyll derivative of formula II, wherein $R_6$ is —NH—(CH$_2$)$_2$—SO$_3$K or —NH—(CH$_2$)$_3$—SO$_3$K.

In another embodiment of the invention, the photosensitizer of the conjugate is a chlorophyll or bacteriochlorophyll of the formula I, II or III containing at least one positively charged group and/or at least one basic group that is converted to a positively charged group at the physiological pH.

As defined herein, "a positively charged group" denotes a cation derived from a N-containing group or from an onium group not containing N. Since tumor endothelium is characterized by an increased number of anionic sites, positively charged groups or basic groups that are converted to positively charged groups under physiological conditions, may enhance the targeting efficiency of the conjugates of the present invention.

A "cation derived from a N-containing group" as used herein denotes, for example, but is not limited to, an ammonium —N$^+$(RR'R"), hydrazinium —(R)N—N$^+$(R' R"), ammoniumoxy O←N$^+$(RR')—, iminium >C=N$^+$(RR'), amidinium —C(=RN)—N$^+$R'R" or guanidinium —(R)N—C(=NR)—N$^+$R'R" group, wherein R, R' and R" each independently is H, hydrocarbyl, preferably $C_1$-$C_6$ alkyl as defined herein, phenyl or benzyl, or heterocyclyl, or in the ammonium group one of R, R' and R" may be OH, or two of R, R' and R" in the ammonium group or R and R' in the hydrazinium, ammoniumoxy, iminium, amidinium or guanidinium groups, together with the N atom to which they are attached, form a 3-7 membered saturated ring, optionally containing one or more heteroatoms selected from the group consisting of O, S or N and optionally further substituted at the additional N atom, or said cation is derived from a compound containing one or more N atoms in a heteroaromatic ring.

In one more preferred embodiment, the conjugate of the present invention contains an ammonium group of the formula —N$^+$(RR'R"), wherein each of R, R' and R" independently is H or optionally substituted hydrocarbyl or heterocyclyl, as defined herein, or one of them may be OH. The —N$^+$(RR'R") ammonium group may be a secondary ammonium, wherein any two of the radicals R, R' or R" are H; a tertiary ammonium, wherein only one of R, R' or R" is H; or a quaternary ammonium, wherein each of R, R' or R" is an optionally substituted hydrocarbyl or heterocyclyl group as defined herein. When one of R, R' or R" is OH, the group is a hydroxylammonium group. Preferably, the ammonium group is a quaternary ammonium group wherein R, R' and R" each is $C_1$-$C_6$ alkyl such as methyl, ethyl, propyl, butyl, hexyl. The ammonium group may be an end group in the molecule or it may be found within an alkyl chain in the molecule.

In the hydrazinium —(R)N—N$^+$(R'R"), amidinium —C(=NR)—N$^+$R'R" and guanidinium —(R)N—C(=NR)—N$^+$R'R" groups, R, R' and R" may each independently be H or hydrocarbyl or heterocyclyl, or R' and R" together with the N atom to which they are attached form a 3-7 membered saturated ring, as defined herein. Examples of such groups include those wherein R is H, and R' and R" each is $C_1$-$C_6$ alkyl such as methyl, ethyl, propyl, butyl, hexyl.

In the ammoniumoxy O←N$^+$(RR')- and iminium >C=N$^+$ (RR') groups, R and R' may each independently be H or hydrocarbyl, preferably $C_1$-$C_6$ alkyl, or heterocyclyl, or R and R' together with the N atom to which they are attached form a 3-7 membered saturated ring, as defined herein.

In another preferred embodiment, the chlorophyll or bacteriochlorophyll derivative contains a cyclic ammonium group of the formula —$N^+$(RR'R"), wherein two of R, R' and R" together with the N atom form a 3-7 membered saturated ring defined hereinbelow.

As defined herein, "a 3-7 membered saturated ring" formed by two of R, R' and R" together with the N atom to which they are attached may be a ring containing only N such as aziridine, pyrrolidine, piperidine, piperazine or azepine, or it may contain a further heteroatom selected from O and S such as morpholine or thiomorpholine. The further N atom in the piperazine ring may be optionally substituted by alkyl, e.g. $C_1$-$C_6$ alkyl, that may be substituted by halo, OH or amino. The onium groups derived from said saturated rings include aziridinium, pyrrolidinium, piperidinium, piperazinium, morpholinium, thiomorpholinium and azepinium.

As defined herein "a cation derived from a N-containing heteroaromatic radical" denotes a cation derived from a N-heteroaromatic compound that may be a mono- or polycyclic compound optionally containing O, S or additional N atoms. The ring from which the cation is derived should contain at least one N atom and be aromatic, but the other ring(s), if any, can be partially saturated. Examples of N-heteroaromatic cations include pyrazolium, imidazolium, oxazolium, thiazolium, pyridinium, pyrimidinium, quinolinium, isoquinolinium, 1,2,4-triazinium, 1,3,5-triazinium and purinium.

The positively charged group may also be an onium group not containing nitrogen such as but not limited to, phosphonium [—$P^+$(RR'R")], arsonium [—$As^+$(RR'R")], oxonium [—$O^+$(RR')], sulfonium [—$S^+$(RR')], selenonium [—$Se^+$(RR')], telluronium [—$Te^+$(RR')], stibonium [—$Sb^+$(RR'R")], or bismuthonium [—$Bi^+$(RR'R")] group, wherein each of R, R' and R", independently, is H, hydrocarbyl or heterocyclyl, preferably $C_1$-$C_6$ alkyl such as methyl, ethyl, propyl, butyl, pentyl or hexyl, or aryl, preferably, phenyl.

Examples of phosphonium groups of the formula —$P^+$(RR'R") include groups wherein R, R' and R" each is methyl, ethyl, propyl, butyl or phenyl, or R is methyl, ethyl, propyl, butyl or hexyl and R' and R" both are phenyl. Examples of arsonium groups of the formula —$As^+$(RR'R") include groups wherein R, R' and R" each is methyl, ethyl, propyl, butyl or phenyl. Examples of sulfonium groups of the formula —$S^+$(RR') include groups wherein R and R' each is methyl, ethyl, propyl, butyl, phenyl, benzyl, phenethyl, or a substituted hydrocarbyl group.

As defined herein, "a basic group that is converted to a positively charged group under physiological conditions" is, at least theoretically, any basic group that will generate under physiological conditions a positively charged group as defined herein. It is to be noted that the physiological conditions, as used herein, do not refer solely to the serum, but to different tissues and cell compartments in the body.

Examples of such N-containing basic groups include, without being limited to, any amino group that will generate an ammonium group, any imine group that will generate an iminium group, any hydrazine group that will generate a hydrazinium group, any aminoxy group that will generate an ammoniumoxy group, any amidine group that will generate an amidinium group, any guanidine group that will generate a guanidinium group, all as defined herein. Other examples include phosphino and mercapto groups.

Thus, the conjugates of the present invention may contain at least one basic group that is converted to a positively charged group under physiological conditions such as —NRR', —C(=NR)—NR'R", —NR—NR'R", —(R)N—C(=NR)—NR'R", O←NR—, or >C=NR, wherein each of R, R' and R" independently is H, hydrocarbyl, preferably $C_1$-$C_{25}$ alkyl, more preferably $C_1$-$C_{10}$ or $C_1$-$C_6$ alkyl, or heterocyclyl, or two of R, R' and R" together with the N atom form a 3-7 membered saturated ring, optionally containing an O, S or N atom and optionally further substituted at the additional N atom, or the basic group is a N-containing heteroaromatic radical.

The 3-7 membered saturated ring may be aziridine, pyrrolidine, piperidine, morpholine, thiomorpholine, azepine or piperazine optionally substituted at the additional N atom by $C_1$-$C_6$ alkyl optionally substituted by halo, hydroxyl or amino, and the N-containing heteroaromatic radical may be pyrazolyl, imidazolyl, oxazolyl, thiazolyl, pyridyl, quinolinyl, isoquinolinyl, pyrimidyl, 1,2,4-triazinyl, 1,3,5-triazinyl or purinyl.

BChl derivatives with positively charged groups or groups converted thereto under physiological conditions have been described in WO 2005/120573 of the same applicant, herewith incorporated by reference in its entirety as if fully disclosed herein.

In one embodiment, the photosensitizer is a chlorophyll or bacteriochlorophyll of formula II and $R_6$ is a basic group —$NR_9R'_9$ wherein $R_9$ is H and $R'_9$ is $C_1$-$C_6$ alkyl substituted by a basic group —NRR' or —NH—$(CH_2)_{2-6}$—NRR' wherein each of R and R' independently is H, $C_1$-$C_6$ alkyl optionally substituted by $NH_2$ or R and R' together with the N atom form a 5-6 membered saturated ring, optionally containing an O or N atom and optionally further substituted at the additional N atom by —$(CH_2)_{2-6}$—$NH_2$.

In another embodiment, the photosensitizer is a bacteriochlorophyll of formula II and $R_6$ is —NH—$(CH_2)_3$—NH—$(CH_2)_3$—$NH_2$, —NH—$(CH_2)_2$-1-morpholino, or —NH—$(CH_2)_3$-piperazino-$(CH_2)_3$—$NH_2$.

In a further embodiment, $R_1$ and $R_6$ together form a cyclic ring comprising an RGD peptide or RGD peptidomimetic.

In another embodiment, the photosensitizer is a chlorophyll or bacteriochlorophyll of formula III, X is —$NR_7$, $R_7$ is —NRR', R is H and R' is $C_1$-$C_6$ alkyl substituted by $SO_3$— or an alkaline salt thereof, preferably the photosensitizer is a bacteriochlorophyll and X is —$NR_7$ and $R_7$ is —NH—$(CH_2)_3$—$SO_3K$.

In another embodiment, $R_7$, $R_8$, $R_9$ or $R'_9$ each is a $C_1$-$C_6$ alkyl substituted by one or more —OH groups. For example, the photosensitizer is a chlorophyll or bacteriochlorophyll of formula II and $R_6$ is —$NR_9R'_9$, $R_9$ is H and $R'_9$ is $HOCH_2$—CH(OH)—$CH_2$—.

In another embodiment, the photosensitizer is a chlorophyll or bacterio-chlorophyll of formula II and $R_6$ is —$NR_9R'_9$, $R_9$ is H and $R'_9$ is $C_1$-$C_6$ alkyl substituted by a polydentate ligand or its chelating complexes with metals. Examples of polydentate ligands include, without being limited to, EDTA (ethylenediamine tetraacetic acid), DTPA (diethylene triamine pentaacetic acid) or the macrocyclic ligand DOTA. In one preferred embodiment the polydentate ligand is DTPA, $R_6$ is —NH—$(CH_2)_3$—NH-DTPA, and the metal is Gd.

The cation $R_8^+$ may be a monovalent or divalent cation derived from an alkaline or alkaline earth metal such as $K^+$, $Na^+$, $Li^+$, $NH_4^+$, $Ca^{2+}$, more preferably $K^+$; or $R_8^+$ is an organic cation derived from an amine or from a N-containing group As defined herein, the $C_1$-$C_{25}$ hydrocarbyl defined for $R_7$, $R_8$, $R_9$ and $R'_9$ may optionally be substituted by one or more functional groups selected from halogen, nitro, oxo, OR, SR, epoxy, epithio, aziridine, —CONRR', —COR, COOR, —OSO$_3$R, —SO$_3$R, —SO$_2$R, —NHSO$_2$R, —SO$_2$NRR'—NRR', =N—OR, =N—NRR', —C(=NR)—NRR', —NR—NRR', —(R)N—C(=NR)—NRR', O←NR—, >C=NR, —(CH$_2$)$_n$—NR—COR', —(CH$_2$)$_n$—CO—NRR', —O—(CH$_2$)$_n$—OR, —O—(CH$_2$)$_n$—O—(CH$_2$)$_n$—R, —PRR', —OPO$_3$RR', —PO$_2$HR, —PO$_3$RR'; one or more negatively charged groups such as COO$^-$, COS$^-$, —OSO$_3^-$, —SO$_3^-$, —OPO$_3$R$^-$, —PO$_2$H$^-$, —PO$_3^{2-}$ and —PO$_3$R$^-$; and/or one or more positively charged groups such as —P$^+$(RR'R''), —As$^+$(RR'R''), —O$^+$(RR'), —S$^+$(RR'), —Se$^+$(RR'), —Te$^+$(RR'), —Sb$^+$(RR'R''), —Bi$^+$(RR'R''), O←N$^+$(RR')—, >C=N$^+$(RR'), —N$^+$(RR'R''), —(R)N—N$^+$(RR'R''), —(R)N—C(=HN)—N$^+$RR'R'', —C(=NH)—N$^+$(RR'R''), or a N-heteroaromatic cation such as pyrazolium, imidazolium, oxazolium, thiazolium, pyridinium, quinolinium, pyrimidinium, 1,2,4-triazinium, 1,3,5-triazinium and purinium; wherein n is an integer from 1 to 6, R, R' and R'' each independently is H, hydrocarbyl or heterocyclyl, or two of R, R' and R'' together with the N atom to which they are attached form a 3-7 membered saturated ring, optionally containing one or more heteroatoms selected from the group consisting of O, S or N and optionally further substituted at the additional N atom. The C$_1$-C$_{25}$ hydrocarbyl defined for R$_7$, R$_8$, R$_9$ and R'$_9$ may also be substituted by the residue of a mono-, oligo- or polysaccharide such as glycosyl, or of an amino acid, peptide or protein, preferably an RGD-peptide. In addition, R$_8$, R$_9$ and R'$_9$ each may independently be a residue of a mono-, oligo- or polysaccharide such as glycosyl, or of an amino acid, peptide or protein, or a polydentate ligand such as DTPA, DOTA, EDTA and the like and their chelating complexes with metals.

In the groups OR and SR, when R is H, the groups hydroxy and mercapto are represented, respectively, and when R is other than H, ethers and sulfides are represented. In the group —PRR', the phosphino group is represented when R and R' are H. In the group —COR, when R is H, the formyl group —CHO of an aldehyde is represented, while when R is other than H, this is the residue of a ketone such as alkylcarbonyl and arylcarbonyl groups. In the group COOR, when R is not H, this is a carboxylic acid ester group such as the alkoxycarbonyl and aryloxycarbonyl groups. Similarly, esters are represented in the groups —OSO$_3$R, —SO$_3$R, —SO$_2$R, —OPO$_3$RR', —PO$_2$HR and —PO$_3$RR' when R and R' are other than H.

In one preferred embodiment of the invention, the photosensitizer is unmetalated, namely, M is 2H. In other preferred embodiments, the photosensitizer is metalated as defined hereinabove, more preferably M is Pd, Cu or Mn, most preferably Pd or Cu.

In some preferred embodiments of the invention, the photosensitizer is a Bchl of the formula I, II or III, more preferably formula II, and M is 2H, Cu, Mn, or Pd. In other embodiments, the photosensitizer is a Chl of the formula I, II or III, more preferably formula II, and M is 2H, Cu or Mn.

In some preferred embodiments, the conjugate comprises a photosensitizer Bchl of the formula II wherein M is Pd, Mn, Cu or 2H; m is 0; R$_1$ is NH—P, wherein P is the residue of an RGD-containing peptide or RGD peptidomimetic linked directly to the NH— or via a spacer; R'$_2$ is methoxy; R$_4$ at position 3 is acetyl and at position 8 is ethyl; R'$_4$ is methyl; and R$_6$ is —NH—(CH$_2$)$_n$—SO$_3^-$ Me$^+$, wherein n is 2 or 3 and Me$^+$ is Na$^+$ or K$^+$.

In a most preferred embodiment of the invention, the conjugate comprises Bchl of the formula II, wherein M is 2H, R$_1$ is NH—P, wherein P is the residue of the RGD containing peptide c(RGDfK) of SEQ ID NO: 1, R'$_2$ is methoxy, R$_4$ at position 3 is acetyl and at position 8 is ethyl, R'$_4$ is methyl, and R$_6$ is —NH—(CH$_2$)$_2$—SO$_3$K, herein designated compound 13 or c(RGDfK)-2H-MLT.

In another most preferred embodiment, M is Pd and R$_1$, R'$_2$, R$_4$, R'$_4$R$_6$ are as defined above, and P is c(RGDfK) of SEQ ID NO: 1, herein designated compound 24 or c(RGDfK)-Pd-MLT.

In a more preferred embodiment, M is Mn, R$_1$, R'$_2$, R$_4$, R'$_4$R$_6$ are as defined above, and P is c(RGDfK), herein designated compound 14 or c(RGDfK)-Mn-MLT, or M is Cu and conjugate is designated herein compound 15 or c(RGDfK)-Cu-MLT.

In a further more preferred embodiment, M in the Bchl of formula II is 2H, R'$_2$, R$_4$, R'$_4$ and R$_6$ are as defined above, and R$_1$ is NH—P wherein P is c(RADfK) of SEQ ID NO: 2 herein designated compound 45 or c(RADfK)-2H-MLT, or P is the c(RGDyK) of SEQ ID NO: 5.

In other more preferred embodiments, M is 2H, R$_1$, R'$_2$, R$_4$, R'$_4$ and R$_6$ are as defined above and P is a linear peptide selected from GRGDSP of SEQ ID NO: 6, or GRGDSPK of SEQ ID NO: 7 or (GRGDSP)$_4$ of SEQ ID NO: 8, most preferably P is GRGDSP and the conjugate is herein designated compound 26 or linear GRGDSP-2H-MLT.

In still more preferred embodiments, in the Bchl of the formula II, M is Pd, m is 0, R$_1$ is NH—P wherein P is c(RGDfK), R'$_2$ is methoxy, R$_4$ at position 3 is acetyl and at position 8 is ethyl, R'$_4$ is methyl, and R$_6$ is —NH—(CH$_2$)$_3$—SO$_3$K, or P is the cyclopeptide RGDf-n(Me)K of SEQ ID NO: 4 and R$_6$ is —NH—(CH$_2$)$_2$—SO$_3$K.

Further more preferred embodiments wherein the central metal atom of Bchl of formula II is Pd; m, R'$_2$, R$_4$, R'$_4$ are as defined above, R$_1$ is HH—P and R$_6$ is —NH—(CH$_2$)$_2$—SO$_3$K, relate to conjugates with the liner peptides GRGDSPK of SEQ ID NO: 7 or (GRGDSP)$_4$ of SEQ ID NO: 8.

In yet still more preferred embodiment the conjugate comprises a Bchl of the formula II wherein M is Pd; m, R'$_2$, R$_4$, R'$_4$ are as defined above, R$_1$ is NH—CH [(—(CH$_2$)$_2$—CO—NH—P]$_2$, wherein P is the residue of the RGD-containing peptide c(RGDyK) of SEQ ID NO: 5, and R$_6$ is —NH—(CH$_2$)$_2$—SO$_3$K, herein designated compound 36 or c(RGDyK)$_2$-2H-MLT.

In another two more preferred embodiments of the invention, in the Bchl of the formula II M is Pd or 2H; m is 0; R$_1$ is NH—P, wherein P is the residue of c(RGDfK) (SEQ ID NO: 1), R'$_2$ is methoxy; R$_4$ at position 3 is acetyl and at position 8 is ethyl; R'$_4$ is methyl, and R$_6$ is —NH—CH$_2$—CH(OH)—CH$_2$OH.

In yet another more preferred embodiments, the conjugates comprise an RGD peptide as mentioned above, preferably c(RGDfK) conjugated to a Bchl of the formula II wherein M is 2H; m, R$_1$, R'$_2$, R$_4$, R'$_4$ are as defined above and R$_6$ is either NH—(CH$_2$)$_3$—NH—(CH$_2$)$_3$—NH$_2$, —NH—(CH$_2$)$_2$-morpholino or —NH—(CH$_2$)$_3$-piperazino-(CH$_2$)$_3$—NH$_2$.

Further more preferred embodiments relate to conjugates comprising a Bchl of the formula II wherein M is 2H; m is 0; R$_1$ is NH-c(RGDfK), R'$_2$ is methoxy, R$_4$ at position 3 is acetyl and at position 8 is ethyl, R'$_4$ is methyl; and R$_6$ is —NH—(CH$_2$)$_3$—NH—CO-DTPA, or its chelate complex with Gd.

The invention further relates to preferred conjugates which comprise a photosensitizer Bchl of the formula II wherein M is Pd or 2H; m is 0; R$_1$ is NH—P, wherein P is the residue of an RGD peptidomimetic linked directly to the NH— or via a spacer; R'$_2$ is methoxy; R$_4$ at position 3 is acetyl and at position 8 is ethyl; R'$_4$ is methyl; and R$_6$ is —NH—CH$_2$—CH(OH)—CH$_2$—OH or —NH—(CH$_2$)$_2$—SO$_3$K.

In another embodiment of the invention, the conjugate comprises a Bchl of the formula III wherein M is Pd; R$_1$ is NH—P, wherein P is the residue of an RGD-containing peptide or RGD peptidomimetic linked directly to the NH— or via a spacer; $R_4$ at position 3 is acetyl and at position 8 is ethyl; $R'_4$ is methyl; X is N—$R_7$ and $R_7$ is —NH—$(CH_2)_3$—$SO_3^-$ $Me^+$, wherein $Me^+$ is $Na^+$ or $K^+$.

In another embodiment, the conjugate comprises a Bchl of the formula I wherein M is Mn; $R_1$ is NH—P, wherein P is the residue of an RGD-containing peptide or RGD peptidomimetic linked directly to the NH— or via a spacer; $R_2$ is OH; $R_3$ is $COOCH_3$; $R_4$ at position 3 is acetyl and at position 8 is ethyl; $R'_4$ is methyl; and $R_5$ is O. In more preferred embodiments, M is 2H or Mn, and P is the residue of the RGD-containing peptide c(RGDfK) of SEQ ID NO: 1 or c(RGDK) of SEQ ID NO: 3.

In another embodiment, the conjugate comprises a Chl of the formula II wherein M is selected from Mn, Cu or 2H; $R_1$ is NH—P, wherein P is the residue of an RGD-containing peptide or RGD peptidomimetic linked directly to the NH— or via a spacer; $R_4$ at position 3 is vinyl and at position 8 is ethyl; $R'_4$ is methyl; and $R_6$ is —NH—$(CH_2)_2$—$SO_3^-$ $Me^+$, wherein $Me^+$ is $Na^+$ or $K^+$.

In more preferred embodiments in the Chl of formula II, M is 2H or Cu or Mn, and $R_4$, $R'_4$ and $R_6$ are as defined above and the photosensitizer is conjugated to the pentacyclic RGD-containing peptide c(RGDfK) of SEQ ID NO: 1.

In another embodiment, $R_1$ and $R_6$ together form a cyclic ring comprising —NH-RGD-CO—NH—$(CH_2)_2$—NH— or —NH-RGD-CO—NH—$(CH_2)_2$-piperazino-$(CH_2)_2$—NH—. In one embodiment, the conjugate comprises a Bchl of the formula II wherein m is 0; $R'_2$ is methoxy; $R_4$ at position 3 is acetyl and at position 8 is ethyl; $R'_4$ is methyl; and either $R_1$ and $R_6$ together form a cyclic ring comprising —NH-RGD-CO—NH—$(CH_2)_2$—NH— and M is Pd or M is 2H or $R_1$ and $R_6$ together form a cyclic ring comprising —NH-RGD-CO—NH—$(CH_2)_2$-piperazino-$(CH_2)_2$—NH— and M is Pd.

Industrial Applicability

For use in the present invention, the conjugates are formulated in a pharmaceutical composition comprising a pharmaceutically acceptable carrier.

In one embodiment, the pharmaceutical composition is for use in photodynamic therapy (PDT), more particularly for tumor-targeted PDT. In another embodiment, the pharmaceutical composition is for use for diagnostic purposes, for visualization of tumor necrotic domains.

Several diagnostic techniques can be applied in accordance with the invention, by adapting the central metal atom to the particular technique.

For tumor necrotic domains diagnosis by dynamic fluorescence imaging, M in the photosensitizer is 2H or a metal selected from Pd and Zn.

For tumor necrotic domains diagnosis by radiodiagnostic technique, M in the photosensitizer is a radioisotope selected from $^{64}Cu$, $^{67}Cu$, $^{99m}Tc$, $^{67}Ga$, $^{201}Tl$, $^{195}Pt$, $^{60}Co$, $^{111}In$ and $^{51}Cr$. In one embodiment, the radiodiagnostic technique is positron emission tomography (PET) and M is $^{64}Cu$ or $^{67}Cu$. In another embodiment, the radiodiagnostic technique is single photon emission tomography (SPET) and M is a radioisotope selected from $^{99m}Tc$, $^{67}Ga$, $^{195}Pt$, $^{111}In$, $^{51}Cr$ and $^{60}Co$.

For tumor necrotic domains diagnosis by molecular magnetic resonance imaging (MRI), M is a paramagnetic metal selected from $Mn^{3+}$, $Cu^{2+}$, $Fe^{3+}$, $Eu^{3+}$, $Gd^{3+}$ and $Dy^{3+}$, or the photosensitizer is substituted by a metal chelate complex of a polydentate ligand and the metal is as defined hereinbefore.

In one embodiment, the invention relates to a method for imaging of tumor necrotic domains by dynamic fluorescence imaging, which comprises:

(a) administering to a subject suspected of having a tumor with necrotic domains a conjugate according to the invention, wherein M is 2H or a metal selected from Pd and Zn;

(b) illuminating the subject and measuring the fluorescence of the suspected areas during at least 24-48 hours after administration of the conjugate at time intervals of 1-8 hours, wherein the areas that exhibit fluorescence after 24-48 hours or longer indicate the presence of tumor necrotic domains.

In preferred embodiments, the conjugate for the above method is the compound 13 or compound 24, the tumor is mammary or ovarian tumor, and the necrotic domains are visualized 3 to 8 days, preferably 5-8 days, post drug (conjugate) injection.

In another embodiment, the invention provides a method for diagnosis of tumor necrotic domains by radiodiagnostic technique, which comprises:

(a) administering to a subject suspected of having a tumor a conjugate as in accordance with the invention, wherein M is a radioisotope selected from the group consisting of $^{64}Cu$, $^{67}Cu$, $^{99m}Tc$, $^{67}Ga$, $^{201}Tl$, $^{195}Pt$, $^{60}Co$, $^{111}In$ or $^{51}Cr$.

(b) scanning the subject in an imaging scanner during at least 24-48 hours after administration of the conjugate at time intervals of 1-8 hours, and measuring the radiation level of the suspected areas, wherein the areas that exhibit radiation after 24-48 hours or longer indicate the presence of tumor necrotic domains.

The invention also provides a molecular magnetic resonance imaging (MRI) method for diagnosis of tumor necrotic domains comprising the steps of:

(a) administering to a subject suspected of having a tumor a conjugate as defined herein, wherein M is a paramagnetic metal selected from $Mn^{3+}$, $Cu^{2+}$, $Fe^{3+}$, $Eu^{3+}$, $Gd^{3+}$ or $Dy^{3+}$; and (b) subjecting the patient to magnetic resonance imaging by generating at least one MR image of the target region of interest within the patient's body prior to said administration (zero time) and one or more MR images at a second or more time points at least 24-48, preferably 96, hours after said administration; and (c) processing and analyzing the data to diagnose the presence or absence of said tumor necrotic domains.

The invention further provides a method for mapping of tumor margins before surgery comprising administering to a subject in need a conjugate as defined herein, illuminating the subject and scanning by imaging the tumor, preferably breast tumor, at the first 2-24 h after administration of the conjugate, thus mapping the margins of the tumor in preparation for the surgery.

The invention still further provides a minimally invasive treatment, detection and prognosis strategy for localized breast cancer, in particular ductal carcinoma in situ (DCIS), comprising (i) administering to a subject a conjugate as defined herein, preferably an RGD-Bchl conjugate, whereby the RGD-Bchl conjugate specifically homes and accumulates in the tumor necrotic domains, (ii) tumor-targeted imaging the subject treated with the RGD-BChl derivative by any of the methods described above for tumor detection and tumor margin definition at high precision as well as prognosis by MRI, fluorescence, and PET SCAN approaches; and (iii) tumor-targeted photodynamic therapy (PDT) of the localized necrotic areas allowing breast conservation and remodeling.

The RGD peptide-photosensitizer conjugates used in the invention are particularly suitable for tumor-targeting PDT of necrotic tumors and are useful for treatment of cancerous diseases.

Thus, in one embodiment, the conjugates of the invention are useful in the oncological field for treatment by PDT of precancerous states and several cancer types such as, but not limited to, melanoma, prostate, brain, colon, ovarian, breast, colorectal, head and neck, chest wall tumors arising from breast cancer, skin, lung, esophagus and bladder cancers and tumors. The compounds are useful for treatment of primary as well as metastatic necrotic tumors.

In one preferred embodiment, the method is used for treatment of localized breast cancer, particularly ductal carcinoma in situ.

According to the invention, a method for tumor photodynamic therapy of necrotic tumors is provided, which comprises: (a) administering to an individual in need a RGD peptide-photosensitizer conjugate according to the invention; and (b) irradiating the local of the tumor and its necrotic domains after determining the presence of necrotic domains at least 24 hours, preferably 2, 3, 4, 5, 6, 7 or 8 days after injection of the conjugate, by any of the methods described herein.

In one aspect, the present invention relates to a new method for tumor necrosis detection that is based on the selective up-take and prolonged accumulation of fluorescent Chl/Bchl-RGD conjugates in the tumor necrotic domains. The Chl/Bchl sensitizer is conjugated to ligands that home at specific receptors of the endothelial and tumor cells. Then, photodynamic generation of ROS is initiated by illuminating the tumor volume and close vicinity once the Chl/Bchl accumulates at sufficiently high concentrations and cleared from the surrounding tissue.

The Bchl component of compound 24 has intrinsic fluorescence in the near infra red (NIR) that can be detected. Recent experiments, using compound 24, showed accumulation of up to 4-8 µM in xenografts of primary tumors. Compound 24 stays at the tumor site for prolonged time enabling accumulation of the signal and a good signal to noise ratio. These abilities of the molecule probably rely on the interaction between Bchl and serum-albumin, making this molecule a good candidate for directed imaging and eventually directed therapy. Another Bchl derivative, compound 13, has three orders of magnitude higher glowing ability and therefore might be an even better candidate for targeted imaging. These molecules open the possibility to accurately detect tumor margins and necrosis in human breast adenocarcinoma model. Detecting tumor margins and necrosis present up to-date, two of the most challenging issues in tumor treatment. Moreover, both are faithful predictors of tumor re-growth after treatment. Thus, in the future, when clinically applied, the aforementioned RGD derivatives are expected to be suitable for tumor and necrosis detection on the operating table.

The present invention has introduced a new approach to achieve prolonged accumulation of Chl/Bchl derivatives that are conjugated with RGD peptides in tumor necrotic domains after temporal residence in the viable tumor tissue. The accumulated compounds can be used for in-vivo imaging of the viable (at short times after administration) or necrotic (at longer times) tumor domains, as well as for tumor therapy by PDT, chemo or isotope radiation therapies by changing the Bchl central metal or by further conjugation to small therapeutic agents. The new approach has been exemplified by the compounds 13 and 24. The c(RGDfK) has already been recognized as a highly specific ligand for $\alpha_v\beta_3$ and $\alpha_v\beta_5$ integrins that are up-regulated in angiogenesis. The compound 25 moiety provides the conjugate with a strong autofluorescence at NIR, making it suitable for fluorescent imaging after tissue uptake.

Experimental data show that the RGD moiety is essential for the specific accumulation of compound 13 and 24 in both small (non-necrotic) and large (necrotic) tumors since no short or long term accumulation was observed for the non-conjugated compound 25. Furthermore, the overall clearance of compound 25 from the treated mouse was significantly faster than that of the conjugated compound. The RGD pending mechanism is reinforced by the competition experiment described herein, where an excess of free c(RGDfK), injected shortly or concomitantly with the compound 13, prevented the later up-take by the tumor tissue.

A dramatic difference was observed in compound 13 accumulation between necrotic and non-necrotic tumors. Thus, small MDA-MB-231-RFP tumors (~0.5 cm$^3$), that have not yet developed necrosis, showed a rapid accumulation of compound 13 in the tumor within 1-6.5 h post drug injection followed by rapid (<24 h) clearance. Only very small amounts of the drug could be detected in the tumor at later times when most of the remaining drug was confined to clearance organs (mainly kidneys but also liver). Large MDA-MB-231-RFP (>1 cm$^3$) tumors that have developed necrosis showed slower accumulation that reached peak tumor concentration ratio, compared to other organs, from 48 h post drug injection. The average drug concentration in the tumor mass only slightly reduced from 24 h post drug injection. These results are general to necrotic tumor regions but differ with tumor type. Furthermore, similar difference between the accumulation patterns in necrotic and non-necrotic tumors were observed for compound 24 except for slower clearance rates observed in the liver making compound 13a better candidate for clinical applications.

Possibly, the difference observed herein between the rates of compound 13 accumulation in necrotic and non-necrotic regions in a model of breast cancer and a model of ovarian cancer tumors is related to the different nature of the microenvironment in the two tumor types. An inverse relationship between tumor volume and microvessel density was found in breast tumors: as the tumor volume increases, there is a dramatic decrease in the density of microvessels per cubic centimeter. Hence, the concentration of integrins becomes proportionally lower, and therefore the rate of integrin dependent drug accumulation should be proportionally lower.

The most striking feature of the presented data is the clear displacement of the drug fluorescence from the viable into the necrotic tumor volume demonstrated by the excised tumor fluorescence imaging of the necrotic MDA-MB-231-RFP tumors at different times after the compound 13 administration. Following the dependence of drug accumulation on the RGD moiety, a multi-step accumulation may be possible, where the first step involves dissociation of the compound 25 moiety (2H-MLT) from a serum albumin molecule and an active uptake by $\alpha_v\beta_3$ integrins in the microvasculature, viable tumor cells and possibly, macrophages or neutrophils. This step is suggested to be followed by a passive transfer or transcytosis migration of the access compound 13 into the necrotic domain and lack of drainage from there for prolonged time. In non-necrotic tumors, the drug accumulates rapidly, through the viable area, consisting of the entire tumor, but since no necrosis is present, the drug is rapidly cleared. When compound 24 was injected the excised tumor fluorescence results were similar to those obtained for compound 13.

Similar differences in the rate of accumulation in necrotic and non necrotic tumors were found in other tumors models, i.e. MLS-mBanana, human ovarian cancer. However, there is some variation in the rates and accumulation pattern, probably reflecting the different tumor types. Compound 13 accumulates rapidly in non necrotic MLS-mBanana tumors and then slowly clears out. In necrotic tumors the drug reaches maximum concentration in the viable margins within the first hour and then moves into the necrotic zone where it reaches maximum concentration at 24 h post administration. The rapid accumulation in MLS-mBanana at high concentrations, compared with MDA-MB-231-RFP possibly reflects a higher concentration of integrin receptors in MLS-mBanana cells.

The histology of large and small tumors from animals treated with compound 13 appears to support the suggested accumulation pattern and provide some clues to the underlying mechanism. There is a very good overlap between the viable tumor domain and compound 13 fluorescence in the first few hours, and a very good overlap between the fluorescence of 13 and the necrotic domains at 24 h and longer times post administration.

There are many reports on the accumulation of drugs and contrast agents in tumors related to poor lymphatic drainage and slow venous return. This phenomenon, termed enhanced permeability and retention (EPR) effect, has been previously suggested as a mean for targeting tumor tissue in a non specific way. It is possible that EPR accounts for compound 13 or compound 24 pattern of accumulation in the necrotic domain and non necrotic tumors. Serum albumin (SA)-drug complex permeation through the tumor vasculature into the interstitial tumor tissue was recently proposed to account for such accumulation (Tanaka, Shiramoto et al. 2004). There are several examples in the literature that have showed that conjugating molecules to SA resulted in the delivery of the molecule to the tumor and even into the necrotic domain. Indeed, negatively charged water-soluble Bchl derivatives were previously shown the present inventors to have high affinity to SA. Thus, the compound 13 or compound 24 probably associate to SA through the Bchl moiety after administration, circulate in the blood and extravagate with the SA into the tumor tissue by the EPR effect as explained above. In that case one expects accumulation of the compound 25 as a stand alone chemical entity in the necrotic area, however, since the retention of compound 25 in the studied tumors is short the possible accumulation by the EPR effect may be ruled out.

Alternatively, when the Bchl-RGD derivative encounters αVβ3 or αVβ5 integrins it should detach from the SA carrier and bind through the RGD part, to the integrin at a greater affinity than to the SA molecule. Following this primary attachment compound 13 or compound 24 can diffuse by endocytosis into the epithelial cells, or transcytosis across the epithelial cells. It is also possible that the drug moves directly to the extracellular matrix (ECM). In these cases the drug movement according to the concentration gradient will lean towards the necrotic region where the compound 13 or compound 24 is initially at its lowest concentration.

The proposed c(RGDfK)-2H/Pd-MLT interactions with integrin may imply that the accumulation in the tumor necrotic domain is neutrophils/macrophages depended. It is known for quite some time that activated neutrophils and macrophages expresses integrins. The histology results show that neutrophils reside in the necrotic domain (though mostly in the margins). It is known from the literature that there is high macrophages infiltration in invasive carcinoma of the breast (Leek, Landers et al. 1999). For NACAs (Necrosis Avid Contrast Agents) it was found that final clearance from the necrotic foci takes a few days after administration and corresponds to the natural healing process during which necrotic tissues are increasingly infiltrated and phagocytized by inflammatory cells, mostly neutrophils, monocytes, and/or macrophages, and replaced by granulation tissues. Therefore, the retained NACAs in necrosis are thought to be removed together with necrotic materials by phagocytosis. Thus, the secondary macrophage uptake after NACA-necrosis binding also may account for their local enrichment. Hence it is suggest that it is possible that the attraction to the necrotic domain and retention therein, rely on the attraction to the neutrophils and/or macrophages that are populating the necrotic domain.

The possible targeting and prolonged retention of fluorescence Chls/Bchls in the necrotic domain, may enable their early detection and help predicting tumor prognosis and modes of treatment. Moreover, it opens the way for the delivery of hypoxia triggered drugs.

The invention will now be illustrated by the following non-limiting examples.

EXAMPLES

Materials and Methods (i) Compounds—The Bchl derivatives, RGD-peptides and conjugates thereof were prepared as described in WO 2008/023378 of the same applicants. These conjugates and compounds are presented herein by the same Arabic numbers as in WO 2008/023378 (except compounds 45).

Compound 13 [c(RGDfK)-2H-MLT]: $3^1$-oxo-15-methoxycarbonylmethyl-Rhodobacteriochlorin $13^1$-(2-sulfoethyl) amide-$17^3$-c(RGDfK)amide potassium salt.

Compound 14 [c(RGDfK)-Mn-MLT]: Manganese (III) $3^1$-oxo-15-methoxycarbonylmethyl-Rhodobacteriochlorin $13^1$-(2-sulfoethyl)amide-$17^3$-(cycloRGDfK)amide potassium salt.

Compound 15 [c(RGDfK)-Cu-MLT]: Copper (II) $3^1$-oxo-15-methoxycarbonylmethyl-Rhodobacteriochlorin $13^1$-(2-sulfoethyl)amide-$17^3$-(cycloRGDfK)amide potassium salt.

Compound 24 [c(RGDfK)-Pd-MLT]: Palladium $3^1$-oxo-15-methoxycarbonyl-methyl-Rhodobacteriochlorin $13^1$-(2-sulfoethyl)amide-$17^3$-c(RGDfK)amide potassium salt.

Compound 25 [2H-MLT]: $3^1$-oxo-15-methoxycarbonylmethyl-Rhodo-bacteriochlorin $13^1$-(2-sulfoethyl) amide potassium salt.

Compound 26 [linear GRGDSP-2H-MLT]: $3^1$-oxo-15-methoxycarbonylmethyl-Rhodobacteriochlorin $13^1$-(2-sulfoethyl) amide-$17^3$-(GRGDSP)amide potassium salt.

Compound 36 [c(RGDyK)$_2$-2H-MLT]: $3^1$-oxo-15-methoxycarbonylmethyl-Rhodobacteriochlorin $13^1$-(2-sulfoethyl) amide-$17^3$-bis(cycloRGDfK)amide potassium salt.

Compound 45 [c(RADfK)-2H-MLT]: $3^1$-oxo-15-methoxycarbonylmethyl-Rhodobacteriochlorin $13^1$-(2-sulfoethyl) amide-$17^3$-(cycloRADfK)amide potassium salt.

(ii) Cell lines—MDA-MB-231 human breast cancer cells were obtained from the American Type Culture Collection (ATCC, Manassas, Va.). MLS-pRSETB-mBanana transfected human ovarian cancer cells resistant to puromycin were kindly provided by Prof. Michal Neeman (Department of Biological Regulation, Weizmann Institute of Science, Rehovot, Israel).

Figure 1B:
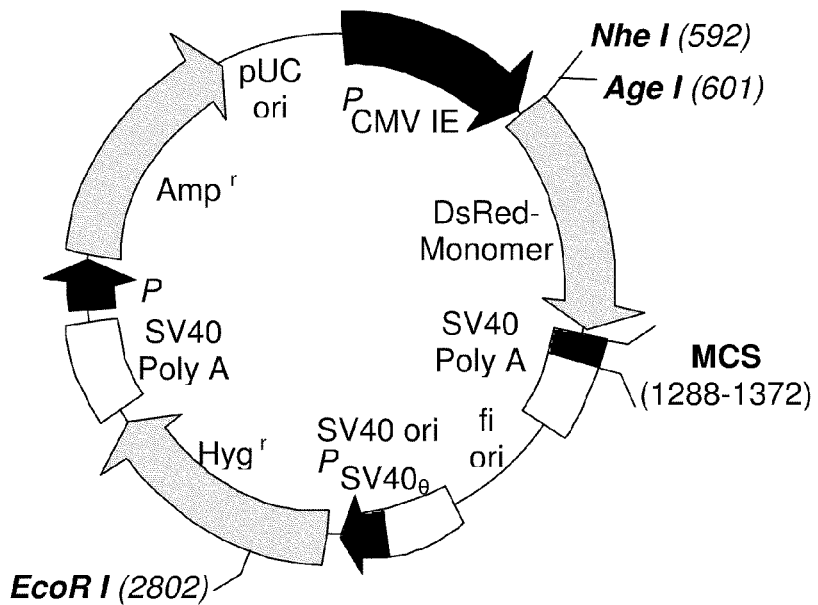

(iii) Transfection of MDA-MB-231 with red fluorescent protein (RFP)—Two plasmids were used for the transfection: pDsRed2-N1 (Clontech, Palo Alto, Calif.) (FIG. 1A) that carries the resistance gene for neomycin, and a modified pDsRed-Monomer-Hyg-C1 (Clontech, Palo Alto, Calif.) that carries the resistance gene for hygromycin, in which the DsRed-Monomer gene of the plasmid shown in FIG. 1B was replaced with pDsRed2 (from the pDsRed2-N1 plasmid, FIG.

1C). For the transfection, Lipofectamine™ 2000 (Invitrogen™) was used according to the manufacturer's protocol.

(iv) Tissue culture—MDA-MB-231-RFP cells were maintained in RPMI 1640 medium supplemented with 1 mmol/L sodium pyruvate, 10% fetal calf serum (FCS), 250 µg/ml hygromycin, 0.06 mg/ml penicillin and 0.1 mg/ml streptomycin. The cells were grown as monolayers at 37° C. in a humidified atmosphere (5% $CO_2$, 95% air). MLS-mBanana cells were maintained in MEM-α medium supplemented with 1 mmol/L sodium pyruvate, 10% fetal calf serum (FCS), 10 µg/ml puromycin, 0.06 mg/ml penicillin and 0.1 mg/ml streptomycin. The cells were grown as monolayers at 37° C. in a humidified atmosphere (5% $CO_2$, 95% air).

(v) Animals—Female CD1 nude mice (7-8 week old, ~25 g) were housed and handled with free access to food and water in the animal facility according to the guidelines (1996) of the Institutional Animal Care and Use Committee of the Weizmann Institute of Science (Rehovot, Israel).

(vi) Mouse tumor model—MDA-MB-231-RFP fluorescent human breast cancer cells and MLS-mBanana fluorescent human ovarian cancer cells ($5\times10^6$ in 100 µl saline) were trypsinated and collected at subconfluency and then inoculated into the back or mammary fat pad of female mice. Tumors were allowed to develop to two desired sizes—necrotic tumors (~1 $cm^3$, within 3-4 weeks) and non-necrotic tumors (~0.5 $cm^3$ within 1-2 weeks).

(vii) Whole body fluorescence imaging—Mice were anaesthetized by i.p. injection of 30 µl mixture of 85:15 ketamine:xylazine. For monitoring the drug accumulation in the mammary fat pad, mice were i.v. injected to the tail vein with 15 mg drug/kg body weight compound 13, compound 25 or compound 24. Red fluorescent protein (RFP), pRSETB-mBanana and the photosensitizers fluorescence were monitored by in-vivo optical imaging system, IVIS®100 (Xenogen Corp., Alameda, Calif.). Main filter set for tumor imaging comprised excitation filter at 500-550 nm and emission filter at 575-650 nm; Background filter set for subtracting tissue auto-fluorescence comprised excitation filter at 460-490 nm and emission filter at 575-650 nm. Drugs imaging main filter set comprised excitation filter at 665-695 nm and emission filter at 810-875 nm. Images were obtained during the same exposure time and are illustrated on the same linear color scale to allow for a qualitative comparison.

(viii) Fluorescence signal measurement in necrotic tumors—Tumor margins—region of interest (ROI), from the whole body in-vivo images was marked and the fluorescence signal within the circled margins was expressed in photon/sec.

The same ROI was used to measure photon/sec in the collateral side. In addition, for background measurements, tumor and collateral side ROIs were measured in three untreated mice and averaged. Measured values of the fluorescence from each ROI were divided by the area to provide normalized fluorescence signal intensity in photon/sec/$cm^2$. Signal measurements were collected from 15 min to 216 h post compound 13 injection. In each time point, the background was subtracted and the average was calculated as was the ratio between the fluorescence in the tumor margins and the collateral side.

(ix) Competition assay between compound 13 and free c(RGDfK) binding—Mice were injected with excess (8.5 µmol) of free c(RGDfK) peptide one hour prior to the injection of compound 13 (140 nmol). The control group was injected only with compound 13 (140 nmol). Fluorescent images were taken 24 h post compound 13 injection. Fluorescence imaging main filter set was used as described in (vii).

(x) Excised tumor fluorescence imaging—Mice were i.v. injected to the tail vein with 15 mg/kg compound 13. Mice were sacrificed, tumors were excised, cut in half and imaged at different time intervals: 10 min, 1, 4 and 24 h, 3, 5 and 7 days for MDA-MB-231-RFP and 7 days for MLS-mBanana using the Xenogen IVIS® System. Filter sets used for the fluorescence imaging are described in (vii).

(xi) Histology—Following the excision experiments, tumors were fixed in 3.7% formaldehyde and embedded in paraffin blocks. Sections were stained with hematoxylin-eosin (H&E) under standard conditions.

(xii) PDT Protocol—Anaesthetized mice were i.v. injected with 7.5 or 15 mg/kg compound 13. Tumors were illuminated for 10 or 30 min. The drug light interval was 8 or 24 h post drug injection. Transdermal illumination with 755 nm diode laser at 100 mW/$cm^2$ (CeramOptec, Germany) was used. In the dark control group, the mice were i.v. injected with the drug and placed in a dark cage for 24 h. In the light control group, the mice were not injected with the drug but were illuminated for 10 min with 100 mW/$cm^2$. During the first two days post PDT, the mice received analgesia as needed (2.5 mg/kg Flunexin daily).

Example 1

Transfection of Tumor Cells with Fluorescence Proteins

Figure 1C:
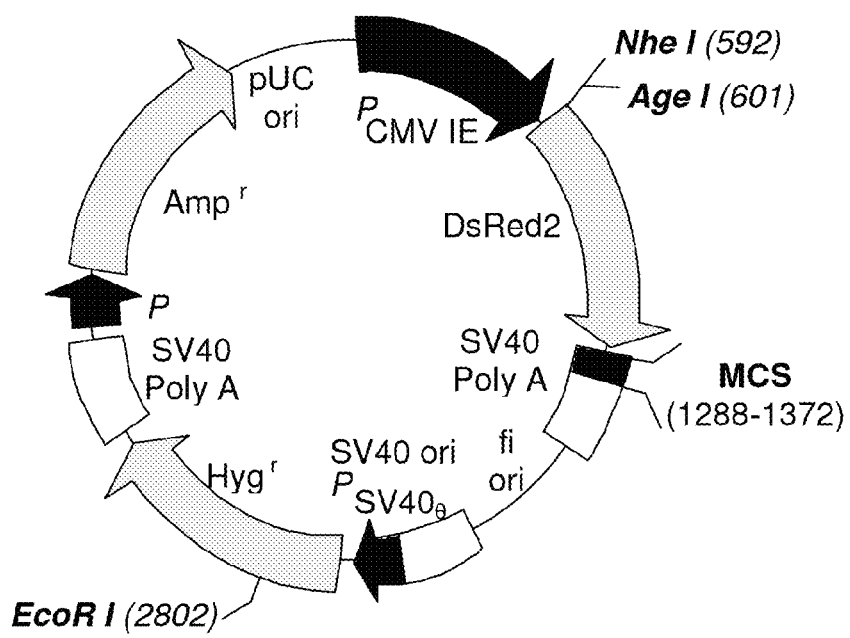
Figure 2A:
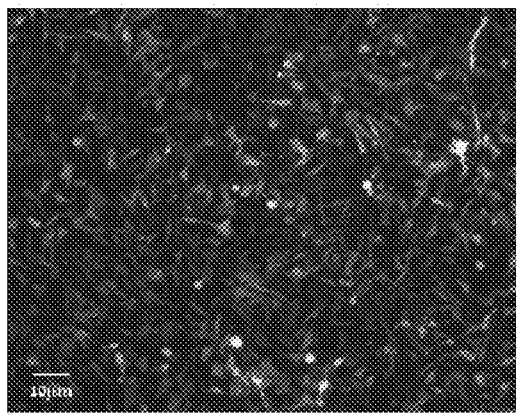
FIGS. 2A-2B show fluorescent clones of the transfected cells of FIG. 1 as detected by fluorescence microscope (Nikon, magnification X10) after 3 sec exposure. 2A: MDA-MB- 231 RFP clone 1 (resistant to G418). 2B: MDA-MB-231 RFP clone 3 (resistant to hygromycin).
Figure 2B:
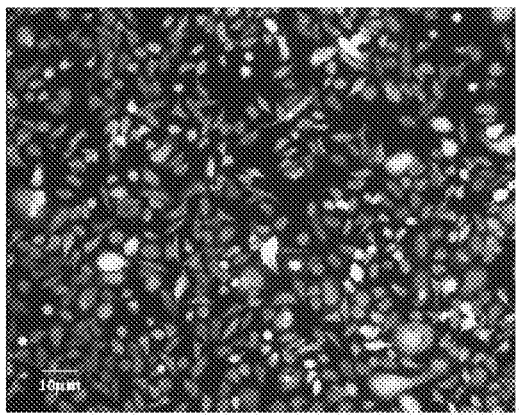

The transfection procedure was conducted in order to create a cell line that expresses RFP in a stable manner. Such a cell line can be detected by fluorescent microscopy and other fluorescence imaging means in vivo and in vitro (tissues/cells). The human breast cancer MDA-MB-231 cell line, known to generate spontaneous central necrosis, was chosen for this purpose. Two plasmids (FIGS. 1A, 1C) were used and stable clones were obtained and detected by fluorescence microscope (see FIGS. 2A-2B). The clones generated from the modified pDsRed-Monomer-Hyg-C1 plasmid (FIG. 1C) presented a stronger fluorescence. Clone 3 (FIG. 2B), transfected with modified pDsRed-Monomer-Hyg-C1, was chosen for further use.

The transfected cells expressed RFP constitutively with no reduction in the fluorescence intensity over time both in vitro and in vivo. Untransfected cells had no red auto fluorescence.

Example 2

Necrotic Tumor Model—Histopathological Analysis

Figures 3A, 3B:
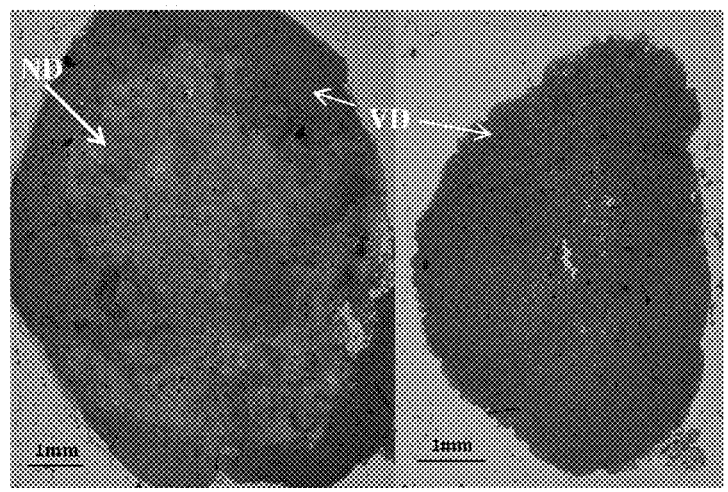
FIGS. 3A-3B show excised tumors images and histological analysis (H&E-staining) of MDA-MB-231-RFP tumors cross sections. 3A: large tumor (~1 cm$^3$). 3B: small tumor (~0.5 cm$^3$) (ND—necrotic domain, VD—viable domain).

In order to verify that MDA-MB-231-RFP cells generate a suitable necrotic model, MDA-MB-231-RFP tumors were allowed to develop into two sizes. Histological and histopathological analysis was carried out as described in Materials and Methods section (xi). Results are demonstrated in FIGS. 3A and 3B. Large tumors of ~1 $cm^3$ showed a very notable necrotic domain (FIG. 3A) whereas small tumors of ~0.5 $cm^3$ showed no necrotic domain (FIG. 3B).

Example 3

In-Vivo Fluorescence Imaging of Compound 13 Up-Take in Primary Necrotic MDA-MB-231-RFP Xenograft Tumors The accumulation pattern of compound 13 in necrotic MDA-MB-231-RFP tumors (≥1 $cm^3$) in vivo was examined. FIGS. 4A-4B and 5A-5B illustrate the accumulation of the fluorescence signal of compound 13 in orthotopic human breast MDA-MB-231-RFP primary tumor in the mammary pad of CD-1 nude female mice, using the Xenogen IVIS® System. Whole animal images were recorded concomitantly, using the filter sets as described in Materials and Methods section (vii) above. Dynamic fluorescence images were acquired every 1-1.5 h for 9 h, and at 24 h post injection of compound 13 (FIGS. 4A-4B), and then for every 24 h for the next 7 days (FIGS. 5A-5B). Shortly after injection of the compound 13, NIR fluorescence from the entire animal body could be detected, reflecting a high drug concentration in the circulation. Rapid clearance from the circulation, accompanied by accumulation in the liver, and to some extent in the tumor, were observed in the first 9 h after injection (FIG. 4B). In the following days, compound 13 kept accumulating in the tumor while completely clearing from the liver, providing a selective tumor imaging at >3 days to the end of the follow up period at 7 days post injection (FIG. 5B), and an extremely slow clearance thereafter. Tumor size and location did not change throughout the experiment as seen by the red in vivo whole body images (FIGS. 4A and 5A). Similar results were observed in 9 examined animals with tumor size of >1 cm$^3$.

Example 4

Figures 6A, 6B:
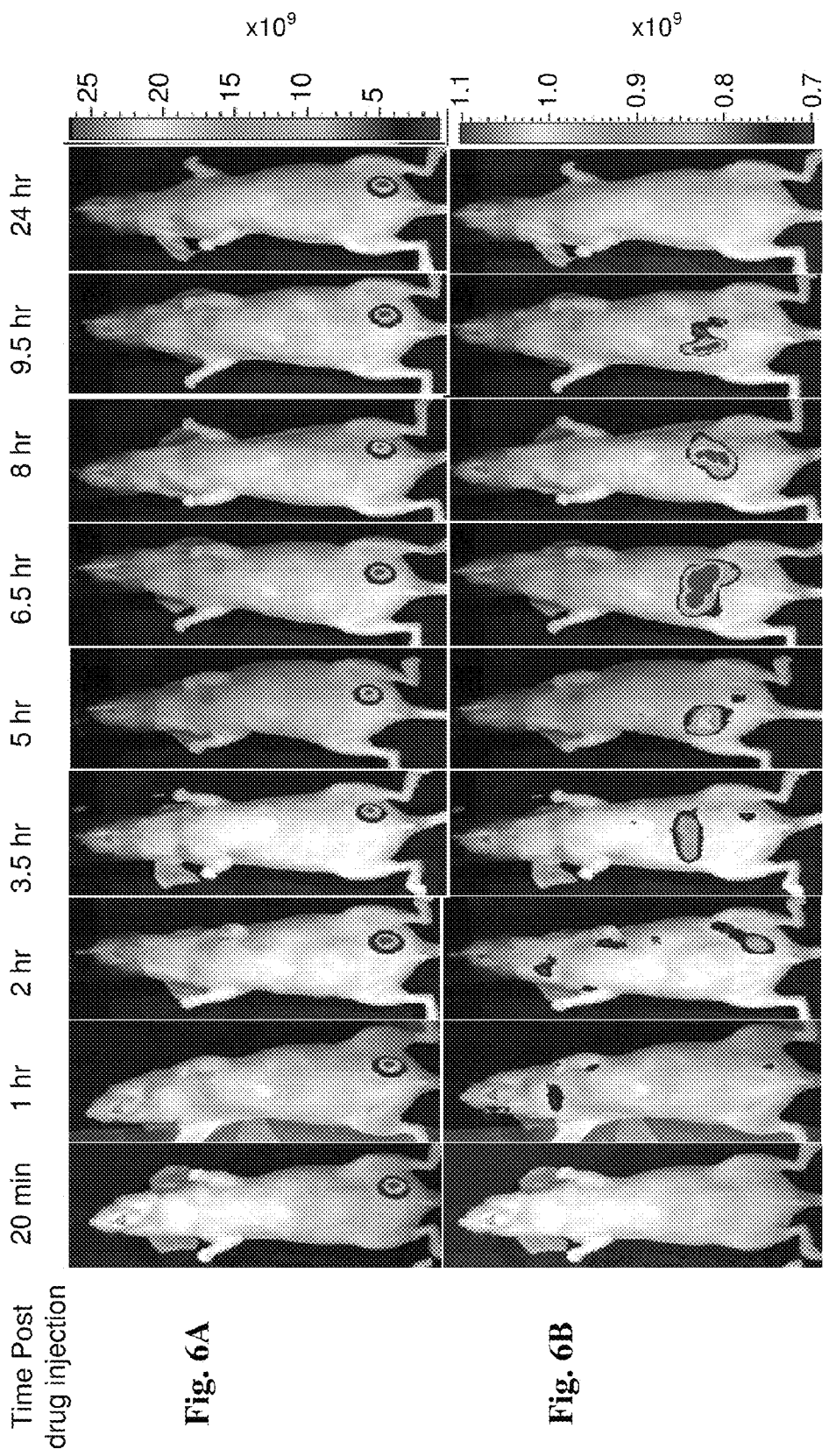
FIGS. 6A-6B show accumulation of compound 13 in MDA-MB-231-RFP orthotopic tumor (tumor size ~0.5 cm$^3$). Mice were injected with compound 13. Images were taken from 20 min to 24 h post drug injection. 6A (top panel): red fluorescence imaging. 6B (bottom panel): NIR fluorescence imaging.

In-Vivo Fluorescence Imaging of Compound 13 Up-Take in Primary Non-Necrotic MDA-MB-231-RFP Xenograft Tumors The same parameters were next examined in tumors ≤0.5 cm$^3$, which are non-necrotic. FIGS. 6A-6B and 7A-7B present the fluorescence signal from compound 13 and RFP in CD-1 nude female mice that were grafted with MDA-MB-231-RFP. The pattern of drug accumulation was imaged using the IVIS® system as described above, and at similar time intervals as in Example 3, but limited to 3 days because of a complete drug clearance by that time. The accumulation pattern in these non-necrotic tumors was markedly different from that observed in the necrotic tumors. The compound 13 NIR fluorescence reached peak values in the tumor at ~2 h post injection and shortly after in the liver (3.5 h post drug injection) (FIG. 6B). In contrast to the resolved fluorescence of compound 13 from necrotic tumors, practically no fluorescence could be observed 2 days post injection from the non-necrotic tumors (FIG. 7A). In averaged measurements of fluorescence from 16 animals, peak tumor fluorescence was detected at 1-6.5 h post drug injection.

Example 5

Kinetics of Compound 13 Uptake and Clearance in MDA-MB-231-RFP Necrotic Tumors

Figure 8:
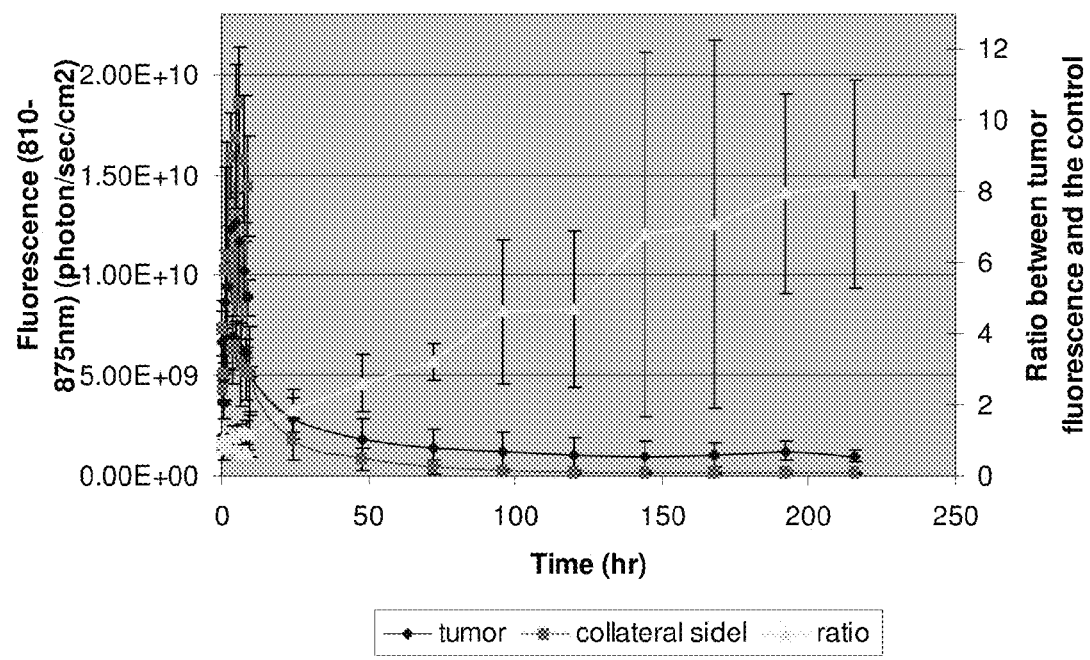
FIG. 8 is a graph showing compound 13 fluorescence signal measurement in the tumor vs. collateral side. Fluorescence signal in photon/sec/cm$^2$ was measured in 9 animals for both the tumor and the collateral side. Results were collected from 15 min to 216 h post compound 13 injection. The average result for all animals in each time point is presented as well as the ratio of the fluorescence between the tumor and the collateral side.

In order to evaluate semi-quantitatively the accumulation pattern of compound 13 in necrotic tumors, the average fluorescence signal for compound 13 in necrotic tumors of 9 mice was calculated and plotted over 216 h, at several time points (FIG. 8). From 12 h post injection and onward the fluorescence signal from the tumor became distinctively stronger than that of an equivalent control region on the collateral side. The ratio of the fluorescence between the tumor and the collateral side increased in time and reached a plateau at ~8 from 192 h.

Example 6

Up Take of Compound 24 in Orthotopic MDA-MB-231-RFP Primary Necrotic Xenograft Tumors The in vivo accumulation pattern of the metalated conjugate compound 24 (c(RGDfK)-Pd-MLT) in necrotic primary MDA-MB-231-RFP tumor was examined using the same set of experiments described in Example 3.

Results shown in FIGS. 9A-9B and 10A-10B, demonstrate that fluorescence could be detected shortly after injection of compound 24, reflecting a high drug concentration in the circulation. Rapid clearance from the circulation accompanied by accumulation in the liver, and to some extent in the tumor, was observed in the first 8 h after injection (FIG. 9B). In the following days, compound 24 kept accumulating in the tumor, however, no complete clearance from the liver was observed (FIG. 10B). It appears that compound 24 can act as a selective imaging molecule for the tumor from ~3 days post injection with an extremely slow clearance thereafter. However, it is somewhat less specific then compound 13. Tumor size and location did not change throughout the experiment as seen by the red in vivo whole body images (FIGS. 9A and 10A). These results, with tumor size of >1 cm$^3$ were observed in 3 animals.

Example 7

Up Take of Compound 24 in Orthotopic MDA-MB-231-RFP Primary Non-Necrotic Xenograft Tumors The fluorescence signal from compound 24 and RFP was further examined in MDA-MB-231-RFP non-necrotic tumors (~0.5 cm$^3$) grafted on CD-1 nude female mice as described in Example 4 above, using similar time intervals as indicated in Example 6, but limited to 2 days because of a complete drug clearance from the tumor by that time. Results presented in FIGS. 11A-11B and 12A-12B, demonstrate that, as for compound 13, the accumulation pattern in non-necrotic tumors was markedly different from that observed in the necrotic tumors. The compound 24 NIR fluorescence reached peak values in the tumor at ~2.5 h post injection and shortly after in the liver (5.5 h post drug injection, FIG. 11B). In contrast to the resolved fluorescence of compound 24 from necrotic tumors, practically no fluorescence could be observed 24 hours post injection from the non-necrotic tumors (FIG. 12B). Peak tumor fluorescence (fluorescence average measurements from 5 animals) was detected at 1-4.5 h post drug injection.

Example 8

Uptake of Compound 13 in MLS-mBanana Primary Necrotic Tumors Implanted in the Mouse Mammary Pad In order to establish the generality of the results obtained in the experiments above, the accumulation of compound 13 in the necrotic domain was further examined in a different tumor type, generated from MLS-mBanana human ovarian cancer cell line. Results shown in FIGS. 13A-13B and 14A-14B, illustrate the accumulation of the fluorescence signal from compound 13 in subcutaneous (s.c.) human ovarian MLS-mBanana primary tumors that were grafted in the mammary pad of CD-1 nude female mice, using the Xenogen IVIS® System as described in Material and Methods, section (vii). The pattern of accumulation was monitored at similar time intervals as described herein above in Example 3, limited to 4 days because of a complete drug clearance by that time. Shortly after injection, the compound 13 NIR fluoresces was mostly detected from the liver and the tumor. Rapid clearance from the circulation accompanied by accumulation in the liver, and the tumor, occurs in the first 8 h after injection (FIG.

13B). After 2 days, compound 13 kept accumulating in the tumor while completely clearing from the liver, providing a selective imaging of the tumor with no surrounding interference (FIG. 14B). The clearance from the MLS-mBanana necrotic tumors was markedly faster than the clearance from the MDA-MB-231-RFP necrotic tumors, and was almost completed at day 3. Tumor size and location did not change throughout the experiment as seen by the red in-vivo whole body images (FIGS. 13A and 14A). These results were observed in 3 animals with tumor size >1 cm$^3$.

Example 9

Uptake of Compound 13 in MLS-mBanana Primary, Non-Necrotic Tumors Implanted in the Mouse Mammary Pad In view of the results in non-necrotic MDA-MB-231-RFP tumors showing no prolonged drug accumulation, the prolonged accumulation in MLS-mBanana non-necrotic tumors was examined. Results shown in FIGS. 15A-15B and 16A-16B, present the fluorescence signal from compound 13 in MLS-mBanana non-necrotic tumors. The pattern of accumulation was monitored as described in Materials and Methods, section (vi) using similar time intervals as described in Example 4, limited to 4 days because of almost complete drug clearance by that time. The accumulation pattern in non-necrotic tumors was somewhat similar to that of necrotic tumors. The compound 13 NIR fluorescence reached peak values in the tumor at ~1 h post injection (FIG. 15B). Accumulation in the liver was detected from the first hour.

Figures 17A, 17B:
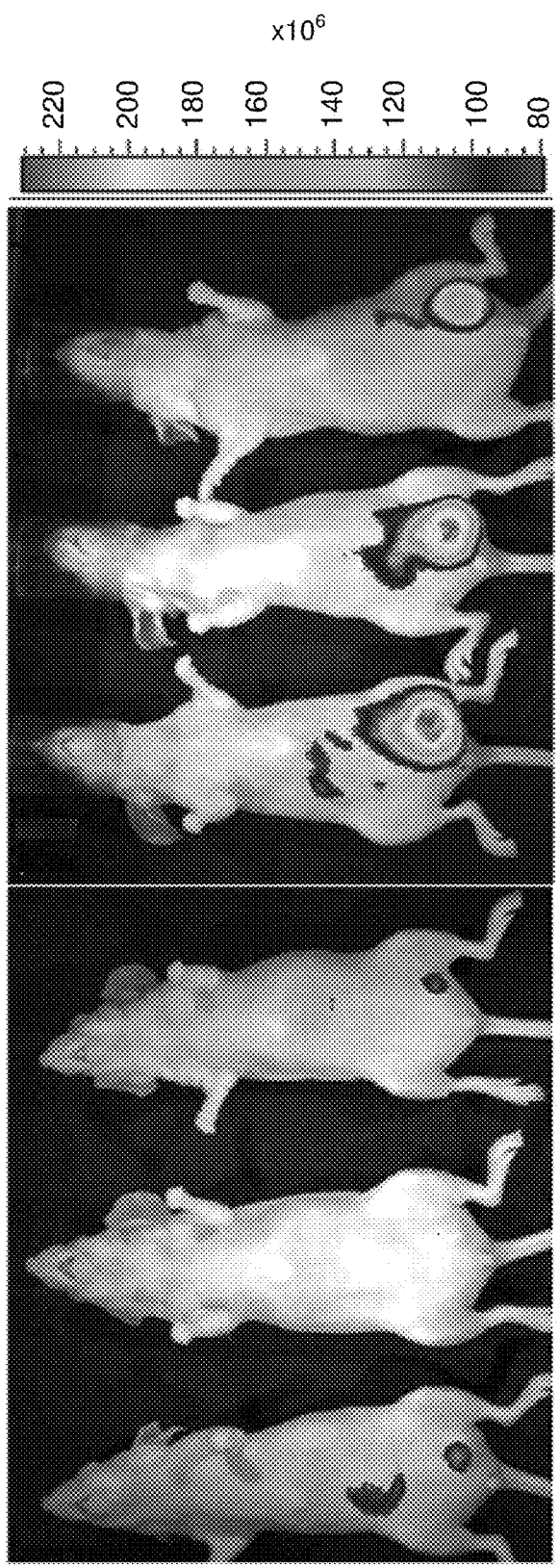
FIGS. 17A-17B demonstrate comparison of compound 13 accumulation in human ovarian MLS-mBanana primary necrotic and non-necrotic tumors. Images were taken 2 days post compound 13 injection. Images of in-vivo whole-body NIR fluorescence of compound 13 were taken. 17A: Non-necrotic tumors (~0.5 cm$^3$). 17B: Necrotic tumors (~1 cm$^3$).

When comparing necrotic and non-necrotic tumors on the same linear fluorescence scale, the compound 13 concentration in the necrotic tumors appears to be much higher than that in the non-necrotic ones as shown in FIGS. 17A-17B. Peak tumor fluorescence (fluorescence average measurements from 4 animals) was detected at 1-3.5 h post drug injection.

Example 10

The Dependence of Compound 13 Accumulation on the c(RGDfK) Moiety

Two experiments were performed in order to determine whether the tumor up-take of compound 13 and the resulted accumulation of the NIR fluorescence signal are driven by the RGD moiety. In the first experiment the accumulation of the fluorescence signal at different times after compound 13 injection was compared to that of free 2H-MLT (compound 25) injection to CD1-nude mice grafted with MDA-MB-231-RFP non-necrotic (≤0.5 cm$^3$) and necrotic (~1 cm$^3$) tumors at the mammary pad. The second experiment was a competition assay between compound 13 and free c(RGDfK).

Figures 18A, 18B:
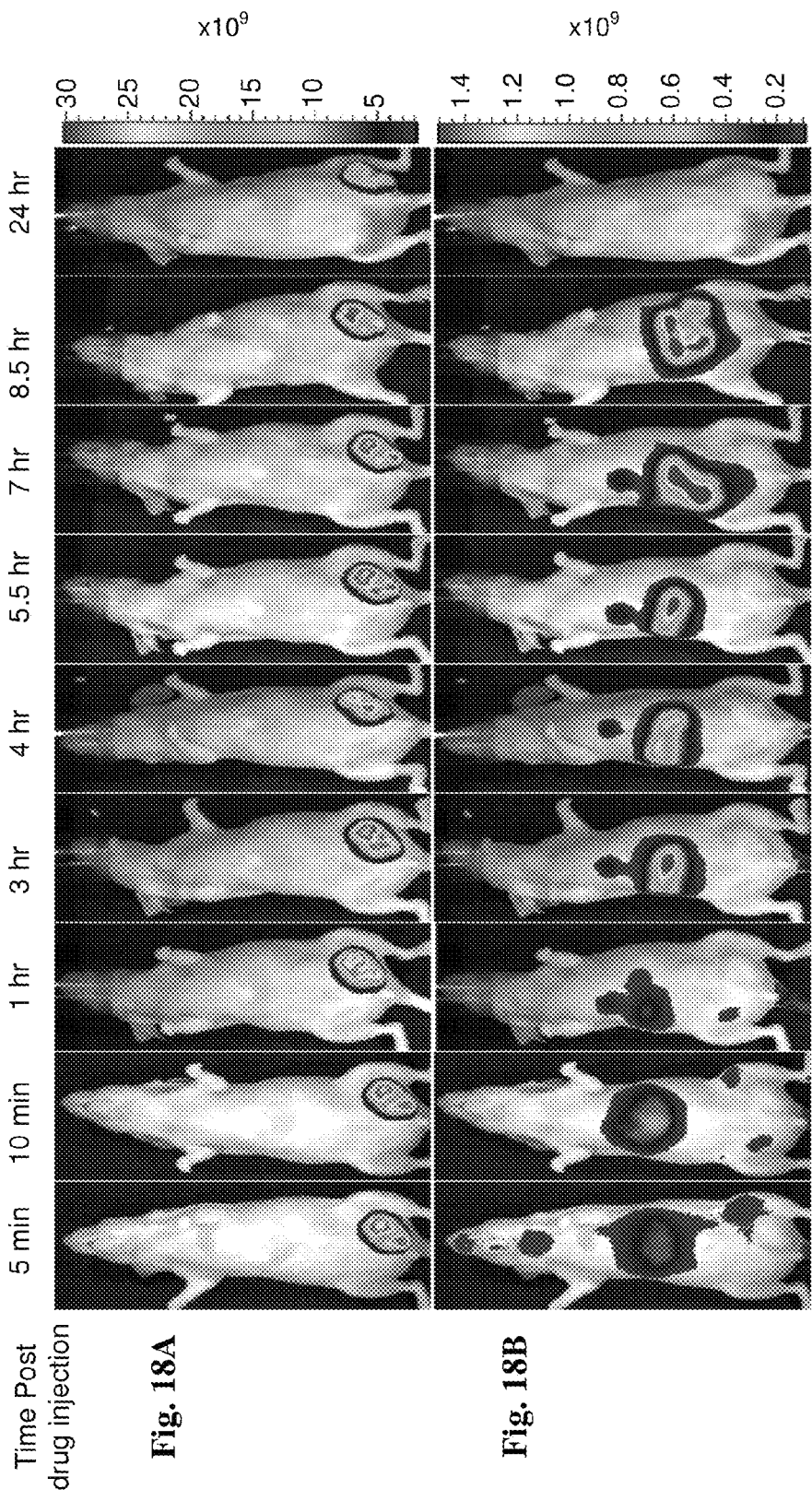
FIGS. 18A-18B show accumulation of compound 25 in MDA-MB-231-RFP orthotopic tumor (tumor size ~1 cm$^3$). Mice were injected with compound 25 and images were taken from 5 min to 24 hours post drug injection. 18A (top panel): red fluorescence imaging. 18B (bottom panel): NIR fluorescence imaging.
Figures 20A, 20B:
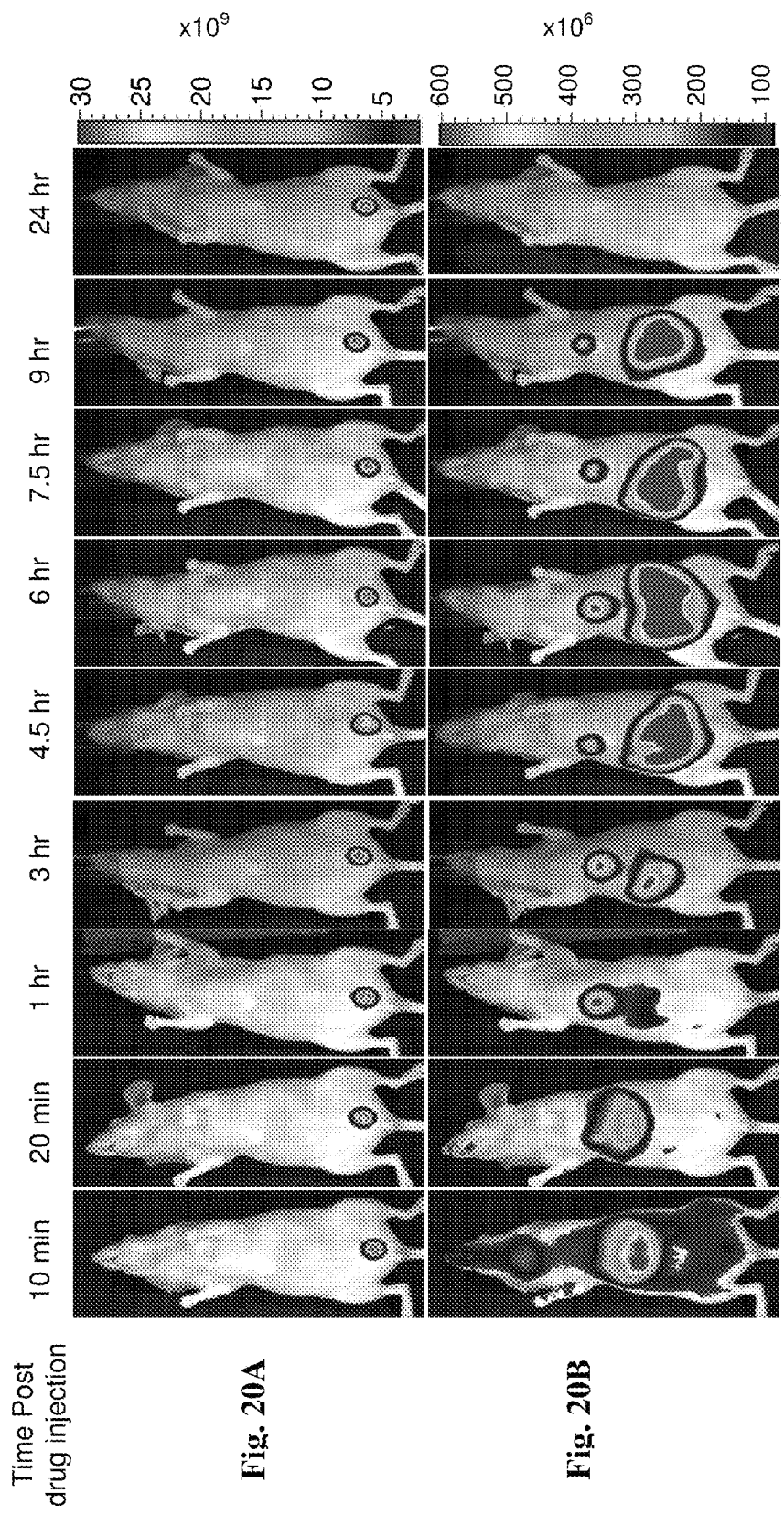
FIGS. 20A-20B show accumulation of compound 25 in MDA-MB-231-RFP orthotopic non-necrotic tumor (tumor size ~0.5 cm$^3$). Mice were injected with compound 25, and images were taken from 10 min to 24 hours post drug injection. 20A (top panel): red fluorescence imaging. 20B (bottom panel): NIR fluorescence imaging.

10.1 Uptake of Compound 25 in MDA-MB-231-RFP Primary, Necrotic and Non Necrotic Tumors Dynamic fluorescence images were acquired for both necrotic and non necrotic tumors every 1-1.5 h for 8.5-9 h, and at 24 h after initial injection of compound 25 (FIGS. 18A-18B and 20A-20B) and for every 24 h for the following three days (FIGS. 19A-19B and 21A-21B). The compound 25 NIR fluorescence signal reached a maximal concentration in the tumor at 5-10 min post injection, if any concentration was observed at all. The fluorescence signal values were ~2 orders of magnitude smaller than the maximally observed values for compound 13 (at much longer time intervals). The fluorescence signal dropped down to non-significant values already at 20 min post injection. Meanwhile, the fluorescence signal accumulated mostly in the liver and in the heart. The same behavior was observed in 3 animals with necrotic tumors (FIG. 18B) and in 2 animals with non-necrotic tumors (FIG. 20B).

10.2 Competition Assay Between Compound 13 and Free c(RGDfK) Binding to MDA-MB-231-RFP Primary Non-Necrotic Tumors Experiments attempted to block compound 13 accumulation by free c(RGDfK) ligand were performed in order to prove specific binding. Compound 13 was administrated with or without prior injection of c(RGDfK) as described in Example 3. Results are demonstrated in FIGS. 22A-22D. When compound 13 was administrated after free c(RGDfK) administration, no accumulation in the tumor was detected after 24 h (FIG. 22C), whereas when compound 13 was administrated alone, in the control group, accumulation in the tumor was detectable (FIG. 22D), indicating specific binding of compound 13 to the tumor, via the c(RGDfK) moiety.

Example 11

Specific Accumulation of Compound 13 in MDA-MB-231-RFP Necrotic Tumor Domains

The markedly different dynamic fluorescence patterns of necrotic and non-necrotic breast tumor xenografts implanted in the mammary pads, motivated investigation of the correlation between the tumor histology and compound 13 fluorescence signal accumulation. Hence, tumors were excised at indicated times after injection of compound 13 and cut in half. Images were taken at several time points (10 min, 1, 4 and 24 h, 3, 5 and 7 days post injection) using Xenogen IVIS® System as described in Materials and Methods, section (vii). Results shown in FIGS. 23-29 present compound 13 fluorescence accumulation at different time points. For each time point, 3 animals were tested. From 10 min to 4 h post drug injection, the drug fluorescence was observed only at the viable area (FIGS. 23-25). At 4 h, there was some diffusion towards the necrotic domain. From three days post injection the pattern of accumulation reverted: the fluorescence shifted completely to the necrotic zone with some residual fluorescence diffusion towards the surrounding viable cells (FIG. 27F). These results were observed for five and seven days as well (FIGS. 28-29). Importantly, at 24 h post injection, specific tumor fluorescence was already clearly observed with higher drug fluorescence from the necrotic domain but the tumor boundaries were less sharply defined compared with the three days interval (FIG. 26F). In this set of experiments it was shown that as time progresses, compound 13 moves through the viable domain into the necrotic domain and accumulates there specifically for a long period of time.

Example 12

Specific Accumulation of Compound 24 in MDA-MB-231-RFP Necrotic Tumor Domains

In view of the pattern of accumulation observed for compound 13, other Bchl derivatives were tested. The pattern of accumulation of compound 24 was monitored and obtained similar results were obtained. The results for tumors excised 9 days post drug injection are presented in FIGS. 30A-30F. Images were taken using Xenogen IVIS® System as described above. As seen in FIG. 30F, nine days post drug injection the drug was clearly present in the necrotic domain of the tumor. These results were observed in all animals examined (N=3). Similar results were observed when tumors were excised 3 and 5 days post drug injection (N=3 for each time point).

Example 13

Specific Accumulation of Compound 13 in MLS-mBanana Necrotic Tumor Domains

The observed accumulation of both compound 13 and compound 24 in the necrotic domain of MDA-MB-231-RFP tumors, provided a motivation to examine the generality of this phenomenon and its potential application in therapeutics and imaging. Hence, a different type of tumor—MLS-mBanana human ovarian cancer, was used. Here the results were somewhat different. In most cases the necrosis pattern in this type of tumor was not central, namely, there was a wide spread necrosis that was not specifically located in the middle of the tumor or generated from one place in the tumor. In these cases, the accumulation was not as prolonged. In the few cases where central necrosis was observed, the accumulation pattern was similar to that in the MDA-MB-231-RFP tumors. FIGS. 31-32 show the results obtained 7 days post drug injection. As seen, the drug was clearly present in the necrotic domain of the tumor, when central necrosis was observed (FIG. 31F) and not present where there was no central necrosis (FIG. 32F).

Example 14

Excised Tumor Image and Histological Sections of Necrotic Tumors

MDA-MB-231-RFP necrotic tumor was excised and histological sections of the tumor were stained (hematoxylin and eosin (H&E)). FIGS. 33A-33D show histological sections of the tumor viable and necrotic domains of tumor excised 4 hours after drug injection. These observations should complement the RFP and compound 13 tissue distribution imaging previously obtained. As seen in FIG. 33A, the balk of the mass is composed of opaque, tan and necrotic tissue. From FIG. 33B, a correlation between the macroscopic and microscopic features can be noted. The necrotic tissue at the center was eosinophilic to hypereosinophilic with widespread karyolysis and lesser pyknosis and karyorrhexis. There was mild multifocal neutrophilic infiltration into the necrotic tissue, mostly at the margins of the necrotic domain. Viable areas were limited to the periphery of the tumor. They were composed of disorganized proliferation of neoplastic cells arranged into densely cellular sheets (FIG. 33D). The neoplastic cells were round to irregular with a high nuclear:cytoplasmic ratio and irregular vesicular nuclei. The fluorescence of compound 13 at 4 h post injection corresponded nicely to the histological results, for both viable and necrotic domains (FIG. 25F). Similar correlation was obtained for all examined necrotic tumors, including control tumors that were not injected with the drug.

Example 15

In-Vivo PDT Studies Using Compound 13

Generally, for in vivo PDT studies mouse tumor models are generated by inoculating fluorescent MDA-MB-231-RFP breast cancer cells or MLS-mBanana ovarian cancer cells subcutaneously on the back or mammary fat pad of female mice as described above, and allowed to grow to necrotic (>1 cm$^3$) or non-necrotic (~0.5 cm$^3$) size. Anaesthetized mice are injected i.v. with the drug at different concentrations between 7.5-15 mg/kg. The tumors are illuminated for 10 or 30 min, and the drug light interval is between 4-24 h post drug injection.

Several protocols examining the effect of compound 13 on MDA-MB-231-RFP tumors in nude CD-1 mice, were applied in order to obtain optimal treatment conditions, and the results are summarized in Table 1.

As seen in Table 1, it appears that 7.5 mg drug/kg body and 10 min illumination provides the best photodynamic treatment results for both necrotic and non-necrotic tumors. Results shown in FIG. 34A-34B demonstrate a full cure on a non-necrotic MDA-MB-231-RFP tumor. One day after treatment edema was detected, followed by mild and then more extensive necrosis in the following 4 days. By day 7, tumor flattering was observed. The wound healed and the animal was cured 90 days post PDT. The results were also examined using the Xenogen IVIS® System as previously described for the fluorescence of RFP. After 90 days there was no tumor fluorescence signal.

TABLE 1

Results of PDT protocols for treating MDA-MB-231-RFP tumors.

| Tumor type | Treatment time (hours) | Dose (mg/kg) | Duration of illumination (min) | Intensity of illumination (mW) | Comments | No. animals |
|---|---|---|---|---|---|---|
| Non-necrotic | 8 | 15 | 10 | 100 | Death with treatment | 5 |
| | 24 | 15 | 30 | 280 | No response | 3 |
| | 8 | 7.5 | 10 | 100 | Full response | 4 |
| | | | | | Limited necrosis and regrowth | 3 |
| | | | | | No response | 1 |
| | | | | | Death with treatment | 3 |

TABLE 1-continued

Results of PDT protocols for treating MDA-MB-231-RFP tumors.

| Tumor type | Treatment time (hours) | Dose (mg/kg) | Duration of illumination (min) | Intensity of illumination (mW) | Comments | No. animals |
|---|---|---|---|---|---|---|
| Necrotic | 8 | 7.5 | 10 | 100 | Full response | 1 |
| | | | | | Limited necrosis and regrowth | 3 |

Example 16

Establishing Localized Ductal Carcinoma In Situ (DCIS) Model in the Mammary of Nude Mice/Rats Several cell lines are used to establish the DCIS model in mice and rats. First, MADB106 cells that are syngeneic with F-344 rats have already been successfully implanted (orthotopic), to the rat's mammary pad. This model has so far been used to screen the efficacy of PDT with different RGD-Bchl derivatives and the subsequent development of anti-tumor, long-term immunity. The same protocol as for rat mammary carcinoma tumors is used to implant two human cell lines and an additional mouse cell line orthotopically and to obtain metastases in lungs and lymph nodes. The first two, hT47D and HCC1395, are ductal carcinoma cell lines (HCC1395 is a primary ductal carcinoma of stage 1, which is as close as possible to DCIS) that are grown according to ATCC regulations and the literature (Gazdar et al., 1998), and are injected as allografts to the mammary pad of the nude animals. The third (4T1) is a mouse mammary cell line that generates lung metastases a few weeks after cells injection to the tail vein. This variety of cell lines enables us to study the effect of (Bchl derivatives/Bchl-RGD)-PDT on primary lesions, locally recurred ones and remote metastases of mammary carcinoma as breast cancer models. The 4T1 cells are transfected with luciferase as well as the other two cell lines. Transfection of 4T1 with pDsRed1-C1 is currently in progress. Such fluorescence enables: (1) Assessment of detection accuracy using Bchl-RGD based fluorescence or MRI; (2) On-line monitoring of tumor growth and regression under Bchl-PDT in intact animals at a very high sensitivity.

Example 17

Establishing the Necrosis Accumulation Concept as a General Concept

There are tumor types that develop central necrosis upon development. Two such tumors are selected for examination from tumors developed from the following cell lines: human DCIS MCF7 breast cancer, human DCIS MCF10DCIS (Tait et al., 2007), human glioblastoma U87, human inflammatory breast cancer (IBC) WIBC-9 (Shirakawa et al. 2001) and RCC.

The selected cell lines undergo transfection using the modified pDsRed-Monomer-Hyg-C1 plasmid and Lipofectamine™ 2000 Transfection Reagent (Invitrogen™) as described in Materials and Methods, section (iii) above. Cells are implanted (1-5×10$^6$ cells, according to the requirements for each cell type) orthotopically, if possible, or s.c. in CD-1 nude mice, allowed to grow to the desired limit size (about 1 cm$^3$) and develop necrosis. Necrotic region is followed histologically. Two suitable tumor models developed from the above cell lines are selected for further study based on parameters of necrotic zone, growth rate, and imaging.

For whole body fluorescence imaging, mice are anaesthetized as described above and compound 13 is injected i.v. to the tail vein (15 mg/kg). Fluorescence of the drug and the tumor is monitored by IVIS®100 Imaging system (Xenogen) as described above.

For excised tumor fluorescence imaging, mice are injected i.v. to the tail vein with 15 mg/kg compound 13. Mice are then sacrificed at different time points, and tumors are excised and cut in half. Imaging of the excised tumors and their histologic staining for evaluating necrotic domains are conducted according to Materials and Methods, sections (x) and (xi) above. Accumulation of compound 13 in the central necrotic domains of the tumors is expected, independent of the cell line origin.

Example 18

Accumulation Pattern of Compound 25 Conjugated to Different RGD Moieties

To further establish the relevance of the RGD targeting, different RGD peptides and negative controls are used to examine the pattern of accumulation in MDA-MB-231-RFP tumors.

MDA-MB-231-RFP cells are implanted (5×10$^6$ cells) orthotopically in CD-1 nude female mice and allowed to grow to a necrotic size of 1 cm$^3$. Mice are anaesthetized and injected i.v. to the tail vein with 15 mg/kg of compound 26 (linear GRGDSP-2H-MLT), compound 45 (c(R ADfK)-2H-MLT) and compound 36 (c(RGDyK)$_2$-2H-MLT). In vivo fluorescence of the drug in the intact animal and excised tumor fluorescence imaging and histology are carried out as described above in Materials and Methods, sections (vii), (x) and (xi), respectively.

Example 19

Accumulation of Other Bchl-RGD Derivatives in the Necrotic Area

Additional Bchl-RGD derivatives are examined in order to investigate whether the accumulation pattern in necrosis is a general paradigm for all Bchl-RGD derivatives that have therapeutic and/or imaging potential. Specifically, compound 15 (c(RGDfK)-Cu-MLT) and compound 14 (c(RGDfK)-Mn-MLT) derivatives are examined.

MDA-MB-231-RFP cells are implanted (5×10$^6$ cells) orthotopically, in CD-1 nude female mice and allowed to grow to a tumor size of 1 cm$^3$.

In case where the Bchl fluorescence is quenched because of metallation (e.g. Cu and Mn), the compounds concentrations in the tumor and non tumor tissues are determined by Inductively-Coupled Plasma Mass Spectrometry (ICP-MS), using an ELAN-6000 instrument (Perkin Elmer, CT) as described by Brandis et al. (Brandis et al., 2005).

Example 20

Biodistribution Assays

This experiment aims at quantifying the course of drug spread and accumulation in various organs of the body, and demonstrating in an un-biased way that the drug indeed accumulates eventually in the tumor.

Anaesthetized mice bearing MDA-MB-231-RFP tumors are injected i.v. with compound 13, 15 mg/kg. Mice are sacrificed at several time points after injection. Tissues (blood, kidneys, liver, skin, fat, muscle, spleen, intestine, brain, heart, lungs and tumor) are collected into pre-weighted vials and frozen. Tissue samples are homogenized and the drug is extracted in methanol (~1 ml methanol per 100 mg tissue). Samples are then analyzed for drug content by fluorescent analysis.

Quantification of compound 13 accumulation in the various tissues is performed by fluorescence intensity measurements, and assessing the drug concentration using, as reference, a calibration curve obtained by measuring the florescence intensity of different concentrations of compound 13 in ethanol. In vivo NIR fluorescence images obtained in Example 3 above at various time points are compared with the fluorescence intensity of the extracts from the biodistribution assay. The results are used to validate the in-vivo measurements.

It is expected to find linear correlation between the in vivo and in vitro fluorescence measurements. It is also expected that the quantitative analysis will show more accurately the different accumulation and clearance from tumor and normal tissues. Such determination may be very useful for the clinical arena.

Example 21

Metalated RGD-Bacteriochlorophyll Derivatives with a Radio-Isotope for Imaging and Therapy Another therapeutic option is the replacement of the central metal of the drug with a radioactive one. Accumulation of such an RGD-M-Bchl derivative where M has a relatively long lifetime (for therapy) can be used for radiotherapy of the tumor. The drug could also be administrated in such intervals in which the drug stays at low concentrations in the body but is increasingly accumulated in the necrotic region.

Cu incorporation to the drug is performed by a method developed in the laboratory of the present inventors that allows quantitative metallation of 2H-Bchl-RGD within 10-20 min at ambient temperature. The obtained compound is very stable and no demetallation occurs under physiological conditions.

It is expected to demonstrate accumulation of the radioactive compound in the tumor tissue and to observe tumor regression after one or two treatments.

References

Alfsen, A., H. Yu, et al. (2005). "HIV-1-infected blood mononuclear cells form an integrin- and agrin-dependent viral synapse to induce efficient HIV-1 transcytosis across epithelial cell monolayer." Mol Biol Cell 16(9): 4267-79.

Becker, A., B. Riefke, et al. (2000). "Macromolecular contrast agents for optical imaging of tumors: comparison of indotricarbocyanine-labeled human serum albumin and transferrin." Photochem Photobiol 72(2): 234-41.

Berton, G. and C. A. Lowell (1999). "Integrin signalling in neutrophils and macrophages." Cell Signal 11(9): 621-35.

Bijker N et al. (2006) "Breast-conserving treatment with or without radiotherapy in ductal carcinoma-in-situ: ten-year results of European Organisation for Research and Treatment of Cancer randomized phase III trial 10853"—a study by the EORTC Breast Cancer Cooperative Group and EORTC Radiotherapy Group. J Clin Oncol. 24(21):3381-7

Boehm-Viswanathan T. (2000) "Is angiogenesis inhibition the Holy Grail of cancer therapy?" Curr Opin Oncol. 12(1): 89-94

Brandis A., Mazor O., Gross S., Koudinova N., Hami R., Kalin-Kammhuber N., Rosenbach-Belkin V., Greenwald M., Bondon A., Simonneaux G., Scheer H., Salomon Y. and Scherz A. (2003) "Novel palladium-bacteriochlorophyll derivatives for antivascular Photodynamic therapy: synthesis, phototoxicity, pharmacokinetics and efficacy", J. Med. Chem. submitted.

Brandis, A., O. Mazor, et al. (2005). "Novel water-soluble bacteriochlorophyll derivatives for vascular-targeted photodynamic therapy: synthesis, solubility, phototoxicity and the effect of serum proteins." Photochem Photobiol 81(4): 983-93.

Britton M M. (2006) "Nuclear magnetic resonance studies of convection in the 1,4-cyclohexanedione-bromate-acid reaction. J Phys Chem A." 110(15):5075-80.

Brown, J. M. and A. J. Giaccia (1998). "The unique physiology of solid tumors: opportunities (and problems) for cancer therapy." Cancer Res 58(7): 1408-16.

Brown, J. M. and W. R. Wilson (2004). "Exploiting tumour hypoxia in cancer treatment." Nat Rev Cancer 4(6): 437-47.

Brown, N. S. and R. Bicknell (2001). "Hypoxia and oxidative stress in breast cancer. Oxidative stress: its effects on the growth, metastatic potential and response to therapy of breast cancer." Breast Cancer Res 3(5): 323-7.

Burstein H J, Polyak K, Wong J S, Lester S C, Kaelin C M. (2004) "Ductal carcinoma in situ of the breast." N Engl J Med. 350(14):1430-41. Review Bussolati, G., M. Bongiovanni, et al. (2000). "Assessment of necrosis and hypoxia in ductal carcinoma in situ of the breast: basis for a new classification." Virchows Arch 437(4): 360-4.

Cao, Y. (2005). "Tumor angiogenesis and therapy." Biomed Pharmacother 59 Suppl 2: S340-3.

Cellini C, Huston T L, Martins D, Christos P, Carson J, Kemper S, Simmons R M. (2005) "Multiple re-excisions versus mastectomy in patients with persistent residual disease following breast conservation surgery." Am J Surg. 189(6): 662-6.

Cutuli, B., C. Cohen-Solal-le Nir, et al. (2002). "Breast-conserving therapy for ductal carcinoma in situ of the breast: the French Cancer Centers' experience."Int J Radiat Oncol Biol Phys 53(4): 868-79.

Dean, M., T. Fojo, et al. (2005). "Tumour stem cells and drug resistance." Nat Rev Cancer 5(4): 275-84.

Dewhirst, M. W. (1998). "Concepts of oxygen transport at the microcirculatory level." Semin Radiat Oncol 8(3): 143-50.

Dougherty, T. J., C. J. Gomer, et al. (1998). "Photodynamic therapy." J Natl Cancer Inst 90(12): 889-905.

Edwards, J. G., D. E. Swinson, et al. (2003). "Tumor necrosis correlates with angiogenesis and is a predictor of poor prognosis in malignant mesothelioma." Chest 124(5): 1916-23.

Folkman J. (1996) "Endogenous inhibitors of angiogenesis." Harvey Lect. 92:65-82.

Folkman J. (1997) "Angiogenesis and angiogenesis inhibition: an overview." EXS. 79:1-8. Review.

Folkman J. (2004) "A novel anti-vascular therapy for cancer." Cancer Biol Ther. 3(3):338-9.

Gazdar A F, Kurvari V, Virmani A, Gollahon L, Sakaguchi M, Westerfield M, Kodagoda D, Stasny V, Cunningham H T, Wistuba I I, Tomlinson G, Tonk V, Ashfaq R, Leitch A M, Minna J D, Shay J W. (1998) "Characterization of paired tumor and non-tumor cell lines established from patients with breast cancer." Int J Cancer. 78(6):766-74.

Gross S., Brandis A., et al. (1997). "Protein-A-mediated targeting of bacteriochlorophyll-IgG to Staphylococcus aureus: a model for enhanced site-specific photocytotoxicity." Photochem Photobiol 66(6): 872-8.

Gross S., Gilead A., Brandis A., Schreiber S., Machluf Y., Neeman M., Scherz A. and Salomon Y. (2003a) "Selective vascular and tumor responses of photodynamic therapy (PDT) with Pd bacteriopheophorbide (TOOKAD®): online and offline analyses", Proceedings of the 94th annual meeting of the American association for cancer research (AACR), Toronto, April 5-9, 44: 27.

Gross S, Gilead A, Scherz A, Neeman M, Salomon Y. (2003b) Monitoring photodynamic therapy of solid tumors online by BOLD-contrast MRI. Nat Med. 9(10):1327-31

Guidi A J, Fischer L, Harris J R, Schnitt S J. (1994) "Microvessel density and distribution in ductal carcinoma in situ of the breast." J Natl Cancer Inst. 86(8):614-9.

Guidi A J, Schnitt S J, Fischer L, Tognazzi K, Harris J R, Dvorak H F, Brown L F. (1997) "Vascular permeability factor (vascular endothelial growth factor) expression and angiogenesis in patients with ductal carcinoma in situ of the breast." Cancer. 80(10):1945-53.

Guinebretière J M, Lê Monique G, Gavoille A, Bahi J, Contesso G (1994) "Angiogenesis and risk of breast cancer in women with fibrocystic disease." J Natl Cancer Inst. 86(8): 635-6.

He, X., P. E. Brenchley, et al. (2004). "Hypoxia increases heparanase-dependent tumor cell invasion, which can be inhibited by antiheparanase antibodies." Cancer Res 64(11): 3928-33.

Hendey, B., M. Lawson, et al. (1996). "Intracellular calcium and calcineurin regulate neutrophil motility on vitronectin through a receptor identified by antibodies to integrins alphav and beta3." Blood 87(5): 2038-48.

Hofmann, B., A. Bogdanov, Jr., et al. (1999). "Mechanism of gadophrin-2 accumulation in tumor necrosis." J Magn Reson Imaging 9(2): 336-41.

Holland R, Hendriks J H, Vebeek A L, Mravunac M, Schuurmans Stekhoven J H (1990) "Extent, distribution, and mammographic/histological correlations of breast ductal carcinoma in situ." Lancet. 335(8688):519-22.

Iyer, A. K., G. Khaled, et al. (2006). "Exploiting the enhanced permeability and retention effect for tumor targeting." Drug Discov Today 11(17-18): 812-8.

Kamel, I. R., D. A. Bluemke, et al. (2003). "Role of diffusion-weighted imaging in estimating tumor necrosis after chemoembolization of hepatocellular carcinoma." AJR Am J Roentgenol 181(3): 708-10.

Kato, T., T. Kimura, et al. (1997). "Clinicopathologic study of angiogenesis in Japanese patients with breast cancer." World J Surg 21(1): 49-56.

Kennan, R. P., B. E. Scanley, et al. (1997). "Physiologic basis for BOLD MR signal changes due to hypoxia/hyperoxia: separation of blood volume and magnetic susceptibility effects." Magn Reson Med 37(6): 953-6.

Kepple J, Van Zee K J, Dowlatshahi K, Henry-Tillman R S, Israel P Z, Klimberg V S. (2004) "Minimally invasive breast surgery." J Am Coll Surg. 199(6):961-75. Review Kieran M W, Folkman J, Heymach J. (2003) "Angiogenesis inhibitors and hypoxia." Nat Med. 9(9):1104; author reply 1104-5

Koudinova, N. V., J. H. Pinthus, et al. (2003). "Photodynamic therapy with Pd-Bacteriopheophorbide (TOOKAD): successful in vivo treatment of human prostatic small cell carcinoma xenografts." Int J Cancer 104(6): 782-9.

Krippl P, Langsenlehner U, Renner W, Yazdani-Biuki B, Wolf G, Wascher T C, Paulweber B, Haas J, Samonigg H. (2003) "A common 936 C/T gene polymorphism of vascular endothelial growth factor is associated with decreased breast cancer risk." Int J Cancer. 106(4):468-71.

Lang, P., M. F. Wendland, et al. (1998). "Osteogenic sarcoma: noninvasive in vivo assessment of tumor necrosis with diffusion-weighted MR imaging." Radiology 206(1): 227-35.

Lee, A. H., L. C. Happerfield, et al. (1997). "Angiogenesis and inflammation in invasive carcinoma of the breast." J Clin Pathol 50(8): 669-73.

Lee, K., R. A. Roth, et al. (2007). "Hypoxia, drug therapy and toxicity." Pharmacol Ther 113(2): 229-46.

Lee, S. E., S. K. Hong, et al. (2007). "Prognostic significance of tumor necrosis in primary transitional cell carcinoma of upper urinary tract." Jpn J Clin Oncol 37(1): 49-55.

Leek, R. D., R. J. Landers, et al. (1999). "Necrosis correlates with high vascular density and focal macrophage infiltration in invasive carcinoma of the breast." Br J Cancer 79(5-6): 991-5.

Lehtio, K., O. Eskola, et al. (2004). "Imaging perfusion and hypoxia with PET to predict radiotherapy response in head-and-neck cancer." Int J Radiat Oncol Biol Phys 59(4): 971-82.

Lyons, S. K. (2005). "Advances in imaging mouse tumour models in vivo." J Pathol 205(2): 194-205.

Maeda, H., J. Wu, et al. (2000). "Tumor vascular permeability and the EPR effect in macromolecular therapeutics: a review." J Control Release 65(1-2): 271-84.

Maeshima, Y., P. C. Colorado, et al. (2000). "Two RGD-independent alpha vbeta 3 integrin binding sites on tumstatin regulate distinct anti-tumor properties." J Biol Chem 275(31): 23745-50.

Marugan, J. J., C. Manthey, et al. (2005). "Design, synthesis, and biological evaluation of novel potent and selective alphavbeta3/alphavbeta5 integrin dual inhibitors with improved bioavailability. Selection of the molecular core." J Med Chem 48(4): 926-34.

Mazor, O., A. Brandis, et al. (2005). "WST11, a novel water-soluble bacteriochlorophyll derivative; cellular uptake, pharmacokinetics, biodistribution and vascular-targeted photodynamic activity using melanoma tumors as a model."Photochem Photobiol 81(2): 342-51.

Metz, S., H. E. Daldrup-Unk, et al. (2003). "Detection and quantification of breast tumor necrosis with MR imaging: value of the necrosis-avid contrast agent Gadophrin-3." Acad Radiol 10(5): 484-90.

Minchinton, A. I. and I. F. Tannock (2006). "Drug penetration in solid tumours." Nat Rev Cancer 6(8): 583-92.

Ni, Y., G. Bormans, et al. (2005). "Necrosis avid contrast agents: functional similarity versus structural diversity." Invest Radiol 40(8): 526-35.

Nyberg, P., M. Ylipalosaari, et al. (2006). "Trypsins and their role in carcinoma growth." Exp Cell Res 312(8): 1219-28.

Patan S, Munn L L, Jain R K. (1996) "Intussusceptive microvascular growth in a human colon adenocarcinoma xenograft: a novel mechanism of tumor angiogenesis." Microvasc Res. 51(2):260-72.

Patterson, A. V., D. M. Ferry, et al. (2007). "Mechanism of action and preclinical antitumor activity of the novel hypoxia-activated DNA cross-linking agent PR-104." Clin Cancer Res 13(13): 3922-32.

Plaks V, Kalchenko V, Dekel N, Neeman M. (2006) "MRI analysis of angiogenesis during mouse embryo implantation." Magn Reson Med. 55(5):1013-22.

Preise D., Mazor O., Koudinova N., Liscovitch M., Scherz A. and Salomon Y. (2003) "Bypass Of Tumor Drug Resistance By Antivascular Therapy", Neoplasia 5(6):475-80

Rankin S C. (2000) "MRI of the breast." Br J Radiol. 73(872):806-18. Review.

Relf M, LeJeune S, Scott P A, Fox S, Smith K, Leek R, Moghaddam A, Whitehouse R, Bicknell R, Harris A L. (1997) "Expression of the angiogenic factors vascular endothelial cell growth factor, acidic and basic fibroblast growth factor, tumor growth factor beta-1, platelet-derived endothelial cell growth factor, placenta growth factor, and pleiotrophin in human primary breast cancer and its relation to angiogenesis." Cancer Res. 57(5):963-9.

Rosenbach-Belkin V, Chen L, Fiedor L, Tregub I, Paviotsky F, Brumfeld V, Salomon Y, Scherz A. (1996) "Serine conjugates of chlorophyll and bacteriochlorophyll: photocytotoxicity in vitro and tissue distribution in mice bearing melanoma tumors." Photochem Photobiol. 64(1):174-81.

Rubinstein, E., A. Brandis, et al. "Vascular-Targeted Photodynamic Therapy (VTP), Imaging (VTI) and localization of primary lesions and metastases by novel Bacteriochlorophyll (BCL)-RGD conjugates." In preparation.

Sanders M E, Schuyler P A, Dupont W D, Page D L. (2005) "The natural history of low-grade ductal carcinoma in situ of the breast in women treated by biopsy only revealed over 30 years of long-term follow-up." Cancer. 103(12):2481-4

Schaffner, P. and M. M. Dard (2003). "Structure and function of RGD peptides involved in bone biology." Cell Mol Life Sci 60(1): 119-32.

Schneider B P, Miller K D. (2005) "Angiogenesis of breast cancer." J Clin Oncol. 23(8):1782-90. Review Schreiber S., Gross S., Brandis A., Harmelin A., Rosenbach-Belkin V., Scherz A. and Salomon Y. (2002) "Local photodynamic therapy (PDT) of rat C6 glioma xenografts with Pd-bacteriopheophorbide leads to decreased metastases and increase of animal cure compared with surgery", Int. J. Cancer, 99: 279-285.

Sengupta, S., C. M. Lohse, et al. (2005). "Histologic coagulative tumor necrosis as a prognostic indicator of renal cell carcinoma aggressiveness." Cancer 104(3): 511-20.

Shimizu K, Asai T, Oku N. (2005) "Antineovascular therapy, a novel antiangiogenic approach." Expert Opin Ther Targets. 9(1):63-76.

Shirakawa, K., H. Tsuda, et al. (2001). "Absence of endothelial cells, central necrosis, and fibrosis are associated with aggressive inflammatory breast cancer." Cancer Res 61(2): 445-51.

Streubel B, Chott A, Huber D, Exner M, Jäger U, Wagner O, Schwarzinger I. (v) "Lymphoma-specific genetic aberrations in microvascular endothelial cells in B-cell lymphomas." N Engl J Med. 351(3):250-9.

Tait, L. R., R. J. Pauley, et al. (2007). "Dynamic stromal-epithelial interactions during progression of MCF10DCIS.com xenografts." Int J Cancer 120(10): 2127-34.

Takagi, J. (2004). "Structural basis for ligand recognition by RGD (Arg-Gly-Asp)-dependent integrins." Biochem Soc Trans 32(Pt3): 403-6.

Tanaka, T., S. Shiramoto, et al. (2004). "Tumor targeting based on the effect of enhanced permeability and retention (EPR) and the mechanism of receptor-mediated endocytosis (RME)." Int J Pharm 277(1-2): 39-61.

Tannock, I. (1978). "Cell kinetics and chemotherapy: a critical review."Cancer Treat Rep 62(8): 1117-33.

Tannock, I. F. and D. Rotin (1989). "Acid pH in tumors and its potential for therapeutic exploitation." Cancer Res 49(16): 4373-84.

Temming, K., R. M. Schiffelers, et al. (2005). "RGD-based strategies for selective delivery of therapeutics and imaging agents to the tumour vasculature."Drug Resist Updat 8(6): 381-402.

Thorpe P E (2004) "Vascular targeting agents as cancer therapeutics." Clin Cancer Res. 10(2):415-27. Review.

Tomes, L., E. Emberley, et al. (2003). "Necrosis and hypoxia in invasive breast carcinoma." Breast Cancer Res Treat 81(1): 61-9.

Vaupel, P., D. K. Kelleher, et al. (2001). "Oxygen status of malignant tumors: pathogenesis of hypoxia and significance for tumor therapy." Semin Oncol 28(2 Suppl 8): 29-35.

Wapnir, I. L., N. Barnard, et al. (2001). "The inverse relationship between microvessel counts and tumor volume in breast cancer." Breast J 7(3): 184-8.

Weersink R A, Bogaards A, Gertner M, Davidson S R, Zhang K, Netchev G, Trachtenberg J, Wilson B C. (2005) "Techniques for delivery and monitoring of TOOKAD (WST09)-mediated photodynamic therapy of the prostate: clinical experience and practicalities." J Photochem Photobiol B. 79(3):211-22.

Weinmann, M., C. Belka, et al. (2004). "Tumour hypoxia: impact on biology, prognosis and treatment of solid malignant tumours." Onkologie 27(1): 83-90.

Yang, M., E. Baranov, et al. (2000). "Whole-body optical imaging of green fluorescent protein-expressing tumors and metastases." Proc Natl Acad Sci USA 97(3): 1206-11.

Zilberstein J., Bromberg A., Frantz A., Rosenbach-Belkin V., Kritzmann A., Pfefermann R., Salomon Y. and Scherz A. (1997) "Light-dependent oxygen consumption in bacteriochlorophyll-serine-treated melanoma tumors: on-line determination using a tissue-inserted oxygen microsensor", Photochem Photobiol., 65(6):1012-1019.

Zilberstein J., Schreiber S., Bloemers M. C. W. M., Bendel P., Neeman M., Schechtman E., Kohen F., Scherz A. and Salomon Y. (2001) "Antivascular treatment of solid melanoma tumors with bacteriochlorophyll-serine-based photodynamic therapy", Photochem. Photobiol., 73: 257-266.

The invention claimed is:

1. A method for diagnosis and visualization of tumor necrotic domains by minimally invasive imaging of tumors, said method comprising:
   (i) administering to a subject suspected of having a tumor with necrotic domains a conjugate of an RGD-containing peptide or a non-peptidic compound that mimics a peptide and has the RGD motif and a photosensitizer;
   (ii) imaging the subject at least 24-48 hours after said administration; and
   (iii) diagnosing the presence or absence of said tumor necrotic domains,
   wherein said photosensitizer is a chlorophyll or bacteriochlorophyll of the formula II:

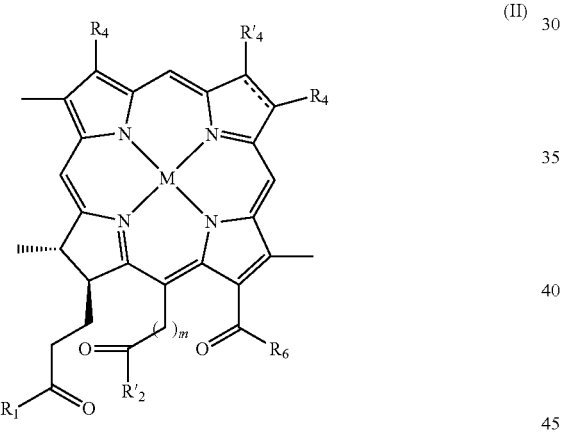

wherein
M represents 2H or an atom selected from the group consisting of Mg, Pd, Pt, Co, Ni, Sn, Cu, Zn, Mn, In, Eu, Fe, Au, Al, Gd, Dy, Er, Yb, Lu, Ga, Y, Rh, Ru, Si, Ge, Cr, Mo, P, Re, Tc and Ti and isotopes and radio-isotopes thereof;
$R_1$, $R'_2$ and $R_6$ each independently is Y—$R_8$, —$NR_9R'_9$ or —$N^+R_9R'_9R''_9A^-$; or $R_1$ and $R_6$ together form a ring comprising an RGD-containing peptide or a residue of a non-peptidic compound that mimics a peptide and has the RGD motif;
Y is O or S;
$R_4$ is —CH=$CR_9R'_9$, —CH=$CR_9$Hal, —CH=CH—$CH_2$—$NR_9R'_9$, —CH=CH—$CH_2$—$N^+R_9R'_9R''_9A^-$, —CHO, —CH=$NR_9$, —CH=$N^+R_9R'_9A^-$, —$CH_2$—$OR_9$, —$CH_2$—$SR_9$, —$CH_2$-Hal, —$CH_2$—$R_9$, —$CH_2$—$NR_9R'_9$, —$CH_2$—$N^+R_9R'_9R''_9A^-$, —$CH_2$—$CH_2R_9$, —$CH_2$—$CH_2$Hal, —$CH_2$—$CH_2OR_9$, —$CH_2$—$CH_2SR_9$, —$CH_2$—$CH_2$—$NR_9R'_9$, —$CH_2$—$CH_2$—$N^+R_9R'_9R''_9A^-$, —$COCH_3$, —$C(CH_3)$=$CR_9R'_9$, —$C(CH_3)$=$CR_9$Hal, —$C(CH_3)$=$NR_9$, —$CH(CH_3)$=$N^+R_9R'_9A^-$, —$CH(CH_3)$-Hal, —$CH(CH_3)$—$OR_9$, —$CH(CH_3)$—$SR_9$, —$CH(CH_3)$—$NR_9R'_9$, —$CH(CH_3)$—$N^+R_9R'_9R''_9A^-$, or —C≡$CR_9$;
$R'_4$ is methyl or formyl;
$R_8$, $R_9$, $R'_9$ and $R''_9$ each independently is:
(a) H;
(b) $C_1$-$C_{25}$ hydrocarbyl;
(c) $C_1$-$C_{25}$ hydrocarbyl substituted by one or more functional groups selected from the group consisting of halogen, nitro, oxo, OR, SR, epoxy, epithio, —CONRR', —COR, COOR, —$OSO_3R$, —$SO_3R$, —$SO_2R$, —$NHSO_2R$, —$SO_2NRR'$—NRR', =N—OR, =N—NRR', —C(=NR)—NRR', —NR—NRR', —(R)N—C(=NR)—NRR', O←NR—, >C=NR, —$(CH_2)_n$—NR—COR', —$(CH_2)_n$—CO—NRR', —O—$(CH_2)_n$—OR, —O—$(CH_2)_n$—O—$(CH_2)_n$—R, —PRR', —$OPO_3RR'$, -$PO_2HR$ and n is an integer from 1 to 6 —$PO_3RR'$, wherein R and R' each independently is H, hydrocarbyl or heterocyclyl, R' is optionally a residue of an RGD-containing peptide or a non-peptidic compound that mimics a peptide and has the RGD motif, or R and R' together with the N atom to which they are attached form a 5-7 membered saturated ring optionally containing a further heteroatom selected from the group consisting of O, S and N, wherein the further N atom is optionally substituted, and R" is H, a cation, hydrocarbyl or heterocyclyl;
(d) $C_1$-$C_{25}$ hydrocarbyl substituted by one or more functional groups selected from the group consisting of positively charged groups, negatively charged groups, basic groups that are converted to positively charged groups under physiological conditions selected from the group consisting of —NRR', —C(=NR)—NR'R", —NR—NR'R", —(R)N—C(=NR)—NR'R", O←NRR'—, and >C=NR, wherein R, R' and R" each independently is H, optionally substituted hydrocarbyl or heterocyclyl, or two of R, R' and R" together with the N atom to which they are attached form a 3-7 membered saturated ring, optionally containing one or more heteroatoms selected from the group consisting of O, S or N, and optionally further substituted at the additional N atom, or the basic group is an N-containing heteroaromatic radical selected from the group consisting of pyrazolyl, imidazolyl, oxazolyl, thiazolyl, pyridyl, quinolinyl, isoquinolinyl, pyrimidyl, 1,2,4-triazinyl, 1,3,5-triazinyl or purinyl, and acidic groups that are converted to negatively charged groups under physiological conditions selected from the group consisting of COOH, COSH, $SO_3H$, and $PO_3H_2$, or a salt thereof;
(e) $C_1$-$C_{25}$ hydrocarbyl containing one or more heteroatoms and/or one or more carbocyclic or heterocyclic moieties;
(f) $C_1$-$C_{25}$ hydrocarbyl containing one or more heteroatoms and/or one or more carbocyclic or heterocyclic moieties and substituted by one or more functional groups as defined in (c) and (d) above;

(g) $C_1$-$C_{25}$ hydrocarbyl substituted by an amino acid residue, an RGD-containing peptide, a protein, a monosaccharide, an oligosaccharide, a polysaccharide, or a polydentate ligand and its chelating complexes with metals; or (h) a residue of an amino acid, an RGD-containing peptide or a non-peptidic compound that mimics a peptide and has the RGD motif, a protein, a monosaccharide, an oligosaccharide, a polysaccharide; or a polydentate ligand and its chelating complexes with metals;

$R_8$ is optionally $H^+$ or a cation $R^+_{10}$ when $R_1$, $R'_2$ and $R_6$ each independently is Y—$R_8$;

$R^+_{10}$ is a metal cation, an ammonium group or an organic cation derived from an amine or from a N-containing group selected from the group consisting of ammonium, hydrazinium, ammoniumoxy, iminium, amidinium or guanidinium;

$A^-$ is a physiologically acceptable anion;

m is 0 or 1;

Hal is a halogen selected from fluoro, chloro, bromo or iodo;

the dotted line at positions 7-8 represents an optional double bond; and pharmaceutically acceptable salts and optical isomers thereof;

wherein said carbocyclic moiety is a saturated or partially unsaturated monocyclic or polycyclic compound containing only carbon atoms in the ring(s); said heterocyclic moiety or said heterocyclyl is a radical derived from a mono- or poly-cyclic heteroaromatic ring containing one to three O, S and/or N heteroatoms, selected from the group consisting of pyrrolyl, furyl, thienyl, pyrazolyl, imidazolyl, oxazolyl, thiazolyl, pyridyl, quinolinyl, pyrimidinyl, 1,3,4-triazinyl, 1,2,3-triazinyl, 1,3,5-triazinyl, benzofuryl, isobenzofuryl, indolyl, imidazo[1,2-a]pyridyl, benzimidazolyl, benzthiazolyl and benzoxazolyl; and wherein said carbocyclic and heterocyclic moieties are optionally substituted by one or more radicals selected from the group consisting of halogen, $C_6$-$C_{14}$ aryl, $C_1$-$C_{25}$ alkyl, nitro, OR, SR, —COR, —COOR, —SO$_3$R, —SO$_2$R, —NHSO$_2$R, —NRR', (CH$_2$)—NR—COR' and —(CH$_2$)—CO—NRR';

and wherein said chlorophyll or bacteriochlorophyll contains at least one RGD-containing peptide or a non-peptidic compound that mimics a peptide and has the RGD motif.

2. The method according to claim 1, wherein the positions 7-8 of said photosensitizer are hydrogenated and the photosensitizer is a bacteriochlorophyll, wherein: (i) each $R_4$, independently, is acetyl, vinyl, ethyl, or 1-hydroxyethyl radical or an ether or ester of 1-hydroxyethyl radical; (ii) $R'_4$ is methyl; and (iii) any of the $C_1$-$C_{25}$ hydrocarbyl is a $C_1$-$C_{25}$ alkyl, alkenyl or alkynyl, optionally substituted by at least one functional group selected from the group consisting of:

(a) a negatively charged group, selected from the group consisting of COO$^-$, COS$^-$, SO$_3^-$, and PO$_3^{2-}$;

(b) an acidic group that is converted to a negatively charged group at the physiological selected from the group consisting of COOH, COSH, SO$_3$H, and PO$_3$H$_2$, or a salt thereof;

(c) a positively charged group, selected from the group consisting of: an onium group selected from the group consisting of —O$^+$(RR'), —S$^+$(RR'), —Se$^+$(RR'), —Te$^+$(RR'), —P$^+$(RR'R"), —As$^+$(RR'R"), —Sb$^+$(RR'R"), and —Bi$^+$(RR'R"); a cation selected from the group consisting of —N$^+$(RR'R"), —(R)N—N$^+$(RR'R"), O←N$^+$(RR'R")—, >C=N$^+$(RR'), —C(=NR)—N$^+$RR'R" or —(R)N—C(=NR)—N$^+$RR'R" group; and a cation selected from the group consisting of pyrazolium, imidazolium, oxazolium, thiazolium, pyridinium, quinolinium, isoquinolinium, pyrimidinium, 1,2,4-triazinium, 1,3,5-triazinium or purinium; and (d) a basic group that is converted to a positively charged group under physiological conditions selected from the group consisting of —NRR', —C(=NR)—NR'R", —NR—NR'R", —(R)N—C(=NR)—NR'R", O←NRR'—, and >C=NR, said basic group is an end group or a group located within an alkyl chain;

wherein R, R' and R" each independently is H, optionally substituted hydrocarbyl or heterocyclyl, or two of R, R' and R" together with the N atom to which they are attached form a 3-7 membered saturated ring, optionally containing one or more heteroatoms selected from the group consisting of O, S or N, wherein the N atom is optionally substituted, said ring is selected from the group consisting of aziridine, pyrrolidine, piperidine, morpholine, thiomorpholine, azepine or piperazine optionally substituted at the additional N atom by $C_1$-$C_6$ alkyl optionally substituted by halo, hydroxyl or amino.

3. The method according to claim 2, wherein said bacteriochlorophyll is of formula II and $R_6$ is —NR$_9$R'$_9$ wherein $R_9$ is H and R'$_9$ is selected from the group consisting of: (i) $C_1$-$C_{10}$ alkyl substituted by SO$_3$H or an alkaline salt thereof; and (ii) $C_1$-$C_6$ alkyl substituted by a basic group —NRR' or —NH—(CH$_2$)$_{2-6}$—NRR', wherein each of R and R' independently is H, $C_1$-$C_6$ alkyl optionally substituted by NH$_2$, or R and R' together with the N atom form a 5-6 membered saturated ring, optionally containing an O or N atom and optionally further substituted at the additional N atom by —(CH$_2$)$_{2-6}$—NH$_2$.

4. The method according to claim 3, wherein $R_6$ is (i) —NH—(CH$_2$)$_2$—SO$_3$K or —NH—(CH$_2$)$_3$—SO$_3$K; or (ii) —NH—(CH$_2$)$_3$—NH—(CH$_2$)$_3$—NH$_2$, —NH—(CH$_2$)$_2$-1-morpholino, or —NH—(CH$_2$)$_3$-piperazino-(CH$_2$)$_3$—NH$_2$.

5. The method according to claim 1, wherein the photosensitizer is a bacteriochlorophyll of formula II and $R_1$ and $R_6$ together form a cyclic ring comprising an RGD-containing peptide or a non-peptidic compound that mimics a peptide and has the RGD motif.

6. The method according to claim 1, wherein the RGD-containing peptide is an all-L, all-D or an L,D-linear or cyclic peptide composed of 4-100, natural, modified natural or non-natural amino acids, wherein the natural amino acids are selected from the group consisting of Ala, Arg, Asn, Asp, Cys, His, Gln, Glu, Gly, Ile, Leu, Lys, Met, Phe, Pro, Ser, Thr, Trp, Tyr and Val, and the modification of said modified natural or non-natural amino acids is selected from the group consisting of D-modification, alkylation or acylation of the amino terminal group or of the free amino group of lysine, esterification or amidation of the carboxy terminal group or of the acid free carboxy group of aspartic or glutamic acid, and etherification or esterification of the free hydroxyl group of serine or tyrosine.

7. The method according to claim 6, wherein the RGD-containing peptide is a cyclic peptide, selected from the group consisting of the pentapeptide c(RGDfK) (SEQ ID NO:1), wherein f indicates D-Phe, c(RGDK) (SEQ ID NO:3), c(RGDf-n(Me)K) (SEQ ID NO: 4), c(RGDyK)(SEQ ID NO: 5), wherein y is D-Tyr; or a linear peptide selected from the group consisting of CDCRGDCGC (SEQ ID NO: 9); the hexapeptide GRGDSP (SEQ ID NO: 6); the heptapeptide GRGDSPK (SEQ ID NO: 7); or the 25-mer (GRGDSP)$_4$K (SEQ ID NO: 8).

8. The method according to claim 1, wherein the conjugate is compound 13 of the formula:

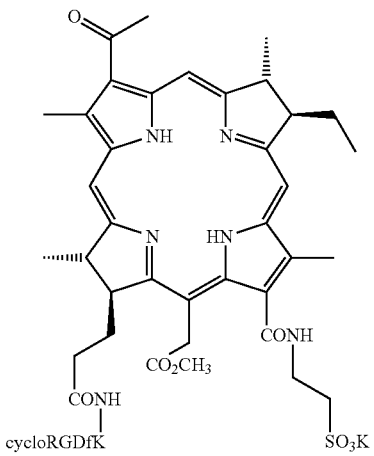

or compound 24 of the formula:

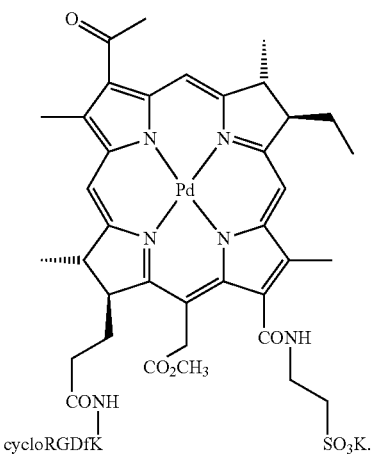

9. The method according to claim 1, wherein the tumor is a primary tumor or a metastatic tumor with necrotic domains, selected from the group consisting of melanoma, prostate, brain, colon, ovarian, breast, colorectal, head and neck, chest wall tumor arising from breast cancer, skin, lung, esophagus and bladder cancer and tumor.

10. The method according to claim 9, wherein the tumor is localized breast cancer.

11. The method according to claim 1, for mapping the margins of said tumor necrotic domains before surgery by dynamic fluorescence imaging, said method comprising:
   (a) administering to said subject suspected of having a tumor with necrotic domains said conjugate of formula II, wherein M is 2H or a metal selected from Pd and Zn; and
   (b) illuminating the subject and measuring the fluorescence of the suspected areas during at least 24-48 hours after administration of the conjugate at time intervals of 1-8 hours, wherein the areas that exhibit fluorescence after 24-48 hours or longer indicate the presence of said tumor necrotic domains.

12. The method according to claim 11, wherein the conjugate is compound 13 of the formula:

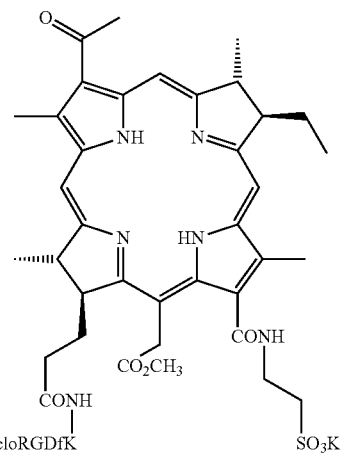

or compound 24 of the formula:

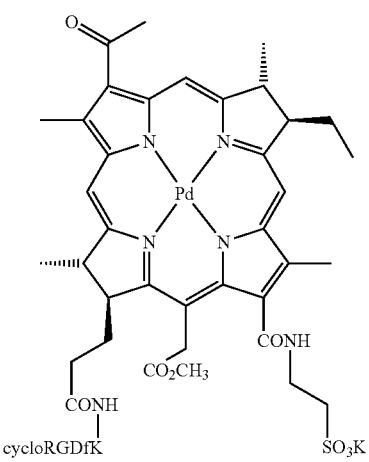

the tumor is mammary or ovarian tumor, and the necrotic domains are visualized 3 to 8 days post drug injection.

13. The method according to claim 1, for diagnosis of said tumor necrotic domains by a radiodiagnostic technique, said method comprising:
   (a) administering to said subject suspected of having a tumor with necrotic domains said conjugate of formula II, wherein M is a radioisotope selected from the group consisting of $^{64}$Cu, $^{67}$Cu, $^{99m}$Tc, $^{67}$Ga, $^{201}$Tl, $^{195}$Pt, $^{60}$Co, $^{111}$In or $^{51}$Cr; and
   (b) scanning the subject in an imaging scanner during at least 24-48 hours after administration of the conjugate at time intervals of 1-8 hours, and measuring the radiation level of the suspected areas, wherein the areas that exhibit radiation after 24-48 hours or longer indicate the presence of said tumor necrotic domains.

14. The method according to claim 13, wherein said radiodiagnostic technique is positron emission tomography (PET) and M is $^{64}$Cu or $^{67}$Cu, or single photon emission tomography (SPET) and M is a radioisotope selected from the group consisting of $^{99m}$Tc, $^{67}$Ga, $^{195}$Pt, $^{111}$In, $^{51}$Cr and $^{60}$Co.

15. The method according to claim 1, for diagnosis of said tumor necrotic domains by magnetic resonance imaging (MRI), said method comprising:

(a) administering to a subject suspected of having a tumor comprising necrotic domains said conjugate of formula II, wherein M is a paramagnetic metal selected from $Mn^{3+}$, $Cu^{2+}$, $Fe^{3+}$, $Eu^{3+}$, $Gd^{3+}$ or $Dy^{3+}$;

(b) subjecting the patient to magnetic resonance imaging by generating at least one MR image of the target region of interest within the patient's body prior to said administration (zero time) and one or more MR images at a second or more time points at least 24-48 hours after said administration; and (c) processing and analyzing the data to diagnose the presence or absence of said tumor necrotic domains.

16. A method for mapping the margins of the viable tumor cells before surgery, comprising administering to a subject in need a conjugate as defined in claim 1, and imaging said tumor margins, at the first 2-24h after administration of the conjugate.

17. A method for minimally invasive treatment of localized breast cancer comprising necrotic domains with a conjugate of formula II, comprising (i) administering to a subject in need an effective amount of said conjugate of formula II; (ii) imaging said subject for tumor detection and tumor margin definition at high precision as well as prognosis by an imaging method according to claim 1 selected from the group consisting of MRI, fluorescence, and PET SCAN; and (iii) illumination said subject for tumor-targeted photodynamic therapy (PDT) of the localized necrotic areas allowing breast conservation and remodeling, wherein said conjugate of formula II is

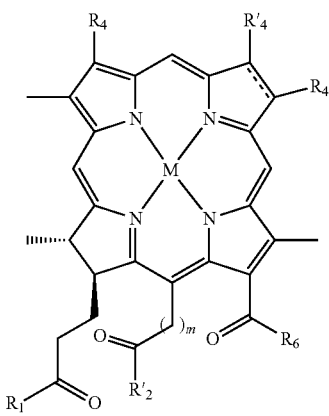

and m, M, $R_1$, $R'_2$, $R_4$, $R'_4$, and $R_6$ are defined in claim 1.

18. A method for tumor-targeted photodynamic therapy (PDT) of necrotic tumors, comprising:
(i) administering to a subject suspected of having a tumor with necrotic domains a conjugate of an RGD-containing peptide or a non-peptidic compound that mimics a peptide and has the RGD motif and a photosensitizer as defined in claim 1;
(ii) tumor-targeted imaging the subject treated with said conjugate according to the method of claim 1 for minimally invasive tumor-targeted imaging, on-line prognosis and/or mapping of tumor margins; and
(iii) irradiating the local of the tumor and its necrotic domains after determining the presence of necrotic domains in (ii) at least 24 hours after injection of the conjugate.

19. The method according to claim 18, wherein the conjugate is compound 13 of the formula:

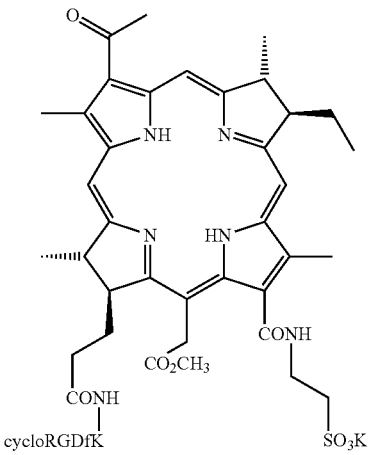

or compound 24 of the formula:

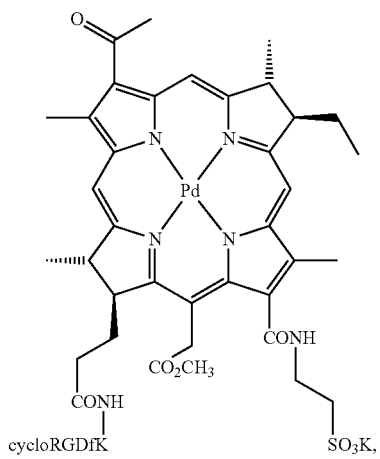

the tumor is mammary or ovarian tumor, and the necrotic domains are treated 2 to 8 days post drug injection.

20. The method according to claim 10, wherein said localized breast cancer is ductal carcinoma in situ (DCIS).

21. The method according to claim 17, wherein said localized breast cancer is ductal carcinoma in situ (DCIS).

22. The method according to claim 16, wherein said tumor is breast tumor.

* * * * *